United States Patent
Ishiyama et al.

(10) Patent No.: US 9,902,794 B2
(45) Date of Patent: Feb. 27, 2018

(54) CURABLE COMPOSITION, OPTICAL COMPONENT AND COMPOUND

(71) Applicant: FUJIFILM Corporation, Tokyo (JP)

(72) Inventors: Ayumi Ishiyama, Ahigarakami-gun (JP); Naoyuki Morooka, Ahigarakami-gun (JP); Seiichi Hitomi, Ahigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/265,922

(22) Filed: Sep. 15, 2016

(65) Prior Publication Data

US 2017/0002124 A1    Jan. 5, 2017

(30) Foreign Application Priority Data

Mar. 19, 2014 (JP) ................................. 2014-056051

(51) Int. Cl.
| | | |
|---|---|---|
| C08F 2/46 | (2006.01) | |
| C08F 2/50 | (2006.01) | |
| C08G 61/04 | (2006.01) | |
| C08F 222/10 | (2006.01) | |
| C07D 263/57 | (2006.01) | |
| C07D 277/60 | (2006.01) | |
| C07D 277/64 | (2006.01) | |
| C07D 277/66 | (2006.01) | |
| C08F 220/28 | (2006.01) | |

(52) U.S. Cl.
CPC ...... *C08F 222/1006* (2013.01); *C07D 263/57* (2013.01); *C07D 277/60* (2013.01); *C07D 277/64* (2013.01); *C07D 277/66* (2013.01); *C08F 2/50* (2013.01); *C08F 2220/281* (2013.01); *C08F 2222/102* (2013.01)

(58) Field of Classification Search
None
See application file for complete search history.

(56) References Cited

U.S. PATENT DOCUMENTS

| | | | |
|---|---|---|---|
| 8,451,234 B2 | 5/2013 | Sato et al. | |
| 8,952,079 B2 | 2/2015 | Morooka et al. | |
| 2009/0009486 A1 | 1/2009 | Sato et al. | |
| 2013/0237630 A1 | 9/2013 | Morooka et al. | |

FOREIGN PATENT DOCUMENTS

| | | | |
|---|---|---|---|
| JP | 2008-65748 A | 3/2008 | |
| JP | 2009-15489 A | 1/2009 | |
| JP | 2010-44453 A | 2/2010 | |
| JP | 2011-68624 A | 4/2011 | |
| JP | 2012-107191 A | 6/2012 | |
| JP | 2014-12826 A | 1/2014 | |
| WO | 2014-208767 | * 12/2014 | |

OTHER PUBLICATIONS

Takuma et al, WO 2014-208767 Machine Translation, Dec. 31, 2014.*
International Search Report for PCT/JP2015/055317 dated May 19, 2015.
Written Opinion for PCT/JP2015/055317 dated May 19, 2015.
International Preliminary Report on Patentability, dated Sep. 29, 2016, from the International Bureau in counterpart International Application No. PCT/JP2015/055317.

* cited by examiner

*Primary Examiner* — Jessica Whiteley
(74) *Attorney, Agent, or Firm* — Sughrue Mion, PLLC

(57) ABSTRACT

Provided are a curable composition exhibiting excellent solvent solubility while maintaining a high refractive index; an optical component using such a curable composition; and a compound. The curable composition contains a compound represented by the following Formula (1) and at least one kind selected from thermal radical polymerization initiators or photo radical polymerization initiators. In Formula (1), $Ar^1$ to $Ar^4$ each independently represent an aromatic ring, at least one of $Ar^1$, . . . , or $Ar^4$ represents a benzothiazole ring, a benzoxazole ring, an aromatic ring containing a benzothiazole ring or a benzoxazole ring, or an aromatic ring having a benzothiazolyl group or a benzoxazolyl group as a substituent, and two or more of $Y^1$ to $Y^4$ represent a polymerizable group.

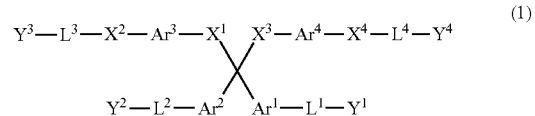

24 Claims, No Drawings

CURABLE COMPOSITION, OPTICAL COMPONENT AND COMPOUND

CROSS-REFERENCE TO RELATED APPLICATIONS

This application is a Continuation of PCT International Application No. PCT/JP2015/055317 filed on Feb. 25, 2015, which claims priority under 35 U.S.C §119(a) to Japanese Patent Application No. 2014-056051 filed on Mar. 19, 2014. Each of the above application(s) is hereby expressly incorporated by reference, in its entirety, into the present application.

BACKGROUND OF THE INVENTION

1. Field of the Invention

The present invention relates to a curable composition, from which a cured material exhibiting transparency and a high refractive index can be obtained, an optical component, and a compound.

2. Description of the Related Art

An imaging module has been used in a camera, a video camera, a mobile phone with a camera, a video phone, a door-phone with a camera, or the like. In recent years, particularly, it has been required to downsize an optical component used in the imaging module. However, if the optical component becomes miniaturized, the chromatic aberration of the optical system becomes a serious problem.

As a material for the optical component, a glass material has been used, but there is a problem that a glass material has poor workability. In contrast, a resin has excellent workability as well as being cheaper than a glass material. Therefore, in recent years, attempts have been made to use a resin in such an optical component.

Further, in recent years, highly functional organic materials have come to be required when developing electronic devices such as transparent touch panels, liquid crystal displays, an organic electroluminescence (EL) display, optical semiconductor (LED) elements, solid-state imaging devices, organic thin-film solar cells, dye-sensitized solar cells, organic thin-film transistors (TFT), or the like.

For example, types of touch panel are divided into a resistive film type, an optical type, a capacitive type, an ultrasonic type, a pressure type, an electromagnetic wave induction type, an image recognition type, a vibration detection type, or the like.

As a specific example of a touch panel disposed on a display device such as liquid crystal displays is a resistive film type or a capacitive type. A resistive film type is a type detecting the pressed position using a voltage, and the resistance film type is for capturing a change in capacitance caused by pressing and for detecting a position.

For example, JP2008-65748A, JP2009-15489A and JP2010-44453A disclose a capacitive type, and it has been realized to provide an insulating film and a protective film in its layered structure in order to prevent erroneous recognition of a position at which there is conflict.

However, in a case where a curable composition is applied on the surface of another layer such as a transparent electrode pattern such as ITO to form an insulating film, a protective film or the like, since the refractive index difference becomes larger, an ITO pattern becomes more visible, and thus, there is a problem that the visibility of the liquid crystal display screen is greatly reduced. Therefore, there is a demand for a curable composition capable of forming a film exhibiting a high refractive index.

Thus, in recent years, there is a demand for a curable composition capable of forming a cured material having a high refractive index.

JP2011-68624A and JP2014-12826A disclose a composition including (meth)acrylates having a 9,9-bisphenylfluorene skeleton and (meth)acrylates having 9,9-bisnaphthylfluorene skeleton, which is used in such optical components or the like.

JP2012-107191A discloses a composition including a (meth)acrylate monomer having an alicyclic structure and a non-conjugated vinylidene group-containing compound, which is used in such optical components or the like.

SUMMARY OF THE INVENTION

The present inventors have investigated JP2011-68624A and JP2014-12826A, and have found that the solubility in a solvent (hereinafter, also referred to as solvent solubility) of compounds disclosed in these documents was insufficient.

Accordingly, an object of the present invention is to provide a curable composition exhibiting excellent solvent solubility while maintaining a high refractive index. Further, another object of the present invention is to provide an optical component using such a curable composition, and a compound exhibiting excellent solvent solubility while maintaining a high refractive index.

The present inventors have conducted intensive studies and, as a result, have found that the curable composition including a compound represented by the following Formula (1) exhibits excellent solvent solubility while maintaining a high refractive index. This has led to the above-mentioned problems being solved. Specifically, the above-mentioned problems have been solved by the following solving means <1> and preferably by the following solving means <2> to <25>.

<1> A curable composition comprising:
a compound represented by the following Formula (1); and
at least one kind selected from thermal radical polymerization initiators or photo-radical polymerization initiators,

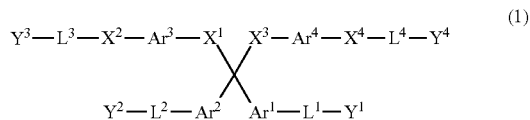

(1)

in Formula (1), $Ar^1$ to $Ar^4$ each independently represent an aromatic ring, $Ar^1$ and $Ar^2$, $Ar^3$ and $Ar^4$, $Ar^2$ and $Ar^3$, and $Ar^1$ and $Ar^4$ may link to each other to form a fused ring, respectively, at least one of $Ar^1$, ..., or $Ar^4$ is a benzothiazole ring, a benzoxazole ring, an aromatic ring containing a benzothiazole ring or a benzoxazole ring, or an aromatic ring having a group including a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ represent an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^1$ to $X^4$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

<2> The curable composition according to <1>, wherein the compound represented by the above Formula (1) is a compound represented by the following Formula (11),

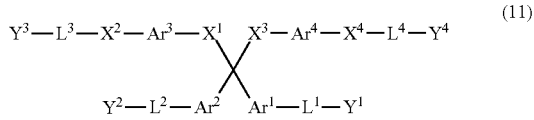

(11)

in Formula (11), $Ar^1$ to $Ar^4$ each independently represent a monocyclic aromatic ring to a tricyclic aromatic ring, $Ar^1$ and $Ar^2$ may have a phenyl group or a naphthyl group as a substituent, $Ar^1$ and $Ar^2$, or $Ar^3$ and $Ar^4$ may link to each other to form a fused ring containing a 5-membered ring or a 6-membered ring, at least one of $Ar^1$, . . . , or $Ar^4$ represents a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^1$ to $X^4$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

<3> The curable composition according to <1>, wherein the compound represented by the above Formula (1) is a compound represented by the following Formula (2),

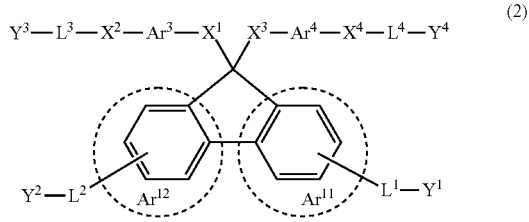

(2)

in Formula (2), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ are an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^1$ to $X^4$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

<4> The curable composition according to <1>, wherein the compound represented by the above Formula (1) is a compound represented by the following Formula (3A) or (3B),

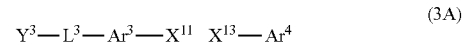

(3A)

(3B)

in Formulae (3A) and (3B), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^2$ to $L^4$ each independently represent a single bond, an alkylene group, an alkenylene group, or an alkynylene group, in a case where $L^2$ to $L^4$ are an alkylene group, an alkenylene group, or an alkynylene group, $L^2$ to $L^4$ may include a divalent linking group selected from the group having one or more selected from —O—, —S—, —CO—, and —NR— in the linking chain, R represents a hydrogen atom or an alkyl group, $X^{11}$ and $X^{13}$ each independently represent a single bond, a phenylene group or a naphthylene group, at least one of $X^{11}$ or $X^{13}$ is a phenylene group or a naphthylene group, and $Y^2$ to $Y^4$ each independently represent a polymerizable group.

<5> The curable composition according to <4>, wherein at least one of $Ar^3$ or $Ar^4$ in the above Formula (3A) or Formula (3B) is a benzothiazole ring, a benzoxazole ring, an aromatic ring containing a benzothiazole ring or a benzoxazole ring, or an aromatic ring having a benzothiazolyl group or a benzoxazolyl group as a substituent.

<6> The curable composition according to <4> or <5>, wherein at least one of $Ar^3$ or $Ar^4$ in the above Formula (3A) or Formula (3B) is a benzothiazole ring, an aromatic ring having a benzothiazole ring, or an aromatic ring having a benzothiazolyl group as a substituent.

<7> The curable composition according to <1>, wherein the compound represented by the above Formula (1) is a compound represented by the following Formula (4),

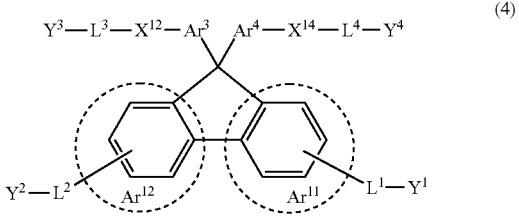

(4)

in Formula (4), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ are an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^{12}$ and $X^{14}$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

<8> The curable composition according to <1>, wherein the compound represented by the above Formula (1) is a compound represented by the following Formula (5),

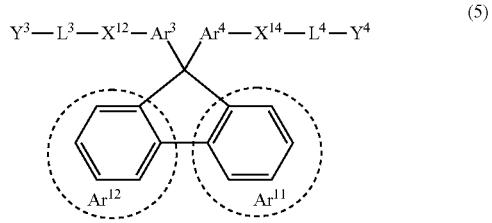

(5)

in Formula (5), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^3$ and $L^4$ each independently represent a single bond, an alkylene group, an alkenylene group, or an alkynylene group, in a case where $L^3$ and $L^4$ are an alkylene group, an alkenylene group, or an alkynylene group, $L^3$ and $L^4$ may include a divalent linking group selected from the group having one or more selected from —O—, —S—, —CO—, and —NR— in the linking chain, R represents a hydrogen atom or an alkyl group, $X^{12}$ and $X^{14}$ each independently represent a single bond, a phenylene group or a naphthylene group, and $Y^3$ and $Y^4$ each independently represent a polymerizable group.

<9> The curable composition according to <8>, wherein at least one of $Ar^3$ or $Ar^4$ in the above Formula (5) is a benzothiazole ring, a benzoxazole ring, an aromatic ring containing a benzothiazole ring or a benzoxazole ring, or an aromatic ring having a benzothiazolyl group or a benzoxazolyl group as a substituent.

<10> The curable composition according to <8> or <9>, wherein at least one of $Ar^3$ or $Ar^4$ in the above Formula (5) is a benzothiazole ring, an aromatic ring having a benzothiazole ring, or an aromatic ring having a benzothiazolyl group as a substituent.

<11> The curable composition according to any one of <8> to <10>, wherein $Ar^3$ in the above Formula (5) is a benzothiazole ring, an aromatic ring having a benzothiazole ring, or an aromatic ring having a benzothiazolyl group as a substituent, and $X^{12}$ is a phenylene group or a naphthylene group, and/or $Ar^4$ is a benzothiazole ring, an aromatic ring having a benzothiazole ring, or an aromatic ring having a benzothiazolyl group as a substituent, and $X^{14}$ is a phenylene group or a naphthylene group.

<12> The curable composition according to any one of <1> to <11>, further comprising a thermal radical polymerization initiator and a photo radical polymerization initiator.

<13> The curable composition according to any one of <1> to <12>, further comprising a monofunctional (meth)acrylate monomer in a proportion of 10% by mass to 200% by mass with respect to the compound represented by the above Formula (1).

<14> The curable composition according to any one of <1> to <13> which is used for a coating composition.

<15> An optical component using the curable composition according to any one of <1> to <13>.

<16> A compound represented by the following Formula (11),

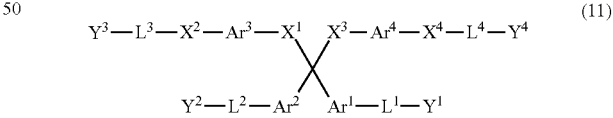

(11)

in Formula (11), $Ar^1$ to $Ar^4$ each independently represent a monocyclic aromatic ring to a tricyclic aromatic ring, $Ar^1$ and $Ar^2$ may have a phenyl group or a naphthyl group as a substituent, $Ar^1$ and $Ar^2$, or $Ar^3$ and $Ar^4$ may link to each other to form a fused ring containing a 5-membered ring or a 6-membered ring, at least one of $Ar^1$, . . . , or $Ar^4$ represents a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^1$ to $X^4$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

<17> The compound according to <16>, wherein the compound represented by the above Formula (11) is a compound represented by the following Formula (12),

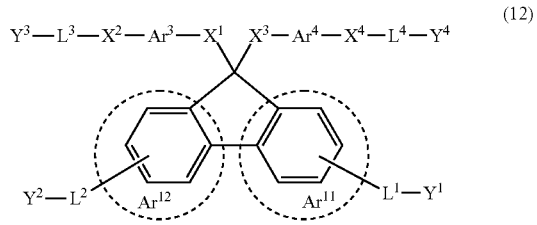

(12)

in Formula (12), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^1$ to $X^4$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

<18> The compound according to <16>, wherein the compound represented by the above Formula (11) is a compound represented by the following Formula (13A) or (13B),

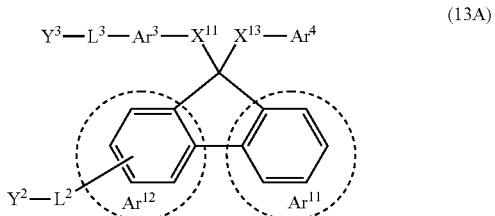

(13A)

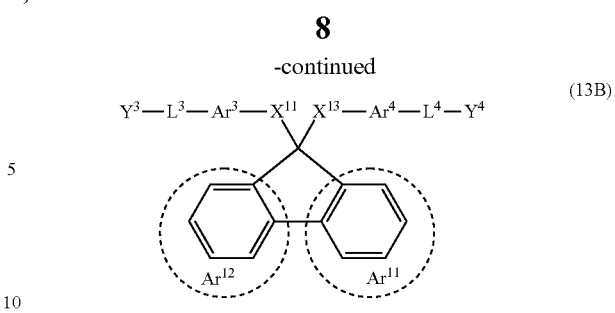

(13B)

in Formulae (13A) and (13B), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^2$ to $L^4$ each independently represent an alkylene group having 1 to 20 carbon atoms, in a case where $L^2$ to $L^4$ are an alkylene group having 2 to 20 carbon atoms, $L^2$ to $L^4$ may include a divalent linking group selected from the group having one or more selected from —O—, —S—, —CO—, and —NH— in the linking chain, $X^{11}$ and $X^{13}$ each independently represent a single bond, a phenylene group or a naphthylene group, at least one of $X^{11}$ or $X^{13}$ is a phenylene group or a naphthylene group, and $Y^2$ to $Y^4$ each independently represent a polymerizable group having an ethylenically unsaturated bond.

<19> The compound according to <18>, wherein at least one of $Ar^3$ or $Ar^4$ in the above Formula (13A) or Formula (13B) is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent.

<20> The compound according to <18> or <19>, wherein at least one of $Ar^3$ or $Ar^4$ in the above Formula (13A) or Formula (13B) is a benzothiazole ring, a tricyclic aromatic ring containing a benzothiazole ring, or a benzene ring or a naphthalene ring having a benzothiazolyl group as a substituent.

<21> The compound according to <16>, wherein the compound represented by the above Formula (11) is a compound represented by the following Formula (14),

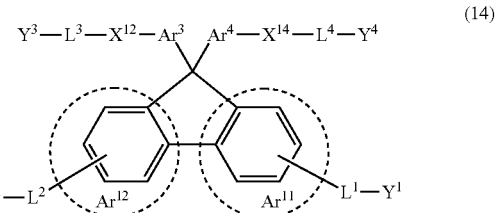

(14)

in Formula (14), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, 2, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^{12}$ and $X^{14}$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

<22> The compound according to <16>, wherein the compound represented by the above Formula (11) is a compound represented by the following Formula (15),

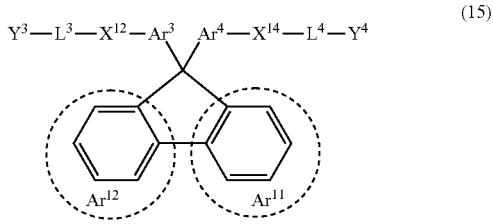

(15)

in Formula (15), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^3$ and $L^4$ each independently represent an alkylene group having 1 to 20 carbon atoms, in a case where $L^3$ and $L^4$ are an alkylene group having 2 to 20 carbon atoms, $L^3$ and $L^4$ may include a divalent linking group selected from the group having one or more selected from —O—, —S—, —CO—, and —NH— in the linking chain, $X^{12}$ and $X^{14}$ each independently represent a single bond, a phenylene group or a naphthylene group, and $Y^3$ and $Y^4$ each independently represent a polymerizable group having an ethylenically unsaturated bond.

<23> The compound according to <22>, wherein at least one of $Ar^3$ or $Ar^4$ in the above Formula (15) is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent.

<24> The compound according to <22> or <23>, wherein at least one of $Ar^3$ or $Ar^4$ in the above Formula (15) is a benzothiazole ring, a tricyclic aromatic ring containing a benzothiazole ring, or a benzene ring or a naphthalene ring having a benzothiazolyl group as a substituent.

<25> The compound according to any one of <22> to <24>, wherein $Ar^3$ in the above Formula (15) is a benzothiazole ring, a tricyclic aromatic ring containing a benzothiazole ring, or a benzene ring or a naphthalene ring having a benzothiazolyl group as a substituent, and $X^{12}$ is a phenylene group or a naphthylene group, and/or $Ar^4$ is a benzothiazole ring, a tricyclic aromatic ring containing a benzothiazole ring, or a benzene ring or a naphthalene ring having a benzothiazolyl group as a substituent, and $X^{14}$ is a phenylene group or a naphthylene group.

According to the present invention, it has become possible to provide a curable composition exhibiting excellent solvent solubility while maintaining a high refractive index. Further, it has become possible to provide an optical component using such a curable composition and a compound exhibiting excellent solvent solubility while maintaining a high refractive index.

DESCRIPTION OF THE PREFERRED EMBODIMENTS

Hereinafter, the present invention will be described in detail. The description of constituent elements described below can be made based on exemplary embodiments and specific examples, but the present invention is not limited to such embodiments.

Numerical ranges expressed using "to" in this specification mean a range including numerical values described before and after "to" as the lower limit and the upper limit.

In the present invention, "(meth)acrylate" is intended to mean "acrylate" or "methacrylate." Also, "(meth) acryloyl" is intended to mean "acryloyl" or "methacryloyl."

In representation of the group (atomic group) in the present specification, the representation denoted without the substituted and unsubstituted groups is also intended to include those having a substituent together with those not having a substituent. For example, an "alkyl group" includes not only an alkyl group (an unsubstituted alkyl group) not having a substituent, but also an alkyl group (a substituted alkyl group) having a substituent.

In the present invention, a hydrogen atom represents that it also includes its isotope (such as a deuterium atom) in the case where it is used without being particularly distinguished in the description of each formula. Further, the atom constituting a substituent represents that it also includes its isotope.

<Curable Composition>

The curable composition of the present invention includes a compound represented by Formula (1) and at least one kind selected from thermal radical polymerization initiators and photo radical polymerization initiators.

With this configuration, the curable composition of the present invention exhibits a good solvent solubility, and thus it is possible to manufacture a cured material having a high refractive index. The reason why such an effect was obtained is not clear in detail, but it is considered that the density of aromatic rings is increased, the crystallinity is decreased, and the solvent solubility is improved because of a structure obtained by connecting four aryl groups with a quaternary carbon. Therefore, it is considered that the refractive index is improved by introducing a benzothiazole structure and a benzoxazole structure as the aryl group.

<<The Compound Represented by Formula (1)>>

Hereinafter, the compound represented by Formula (1) will be described.

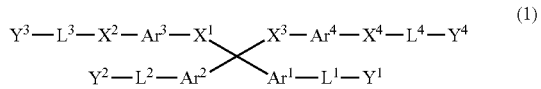

In Formula (1), $Ar^1$ to $Ar^4$ each independently represent an aromatic ring, $Ar^1$ and $Ar^2$, $Ar^3$ and $Ar^4$, $Ar^2$ and $Ar^3$, and $Ar^1$ and $Ar^4$ may link to each other to form a fused ring, respectively, at least one of $Ar^1, \ldots,$ or $Ar^4$ is a benzothiazole ring, a benzoxazole ring, an aromatic ring containing a benzothiazole ring or a benzoxazole ring, or an aromatic ring having a group containing a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ represent an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^1$ to $X^4$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

$Ar^1$ to $Ar^4$ of Formula (1) each independently represent an aromatic ring.

A monocyclic aromatic ring to a tricyclic aromatic ring are preferable as an aromatic ring. Specific examples thereof include a benzene ring, a naphthalene ring, a fused ring formed by condensing a benzene ring and a monocyclic heterocyclic aromatic ring or bicyclic heterocyclic aromatic ring and the like. Examples of a hetero atom constituting a heterocyclic aromatic ring may include a nitrogen atom, an oxygen atom, and a sulfur atom. As a ring constituting a heterocyclic aromatic ring, a 5-membered ring or a 6-membered ring is preferable, and a 5-membered ring is more preferable. Examples of a fused ring formed by condensing a benzene ring and a heterocyclic aromatic ring include a benzothiazole ring, a benzoxazole ring, an indole ring, an indazole ring, a benzothiophene ring, a benzofuran ring, an isobenzofuran ring, a benzoimidazole ring, a benzoisoxazole ring, a benzisoxazole ring, a quinoline ring, an isoquinoline ring, a phthalazine ring and the like.

An aromatic ring represented by $Ar^1$ to $Ar^4$ may have a substituent, and examples of a substituent include an alkyl group, an alkoxy group, an aryl group, a heteroaryl group and the like.

As an alkyl group, an alkyl group having 1 to 30 carbon atoms is preferable, an alkyl group having 1 to 20 carbon atoms is more preferable, an alkyl group having 1 to 10 carbon atoms is particularly preferable, and an alkyl group having 1 to 5 carbon atoms is most preferable. An alkyl group may be any of a linear, branched or cyclic group.

As an alkoxy group, an alkoxy group having 1 to 30 carbon atoms is preferable, an alkoxy group having 1 to 20 carbon atoms is more preferable, an alkoxy group having 1 to 10 carbon atoms is particularly preferable, an alkoxy group having 1 to 5 carbon atoms is most preferable. An alkoxy group may be any of a linear, branched or cyclic group.

As an aryl group, an aryl group having 5 to 30 carbon atoms is preferable, an aryl group having 5 to 20 carbon atoms is more preferable, and an aryl group having 5 to 14 carbon atoms is particularly preferable.

A heteroaryl group may be a monocyclic ring or polycyclic ring. The number of hetero atoms constituting a heteroaryl group is preferably 1 to 3. A hetero atom constituting a heteroaryl group is preferably a nitrogen atom, an oxygen atom or a sulfur atom. The number of carbon atoms in heteroaryl group is preferably 3 to 30, more preferably 3 to 18, and more preferably 3 to 12. Specific examples of a heteroaryl group include a benzothiazolyl group, a benzoxazolyl group, an imidazoyl group, a pyridyl group and the like.

In a case where a substituent is a benzothiazolyl group or a benzoxazolyl group, an aromatic ring represented by $Ar^1$ to $Ar^4$ is preferably a benzene ring or a naphthalene ring.

$Ar^1$ and $Ar^2$, $Ar^3$ and $Ar^4$, $Ar^2$ and $Ar^3$, and $Ar^1$ and $Ar^4$ may respectively link to each other to form a fused ring, but it is preferable that one of $Ar^1$ and $Ar^2$ or $Ar^3$ and $Ar^4$ are bonded, and further preferable that $Ar^1$ and $Ar^2$ are bonded. Examples of the fused ring which these linked to form are not particularly limited. Examples thereof include an alicyclic (non-aromatic hydrocarbon ring), an aromatic ring, a heterocyclic ring, a lactone ring and the like, but a fused ring including a 5-membered ring or a 6-membered ring is preferable. Among them, it is preferable to constitute a fused ring having a fluorene ring as a partial structure by linking $Ar^1$ and $Ar^2$. Further, it is preferable for $Ar^3$ and $Ar^4$, $Ar^2$ and $Ar^3$, and $Ar^1$ and $Ar^4$ not to form a fused ring.

At least one of $Ar^1, \ldots,$ or $Ar^4$ represents a benzothiazole ring, a benzoxazole ring, an aromatic ring containing a benzothiazole ring or a benzoxazole ring, or an aromatic ring having a group containing a benzothiazolyl group or a benzoxazolyl group as a substituent. At least one of $Ar^1, \ldots,$ or $Ar^4$ is preferably a benzothiazole ring, an aromatic ring having a benzothiazole ring, or an aromatic ring having a benzothiazolyl group as a substituent. At least one of $Ar^3$ or $Ar^4$ is particularly preferably a benzothiazole ring, an aromatic ring having a benzothiazole ring, or an aromatic ring having a benzothiazolyl group as a substituent.

Further, an aromatic ring containing a benzothiazole ring or a benzoxazole ring is preferably a tricyclic aromatic ring.

As an aromatic ring having a group containing a benzothiazolyl group or a benzoxazolyl group as a substituent, it is preferable that an aromatic ring in which a substituent is a benzothiazolyl group or a benzoxazolyl group, but it is preferable that an aromatic ring having a substituent in which some hydrogen atoms of the above described substituents may be substituted by a benzothiazolyl group or a benzoxazolyl group.

$L^1$ to $L^4$ each independently represent a single bond, an alkylene group, an alkenylene group, or an alkynylene group, in a case where $L^1$ to $L^4$ are an alkylene group, an alkenylene group, or an alkynylene group, $L^1$ to $L^4$ may include a divalent linking group selected from the group having one or more selected from —O—, —S—, —CO—, and —NR— (R represents a hydrogen atom or alkyl group, preferably a hydrogen atom or an alkyl group having 1 to 20 carbon atoms, and particularly preferably hydrogen atom) in the linking chain.

Moreover, a group including the above described divalent linking group in linking chains of an alkylene group, an alkenylene group, or an alkynylene group means a group that is configured of two or more alkylene groups, alkenylene groups, or alkynylene groups through the above described divalent linking group.

The number of carbon atoms of an alkylene group is preferably 1 to 20, and particularly preferably 1 to 12. Further, in a case where an alkylene group includes the above described divalent linking group in its linking chain, the total number of carbon atoms of alkylene group is preferably 1 to 12, and particularly preferably 1 to 10.

The number of carbon atoms of an alkenylene group is preferably 1 to 20, and particularly preferably 1 to 12. Further, in a case where an alkenylene group includes the above described divalent linking group in its linking chain, the total number of carbon atoms of an alkenylene group is preferably 1 to 12, and particularly preferably 1 to 10.

The number of carbon atoms of an alkynylene group is preferably 1 to 20, and particularly preferably 1 to 12. Further, in a case where an alkynylene group includes the above described divalent linking group in its linking chain, the total number of carbon atoms of an alkynylene group is preferably 1 to 12, and particularly preferably 1 to 10.

As a group represented by $L^1$ to $L^4$, an alkylene group, or a group including the above described divalent linking group in linking chains of an alkylene group is preferable.

$Y^1$ to $Y^4$ each independently represent a hydrogen atom, an aryl group or a polymerizable group, and two or more of $Y^1$ to $Y^4$ represent a polymerizable group. Two or three of $Y^1$ to $Y^4$ preferably represent a polymerizable group, and two of $Y^1$ to $Y^4$ particularly preferably represent a polymerizable group.

As a preferred embodiment in a case where $Y^1$ to $Y^4$ represent a polymerizable group, a combination in which $Y^2$ and $Y^3$ are a polymerizable group, or a combination in which $Y^3$ and $Y^4$ are a polymerizable group is preferable, and a combination in which $Y^3$ and $Y^4$ are a polymerizable group is particularly preferable. This enables the composition to further improve solvent solubility.

The polymerizable group is not particularly limited as long as it is a group which causes a curing reaction by photoirradiation or heat treatment. Examples thereof include an epoxy group, an oxetanyl group, a group represented by —NH—CH2-O—R (R is a hydrogen atom or an alkyl group having 1 to 20 carbon atoms), a polymerizable group having an ethylenically unsaturated bond, a block isocyanate group, an alkoxymethyl group, a methylol group, an amino group and the like. Examples of a polymerizable group having an ethylenically unsaturated bond include a vinyl group, an allyl group, a methallyl group, a methacryloyl group, an acryloyl group, an allyloxycarbonyl group, a methallyl oxycarbonyl group and the like.

As a polymerizable group, a polymerizable group having an ethylenically unsaturated bond is preferable, a vinyl group, an allyl group, an acryloyl group, or a methacryloyl group is more preferable, and an acryloyl group or a methacryloyl group is particularly preferable.

$X^1$ to $X^4$ each independently represent a single bond, a phenylene group or a naphthylene group. At least one selected from $X^1$ to $X^4$ is preferably a phenylene group or a naphthylene group. Among them, it is preferred that $X^1$ and $X^3$ are a single bond, or $X^2$ and $X^4$ is a single bond. In particular, it is preferred that $X^1$ and $X^3$ are a single bond, and $X^2$ and $X^4$ represent a phenylene group or a naphthylene group, and it is preferred $X^1$ and $X^3$ are a phenylene group or a naphthylene group and $X^2$ and $X^4$ are a single bond.

The compound represented by Formula (1) is preferably a compound represented by the following Formula (2).

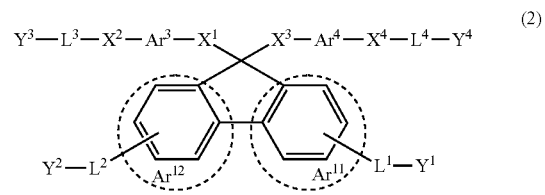

(2)

In Formula (2), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ are an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^1$ to $X^4$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

$Ar^{11}$, $Ar^{12}$, $Ar^3$ and $Ar^4$ in Formula (2) have the same meaning as $Ar^1$ to $Ar^4$ in Formula (1), and their preferred ranges are also similar. $Ar^3$ and $Ar^4$ may link to each other to form a fused ring, but it is preferable not to form a fused ring.

$L^1$ to $L^4$ in Formula (2) have the same meaning as $L^1$ to $L^4$ in Formula (1), and their preferred ranges are also similar.

$Y^1$ to $Y^4$ in Formula (2) have the same meaning as $Y^1$ to $Y^4$ in Formula (1), and their preferred ranges are also similar.

The compound represented by Formula (1) is preferably a compound represented by the following Formula (3A) or Formula (3B).

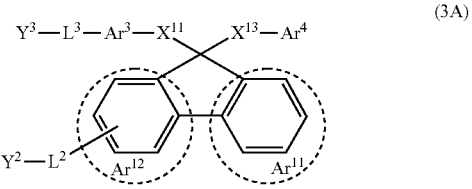

(3A)

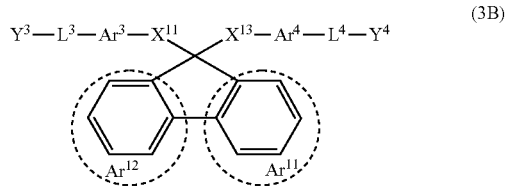

(3B)

In Formulae (3A) and (3B), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^2$ to $L^4$ each independently represent a single bond, an alkylene group, an alkenylene group, or an alkynylene group, in a case where $L^2$ to $L^4$ are an alkylene group, an alkenylene group, or an alkynylene group, $L^2$ to $L^4$ may include a divalent linking group selected from the group having one or more selected from —O—, —S—, —CO—, and —NR— in the linking chain, R represents a hydrogen atom or an alkyl group, $X^{11}$ and $X^{13}$ each independently represent a single bond, a phenylene group or naphthylene group, at least one of $X^{11}$ or $X^{13}$ is a phenylene group or a naphthylene group, and $Y^2$ to $Y^4$ each independently represent a polymerizable group.

$Ar^{11}$, $Ar^{12}$, $Ar^3$ and $Ar^4$ in Formula (3A) and Formula (3B) have the same meaning as $Ar^1$ to $Ar^4$ in Formula (1), and their preferred ranges are also similar. $Ar^3$ and $Ar^4$ may link to each other to form a fused ring, but it is preferable not to form a fused ring.

In Formula (3A) or Formula (3B), preferably, at least one of $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent. More preferably, at least one of $Ar^3$ or $Ar^4$ is a benzothiazole ring, an aromatic ring having a benzothiazole ring, or an aromatic ring having a benzothiazolyl group as a substituent.

$Ar^{11}$ and $Ar^{12}$ in Formula (3A) or Formula (3B) are preferably a benzene ring or a naphthalene ring.

According to this aspect, it is possible to provide a curable composition exhibiting excellent solvent solubility while maintaining a high refractive index.

$L^2$ to $L^4$ in Formula (3A) and Formula (3B) have the same meaning as $L^2$ to $L^4$ in Formula (1), and their preferred ranges are also similar.

$Y^2$ to $Y^4$ in Formula (3A) and Formula (3B) have the same meaning as $Y^2$ to $Y^4$ in Formula (1), and their preferred ranges are also similar.

The compound represented by Formula (1) is preferably a compound represented by the following Formula (4).

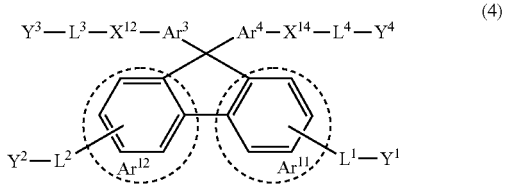

(4)

In Formula (4), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ are an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^{12}$ and $X^{14}$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

$Ar^{11}$, $Ar^{12}$, $Ar^3$ and $Ar^4$ in Formula (4) have the same meaning as $Ar^1$ to $Ar^4$ in Formula (1), and their preferred ranges are also similar. $Ar^3$ and $Ar^4$ may link to each other to form a fused ring, but it is preferable not to form a fused ring.

$L^1$ to $L^4$ in Formula (4) have the same meaning as $L^1$ to $L^4$ in Formula (1), and their preferred ranges are also similar.

$Y^1$ to $Y^4$ in Formula (4) have the same meaning as $Y^1$ to $Y^4$ in Formula (1), and their preferred ranges are also similar.

The compound represented by Formula (1) is preferably a compound represented by the following Formula (5).

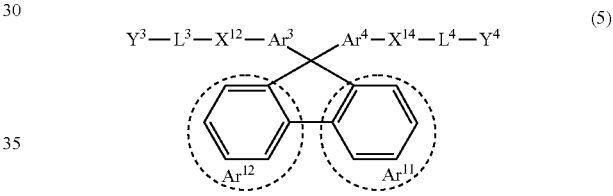

(5)

In Formula (5), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^3$ and $L^4$ each independently represent a single bond, an alkylene group, an alkenylene group, or an alkynylene group, in a case where $L^3$ and $L^4$ are an alkylene group, an alkenylene group, or an alkynylene group, $L^3$ and $L^4$ may include a divalent linking group selected from the group having one or more selected from —O—, —S—, —CO—, and —NR— in the linking chain, R represents a hydrogen atom or an alkyl group, $X^{12}$ and $X^{14}$ each independently represent a single bond, a phenylene group or a naphthylene group, and $Y^3$ and $Y^4$ each independently represent a polymerizable group.

$Ar^{11}$, $Ar^{12}$, $Ar^3$ and $Ar^4$ in Formula (5) have the same meaning as $Ar^1$ to $Ar^4$ Formula (1), and their preferred ranges are also similar. $Ar^3$ and $Ar^4$ may link to form a fused ring, but it is preferable not to form a fused ring.

In Formula (5), preferably, at least one of $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent. More preferably, at least one of $Ar^3$ or $Ar^4$ is a benzothiazole ring, an aromatic ring having a benzothiazole ring, or an aromatic ring having a benzothiazolyl group as a substituent. Particularly preferably, $Ar^3$ is a benzothiazole ring, an aromatic ring having a benzothiazole ring, or an aromatic ring having a benzothiazolyl group as a substituent, and $X^{12}$ is a phenylene group or a naphthylene group, and/or $Ar^4$ is a benzothiazole ring, an aromatic ring having a benzothiazole ring, or an aromatic ring having a benzothiazolyl group as a substituent, and $X^{14}$ is a phenylene group or a naphthylene group.

$Ar^{11}$ and $Ar^{12}$ in Formula (5) is preferably a benzene ring or a naphthalene ring.

According to this aspect, it is possible to provide a curable composition exhibiting an excellent solvent solubility while maintaining a high refractive index.

$L^3$ and $L^4$ in Formula (5) have the same meaning as $L^3$ and $L^4$ in Formula (1), and their preferred ranges are also similar.

$Y^3$ and $Y^4$ in Formula (5) have the same meaning as $Y^3$ and $Y^4$ in Formula (1), and their preferred ranges are also similar.

The compound represented by Formula (1) is preferably a compound represented by the following Formula (11). A compound represented by the following Formula (11) may be the compound of the present invention.

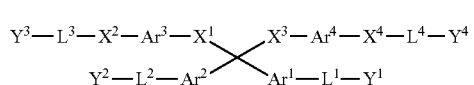
(11)

In Formula (11), $Ar^1$ to $Ar^4$ each independently represent a monocyclic aromatic ring to a tricyclic aromatic ring, $Ar^1$ and $Ar^2$ may have a phenyl group or a naphthyl group as a substituent, $Ar^1$ and $Ar^2$, or $Ar^3$ and $Ar^4$ may link to each other to form a fused ring containing a 5-membered ring or a 6-membered ring, at least one of $Ar^1$, . . . , or $Ar^4$ represent a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^1$ to $X^4$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

$Ar^1$ to $Ar^4$ in Formula (11) each independently represent a monocyclic aromatic ring to a tricyclic aromatic ring.

Examples of a monocyclic aromatic ring to a tricyclic aromatic ring include a benzene ring, a naphthalene ring, a fused ring formed by condensing a benzene ring and a monocyclic heterocyclic aromatic ring to bicyclic heterocyclic aromatic ring and the like. Examples of a hetero atom constituting a heterocyclic aromatic ring can include a nitrogen atom, an oxygen atom, and a sulfur atom. As a ring constituting a heterocyclic aromatic ring, a 5-membered ring or a 6-membered ring is preferable, and a 5-membered ring is more preferable. Examples of a fused ring formed by condensing a benzene ring and a heterocyclic aromatic ring include a benzothiazole ring, a benzoxazole ring, an indole ring, an indazole ring, a benzothiophene ring, a benzofuran ring, an isobenzofuran ring, a benzoimidazole ring, a benzoisoxazole ring, a benzisoxazole ring, a quinoline ring, an isoquinoline ring, a phthalazine ring and the like.

$Ar^1$ and $Ar^2$ may have a phenyl group or a naphthyl group as a substituent.

In addition, an aromatic ring represented by $Ar^1$ to $Ar^4$ may have a benzothiazolyl group or a benzoxazolyl group as a substituent.

In a case where an aromatic ring represented by $Ar^1$ to $Ar^4$ may have a benzothiazolyl group or a benzoxazolyl group as a substituent, an aromatic ring represented by $Ar^1$ to $Ar^4$ is a benzene ring or a naphthalene ring.

$Ar^1$ and $Ar^2$, or $Ar^3$ and $Ar^4$ may link to each other to form a fused ring including a 5-membered ring or a 6-membered ring. It is preferable to constitute a fused ring having a fluorene ring as a partial structure by linking $Ar^1$ and $Ar^2$. Further, it is preferable for $Ar^3$ and $Ar^4$ not to form a fused ring.

At least one of $Ar^1$, . . . , or $Ar^4$ represents a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent.

At least one of $Ar^1$, . . . , or $Ar^4$ is preferably a benzothiazole ring, a tricyclic aromatic ring containing a benzothiazole ring, or a benzene ring or a naphthalene ring having a benzothiazolyl group as a substituent.

$L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain.

Further, a group including the above described divalent linking group in linking chains of an alkylene group means a group that is configured of two or more alkylene groups through the above described divalent linking group.

The number of carbon atoms of an alkylene group is preferably 1 to 20, and particularly preferably 1 to 12. Further, in a case where an alkylene group includes the above described divalent linking group in its linking chain, the total number of carbon atoms of alkylene group is preferably 1 to 12, and particularly preferably 1 to 10.

$Y^1$ to $Y^4$ each independently represent hydrogen atom or a polymerizable group having an ethylenically unsaturated bond, and two or more of $Y^1$ to $Y^4$ represent a polymerizable group having an ethylenically unsaturated bond.

Examples of a polymerizable group having an ethylenically unsaturated bond include a vinyl group, an allyl group, a methallyl group, a methacryloyl group, an acryloyl group, an allyloxycarbonyl group, a methallyl oxycarbonyl group and the like. A vinyl group, an allyl group, an acryloyl group, or a methacryloyl group is preferable, and an acryloyl group or a methacryloyl group is particularly preferable.

The compound represented by Formula (1) is preferably a compound represented by the following Formula (12). A compound represented by the following Formula (12) may be the compound of the present invention.

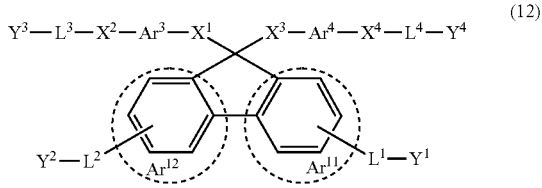
(12)

In Formula (12), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^1$ to $X^4$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

$Ar^{11}$, $Ar^{12}$, $Ar^3$ and $Ar^4$ in Formula (12) have the same meaning as $Ar^1$ to $Ar^4$ in Formula (11), and their preferred ranges are also similar.

$L^1$ to $L^4$ in Formula (12) have the same meaning as $L^1$ to $L^4$ in Formula (11), and their preferred ranges are also similar.

$Y^1$ to $Y^4$ in Formula (12) have the same meaning as $Y^1$ to $Y^4$ in Formula (11), and their preferred ranges are also similar.

The compound represented by Formula (1) is preferably a compound represented by the following Formula (13A) or Formula (13B). A compound represented by the following Formula (13A) or Formula (13B) may be also the compound of the present invention.

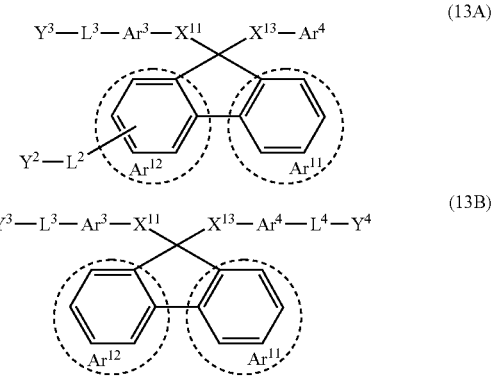
(13A)

(13B)

In Formulae (13A) and (13B), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^2$ to $L^4$ each independently represent an alkylene group having 1 to 20 carbon atoms, in a case where $L^2$ to $L^4$ is an alkylene group having 2 to 20 carbon atoms, $L^2$ to $L^4$ may include a divalent linking group selected from the group having one or more selected from —O—, —S—, —CO—, and —NH— in the linking chain, $X^{11}$ and $X^{13}$ each independently represent a single bond, a phenylene group or a naphthylene group, at least one of $X^{11}$ or $X^{13}$ is a phenylene group or a naphthylene group, and $Y^2$ to $Y^4$ each independently represent a polymerizable group having an ethylenically unsaturated bond.

$Ar^{11}$, $Ar^{12}$, $Ar^3$ and $Ar^4$ in Formula (13A) and Formula (13B) have the same meaning as $Ar^1$ to $Ar^4$ in Formula (11), and their preferred ranges are also similar.

In Formula (13A) or Formula (13B), preferably, at least one of $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent. More preferably, at least one of $Ar^3$ or $Ar^4$ is a benzothiazole ring, a tricyclic aromatic ring containing a benzothiazole ring, or a benzene ring or a naphthalene ring having a benzothiazolyl group as a substituent.

$Ar^{11}$ and $Ar^{12}$ in Formula (13A) or Formula (13B) are preferably a benzene ring or a naphthalene ring.

According to this aspect, it is possible to provide a curable composition exhibiting an excellent solvent solubility while maintaining a high refractive index.

$L^2$ to $L^4$ in Formula (13A) and Formula (13B) have the same meaning as $L^2$ to $L^4$ in Formula (11), and preferred ranges thereof are also the same.

$Y^2$ to $Y^4$ in Formula (13A) and Formula (13B) have the same meaning as $Y^2$ to $Y^4$ in Formula (11), and preferred ranges thereof are also the same.

The compound represented by Formula (1) is preferably a compound represented by the following Formula (14). A compound represented by the following Formula (14) may also be the compound of the present invention.

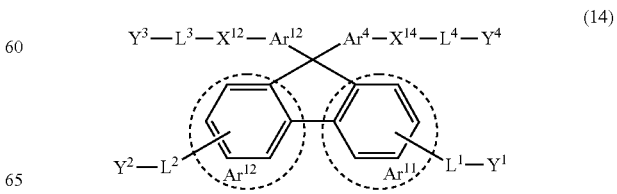
(14)

In Formula (14), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^{12}$ and $X^{14}$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

$Ar^{11}$, $Ar^{12}$, $Ar^3$ and $Ar^4$ in Formula (14) have the same meaning as $Ar^1$ to $Ar^4$ in Formula (11), and their preferred ranges are also similar.

$L^1$ to $L^4$ in Formula (14) have the same meaning as $L^1$ to $L^4$ in Formula (11), and their preferred ranges are also similar.

$Y^1$ to $Y^4$ in Formula (14) have the same meaning as $Y^1$ to $Y^4$ in Formula (11), and their preferred ranges are also similar.

The compound represented by Formula (1) is preferably a compound represented by the following Formula (15).

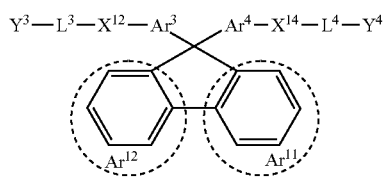

(15)

In Formula (15), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^3$ and $L^4$ each independently represent an alkylene group having 1 to 20 carbon atoms, in a case where $L^3$ and $L^4$ are an alkylene group having 2 to 20 carbon atoms, $L^3$ and $L^4$ may include a divalent linking group selected from the group having one or more selected from —O—, —S—, —CO—, and —NH— in the linking chain, $X^{12}$ and $X^{14}$ each independently represent a single bond, a phenylene group or a naphthylene group, and $Y^3$ and $Y^4$ each independently represent a polymerizable group having an ethylenically unsaturated bond.

$Ar^{11}$, $Ar^{12}$, $Ar^3$ and $Ar^4$ in Formula (15) have the same meaning as $Ar^1$ to $Ar^4$ in Formula (11), and their preferred ranges are also similar.

In Formula (15), preferably, at least one of $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent. More preferably, at least one of $Ar^3$ or $Ar^4$ is a benzothiazole ring, a tricyclic aromatic ring containing a benzothiazole ring, or a benzene ring or a naphthalene ring having a benzothiazolyl group as a substituent. Particularly preferably, $Ar^3$ is a benzothiazole ring, a tricyclic aromatic ring containing a benzothiazole ring, or a benzene ring or a naphthalene ring having a benzothiazolyl group as a substituent, and $X^{12}$ is a phenylene group or a naphthylene group, and/or $Ar^4$ is a benzothiazole ring, a tricyclic aromatic ring containing a benzothiazole ring, or a benzene ring or a naphthalene ring having a benzothiazolyl group as a substituent, and $X^{14}$ is a phenylene group or a naphthylene group.

$Ar^{11}$ and $Ar^{12}$ in Formula (15) is preferably a benzene ring or a naphthalene ring.

According to this aspect, it is possible to provide a curable composition exhibiting an excellent solvent solubility while maintaining a high refractive index.

$L^3$ and $L^4$ in Formula (15) have the same meaning as $L^3$ and $L^4$ in Formula (11), and their preferred ranges are also similar.

$Y^3$ and $Y^4$ in Formula (15) have the same meaning as $Y^3$ and $Y^4$ in Formula (11), and their preferred ranges are also similar.

Hereinafter, specific examples of the compound represented by Formula (1), which was preferably used in the present invention, was listed, but the present invention is not limited to the following compounds. In addition, the compounds shown in the following specific examples also belong to the compounds of the present invention.

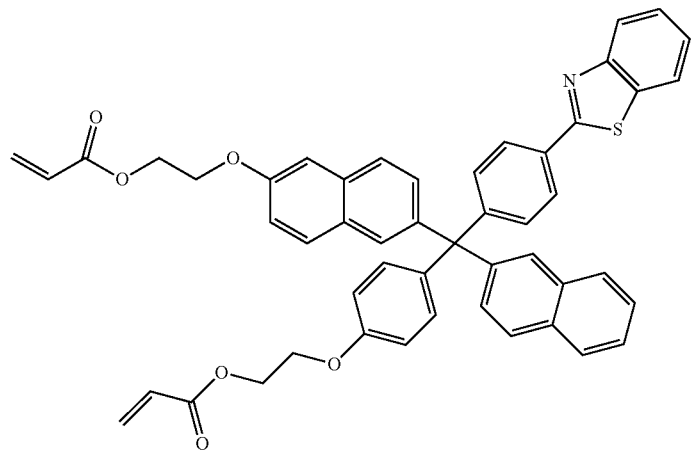
(1-1)
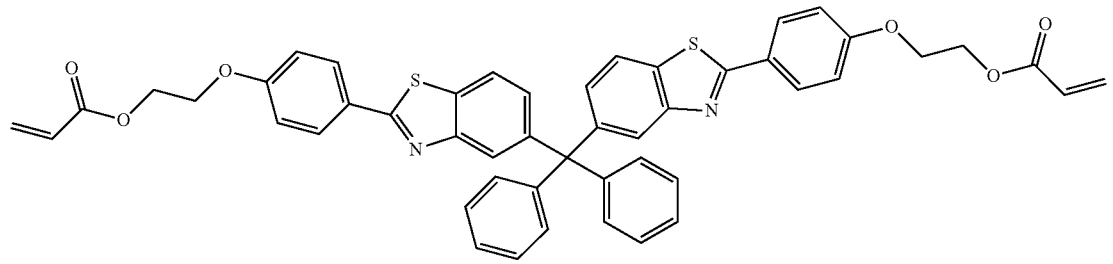
(1-2)
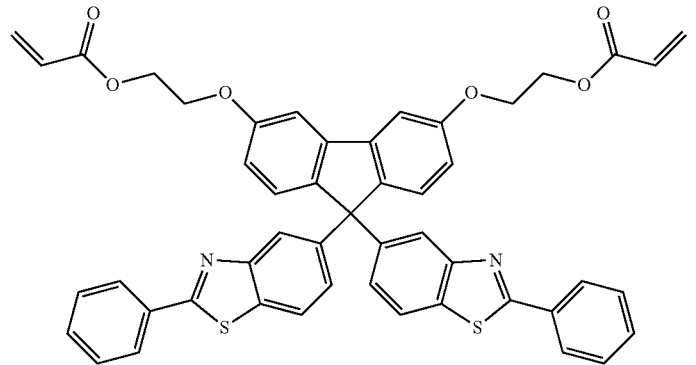
(1-3)
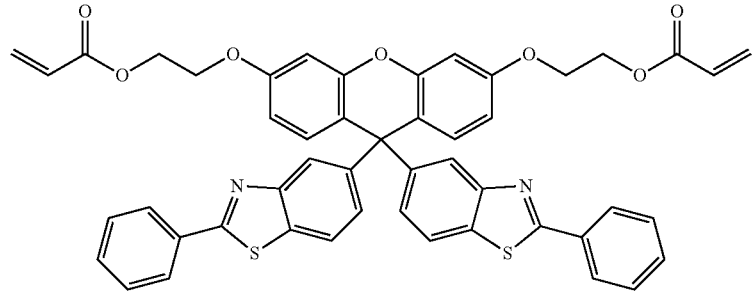
(1-4)

-continued
(1-5)
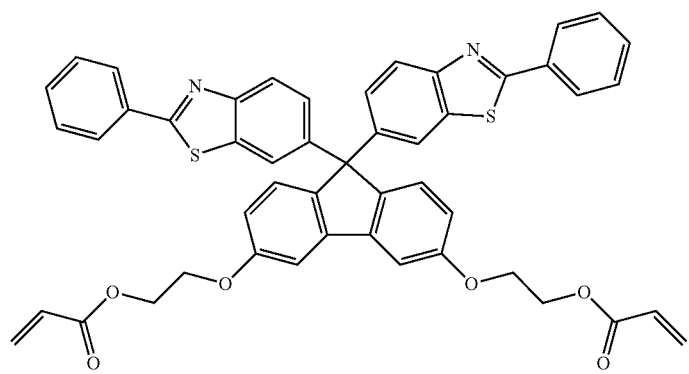
(1-6)
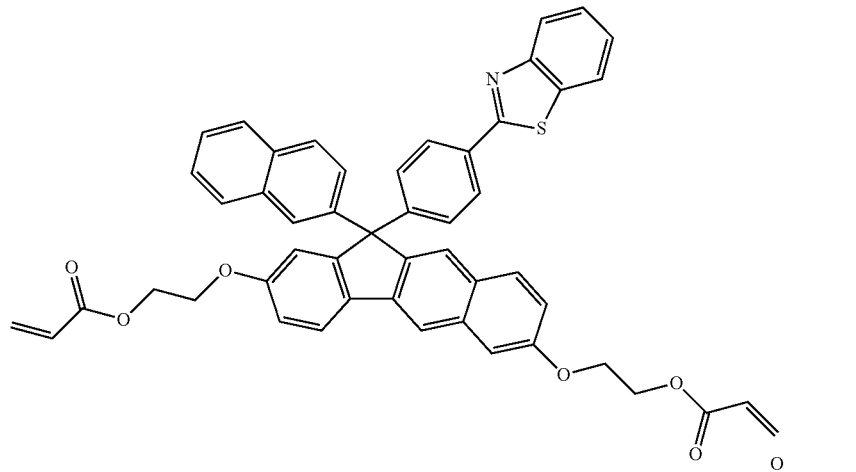
(1-7)
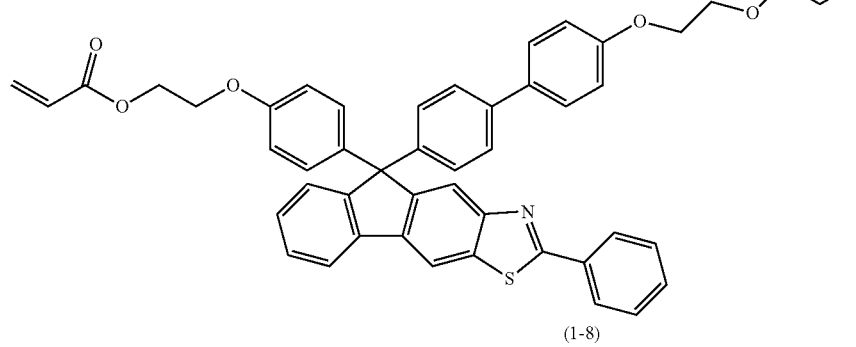
(1-8)
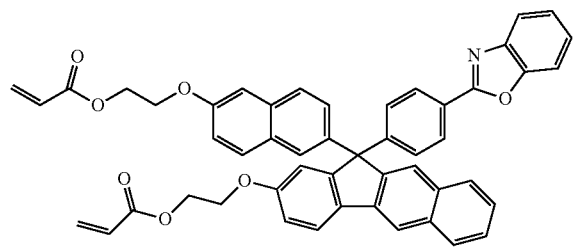
(1-9)
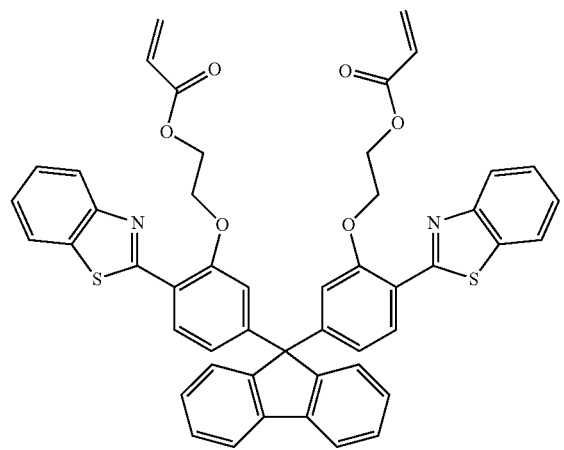

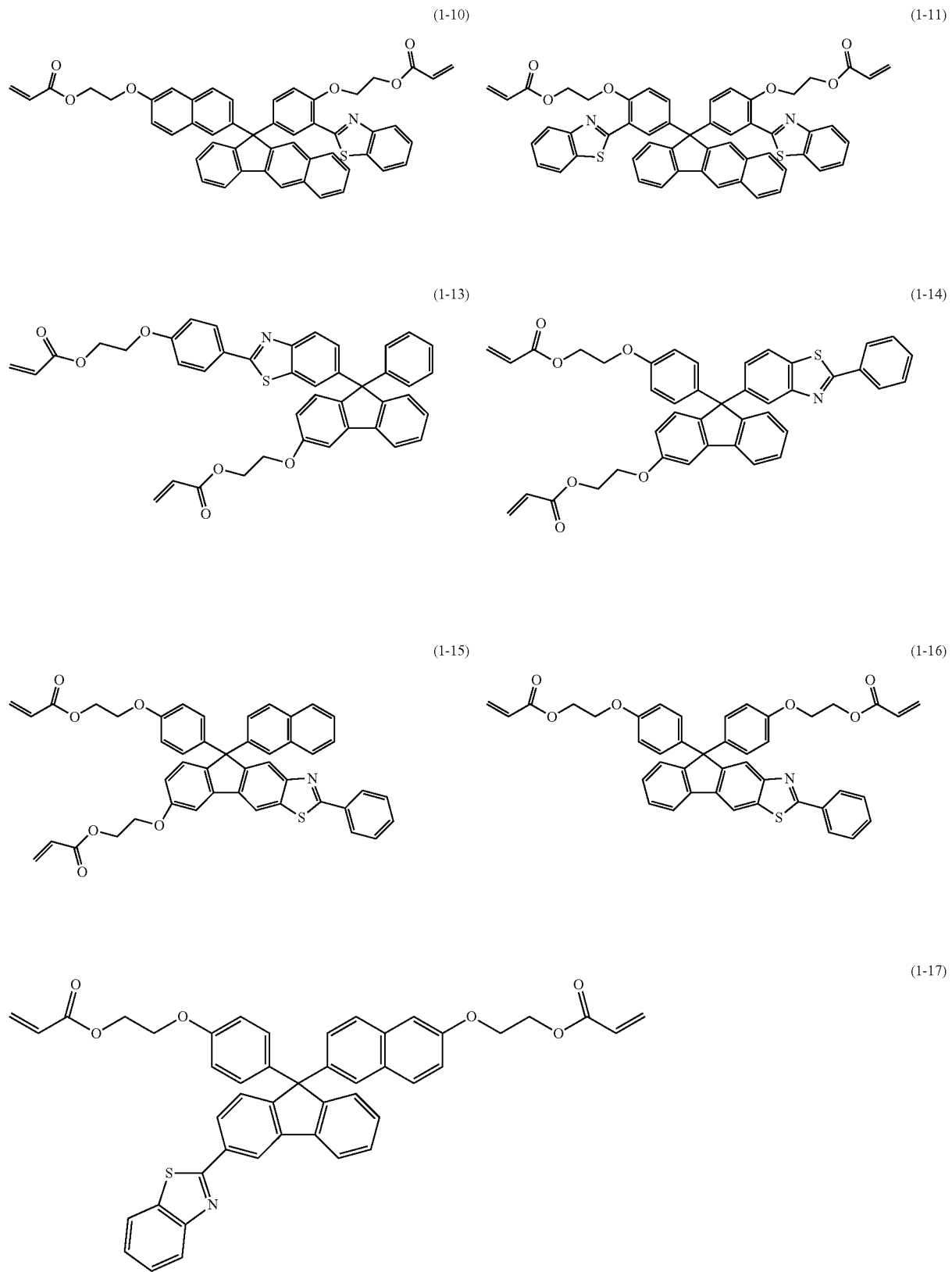

-continued
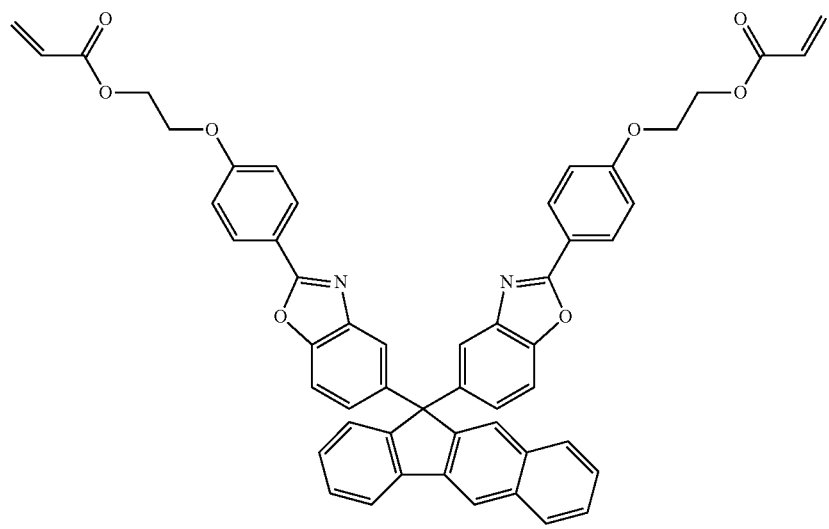
(1-18)
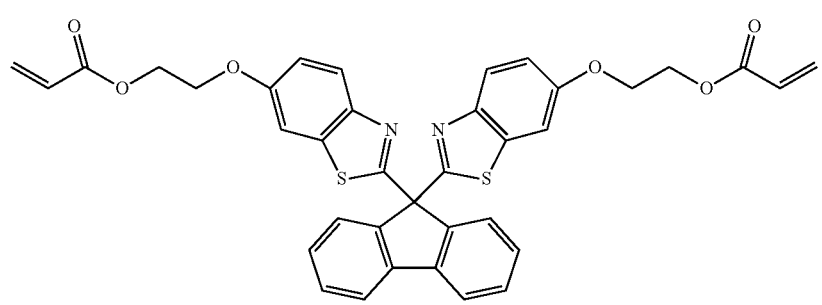
(1-19)
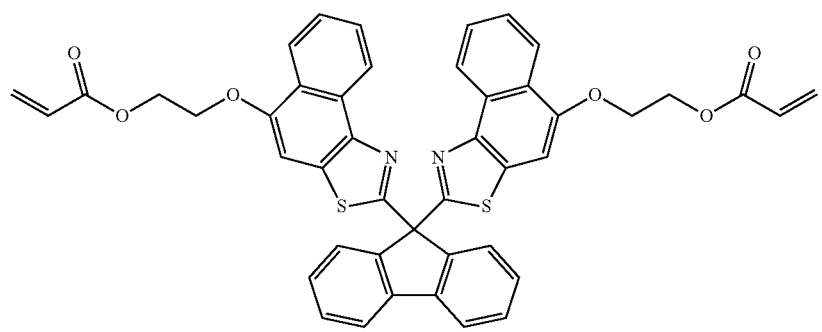
(1-20)
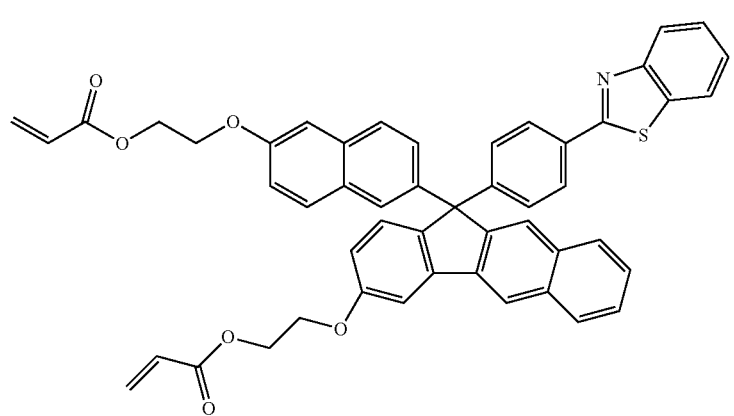
(1-21)

(1-22)
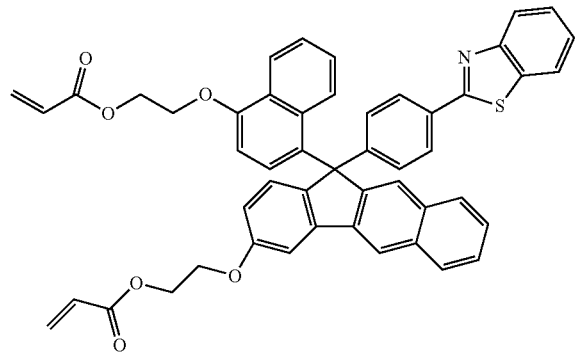
(1-23)
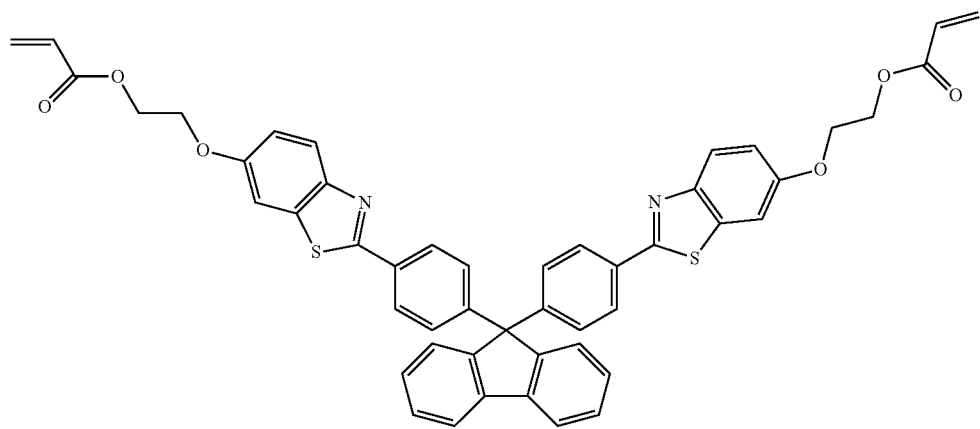
(1-24)
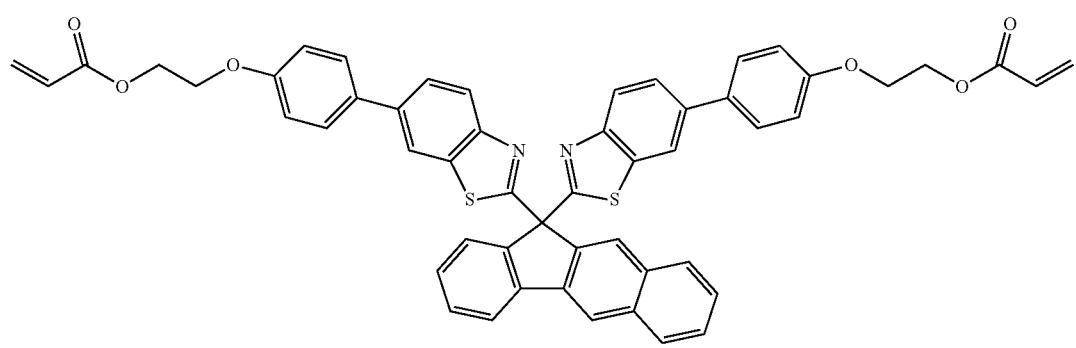
(1-25)
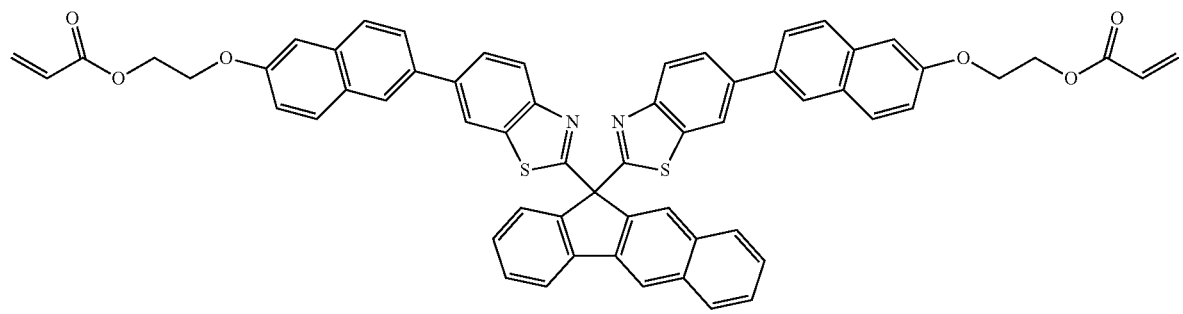

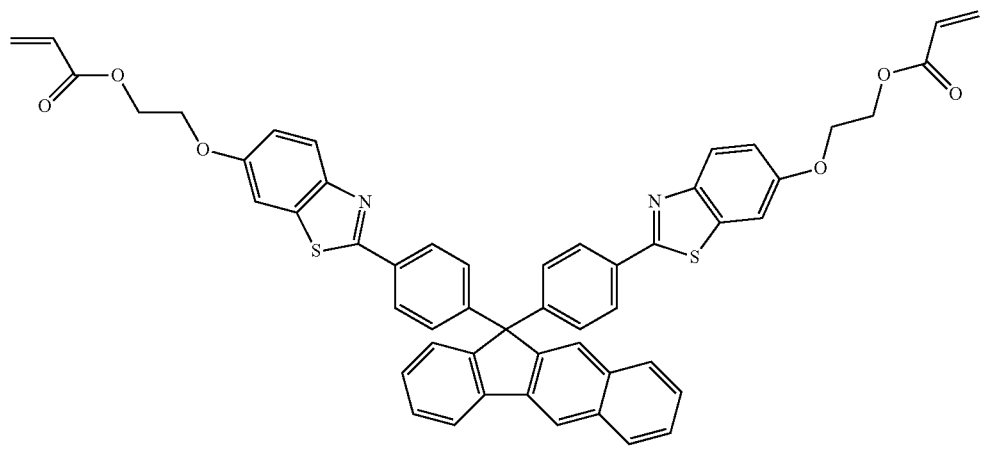
(1-26)
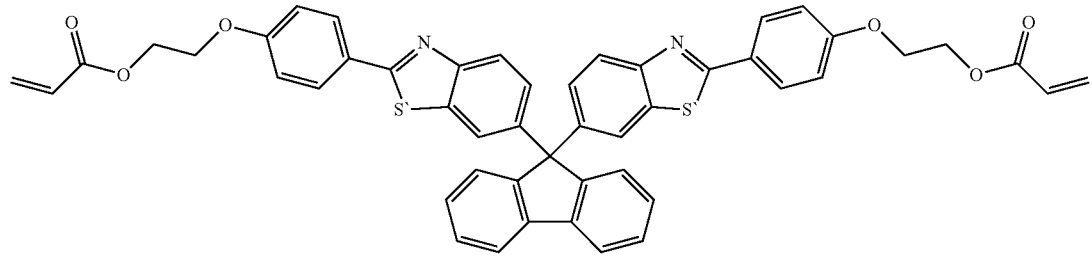
(1-27)
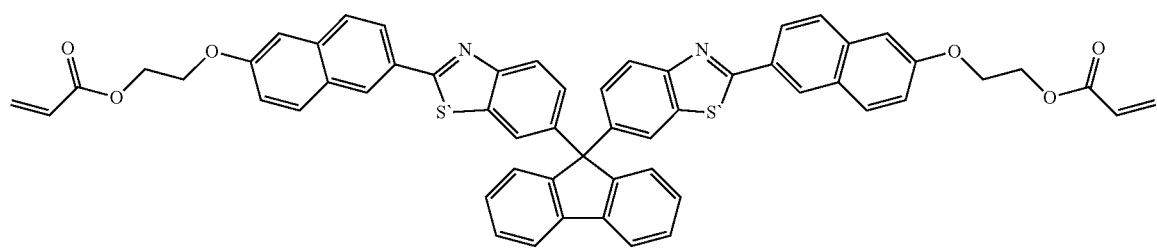
(1-28)
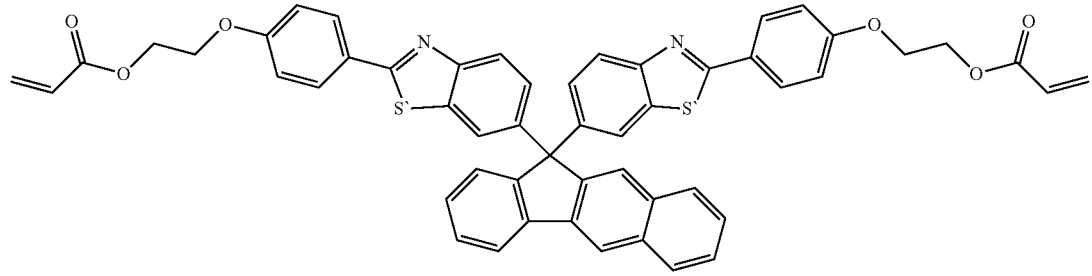
(1-29)
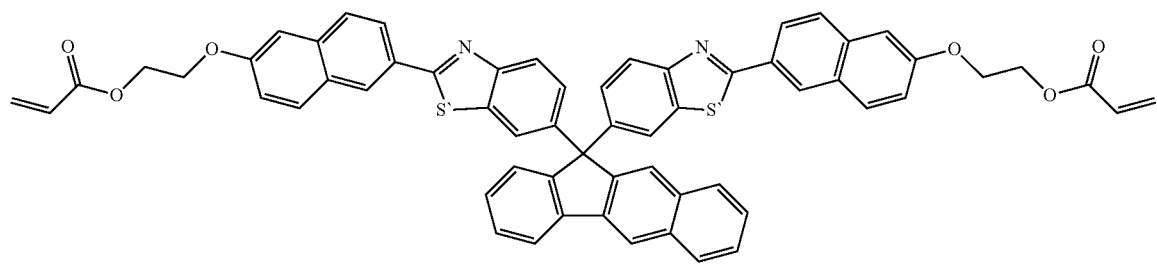
(1-30)

(1-31)
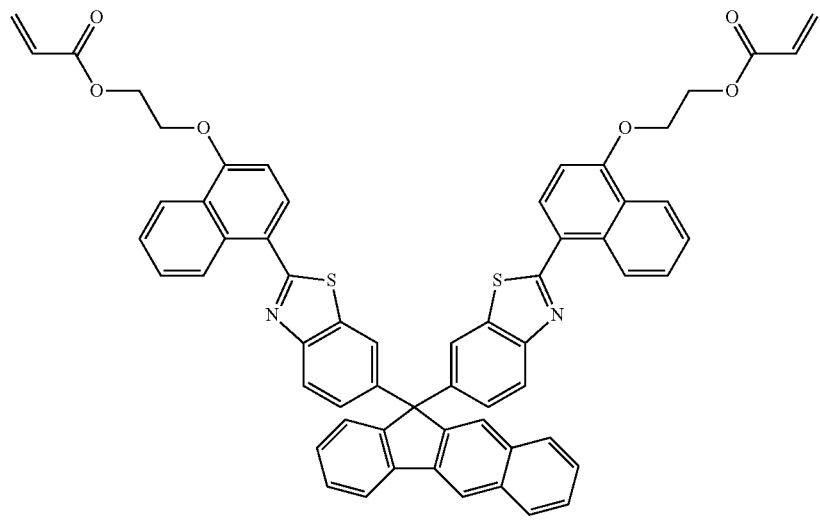
(1-32)
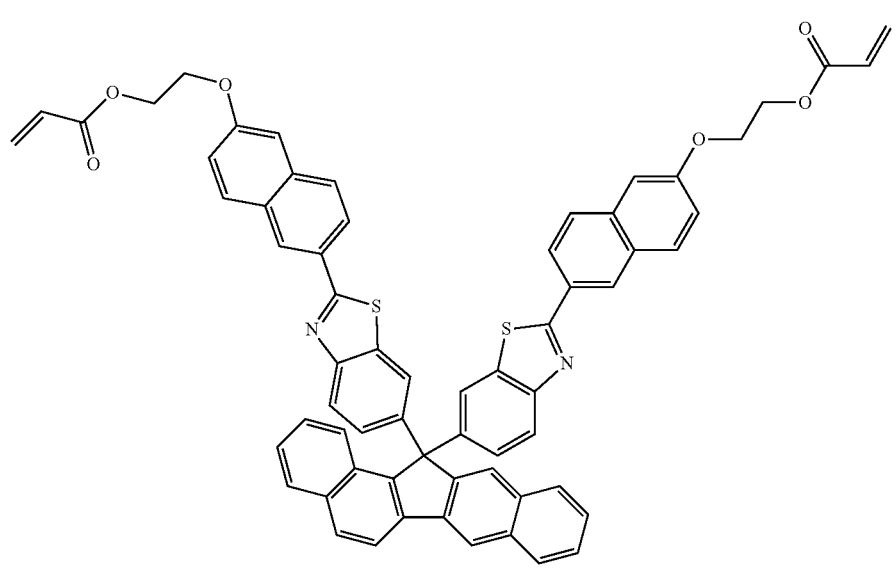
(1-33)
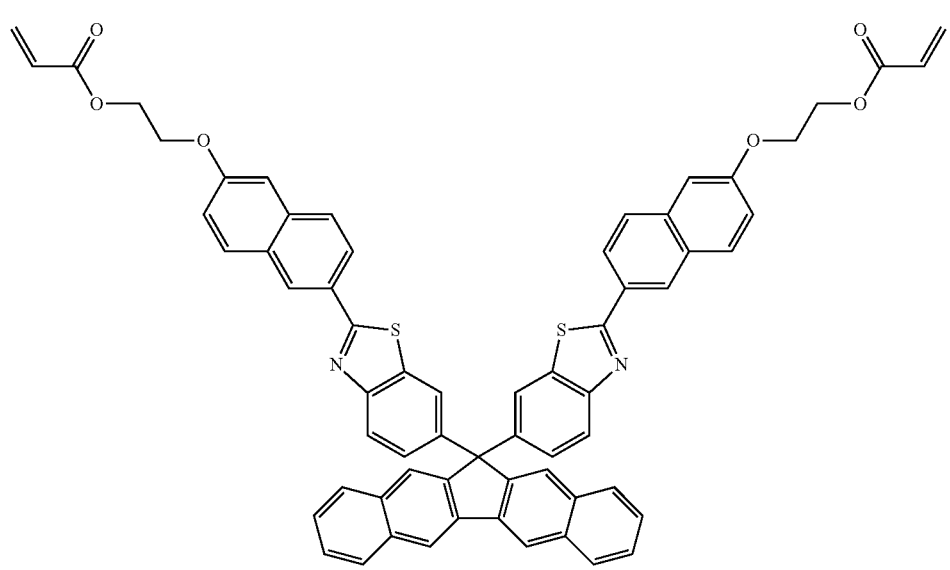

-continued
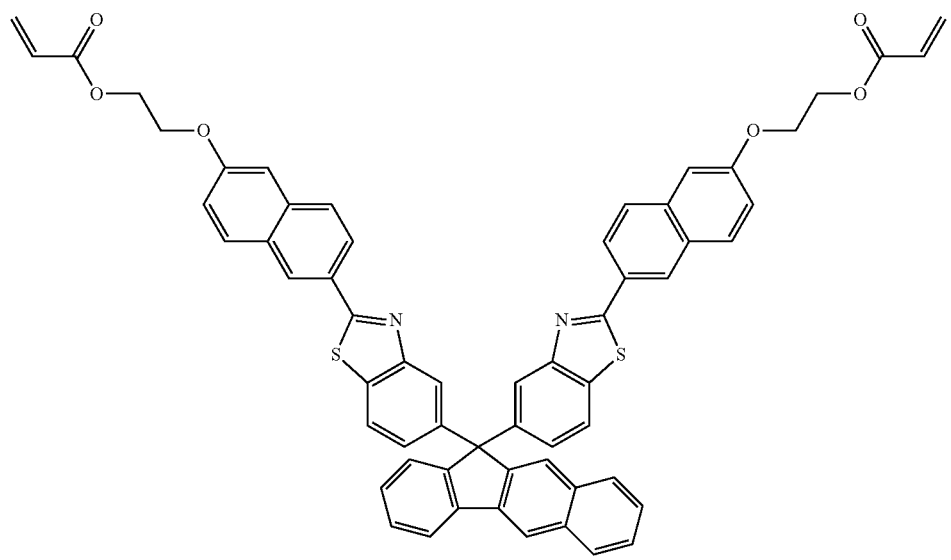
(1-34)
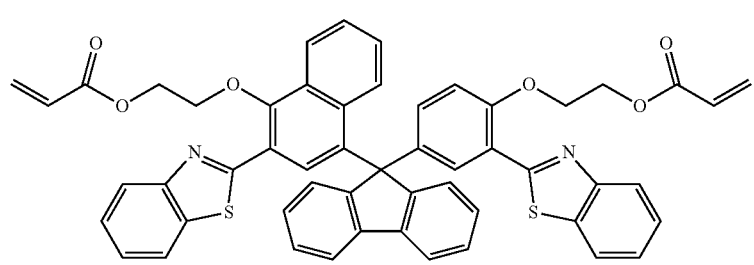
(1-35)
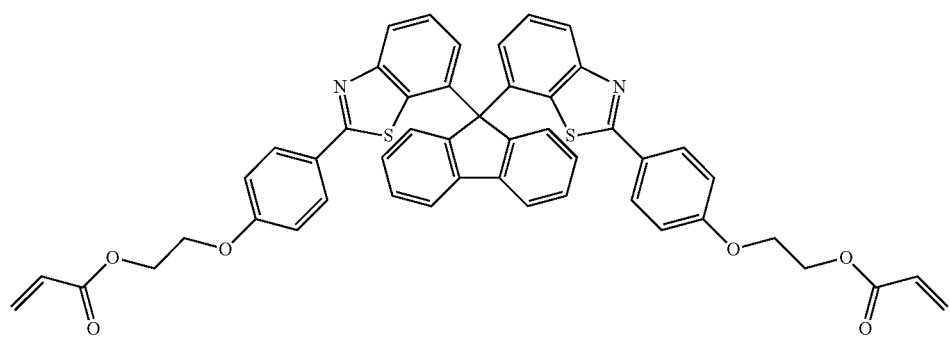
(1-36)
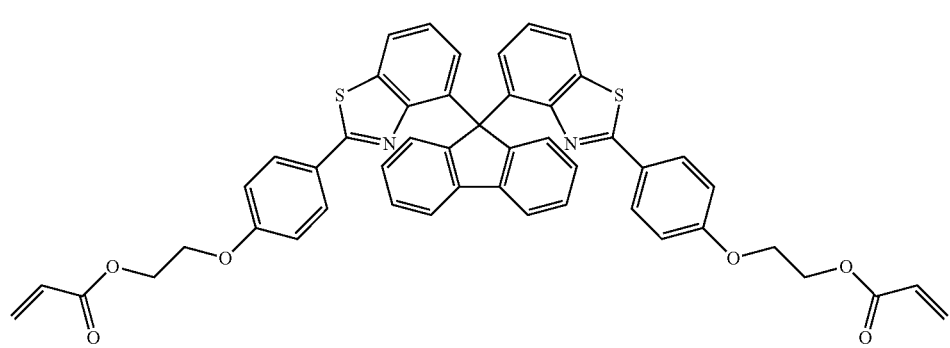
(1-37)

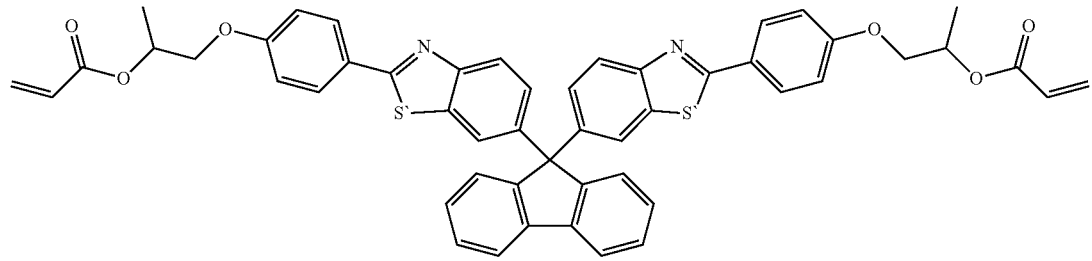
(1-38)
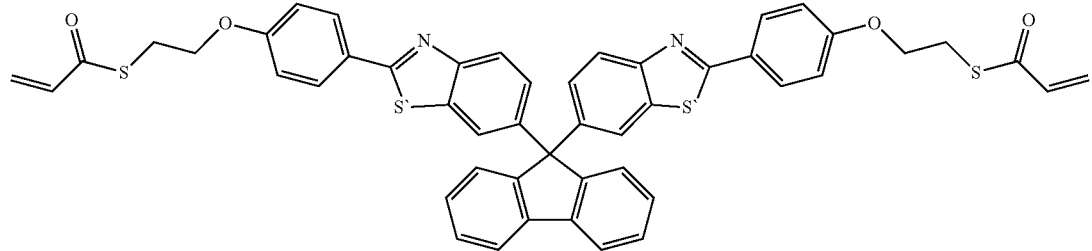
(1-39)
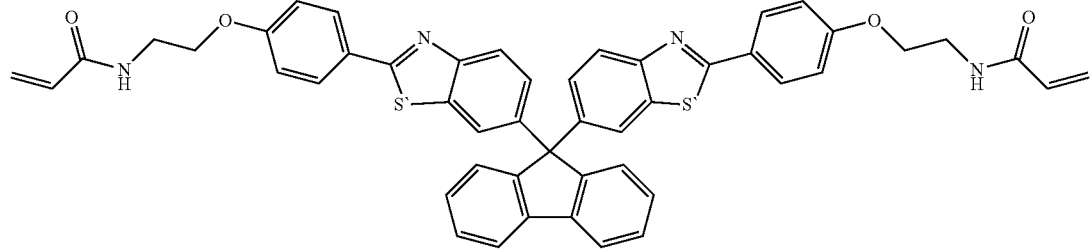
(1-40)
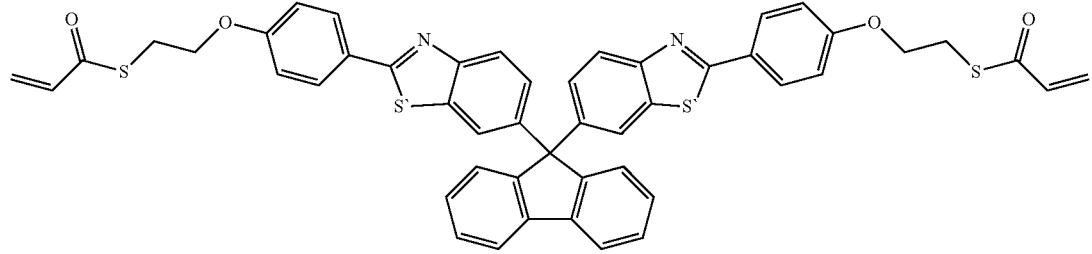
(1-41)
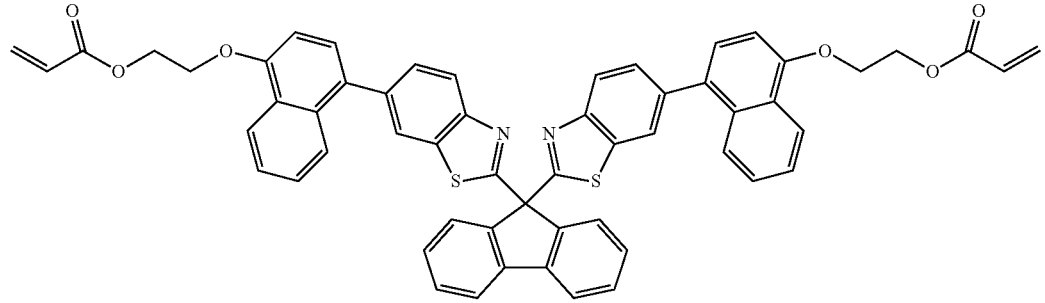
(1-42)
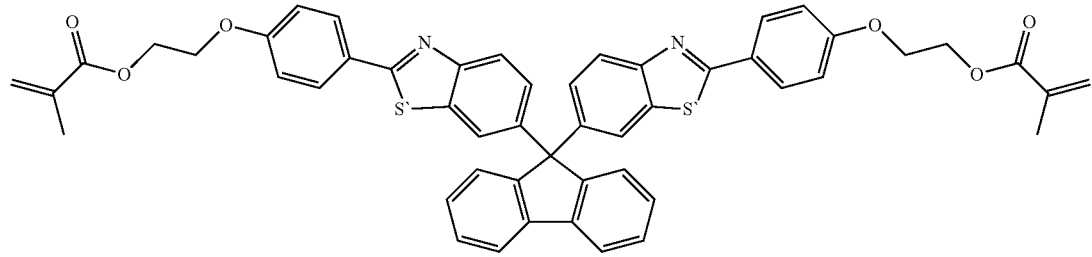
(1-43)

(1-44)
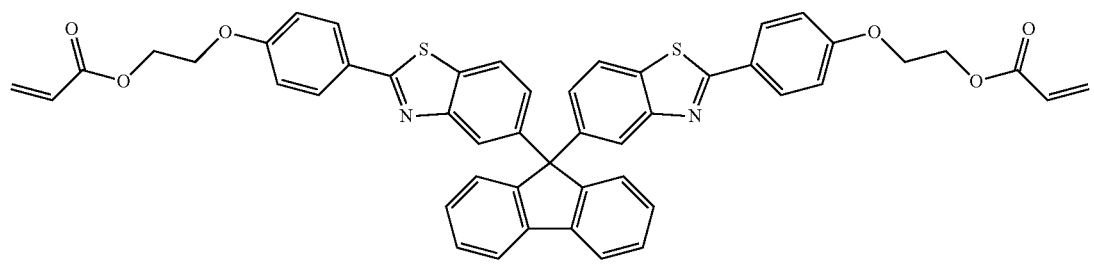
(1-45)
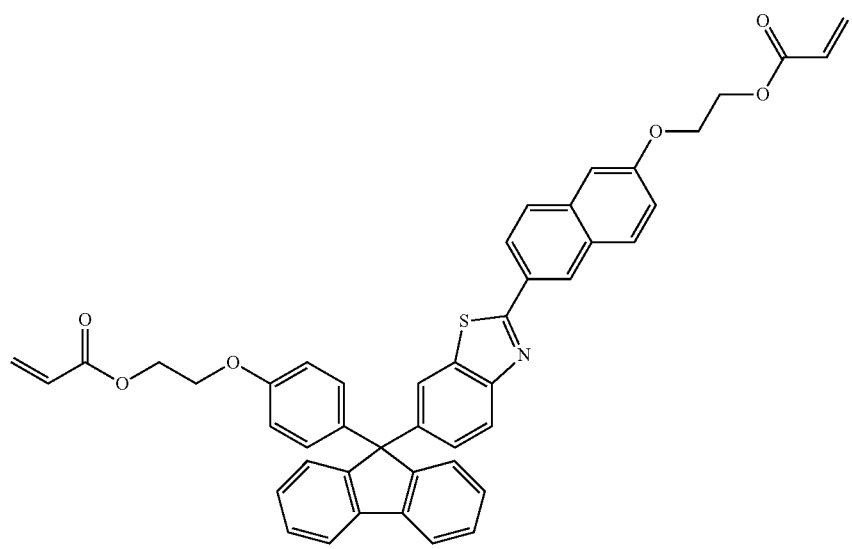
(1-46)
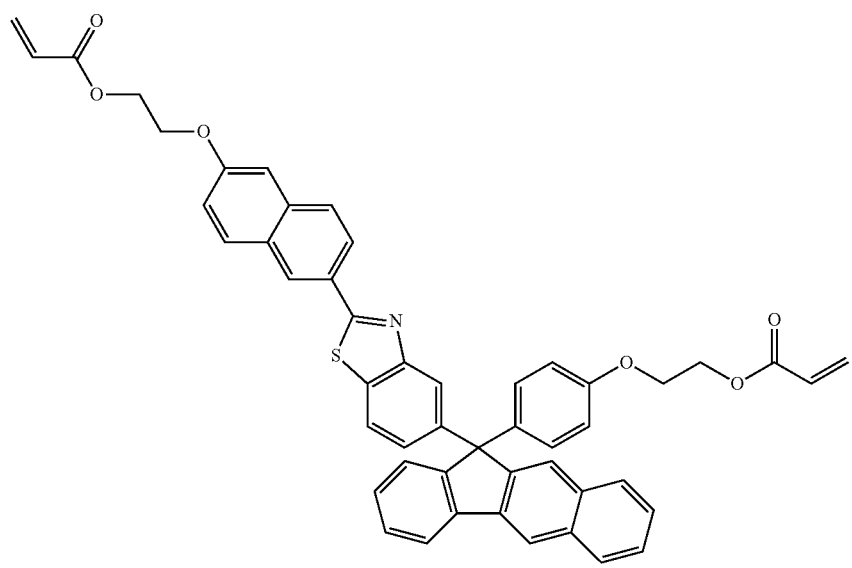

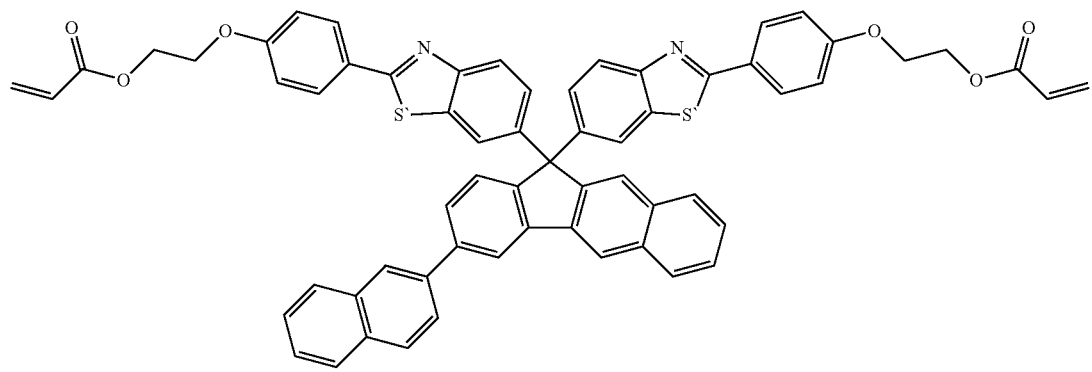
(1-47)
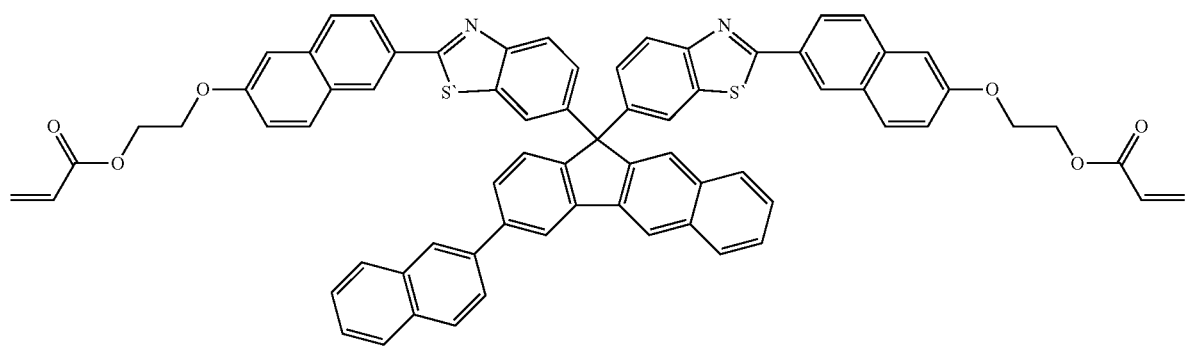
(1-48)
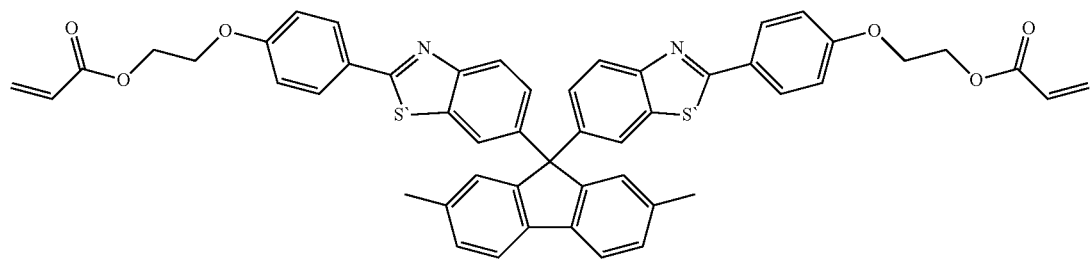
(1-49)
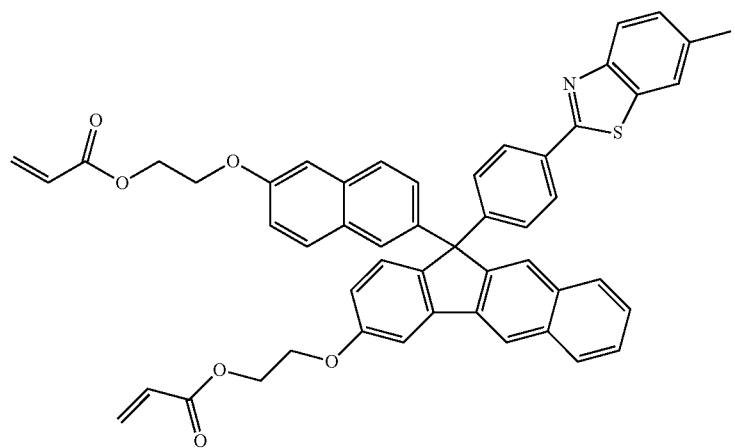
(1-50)

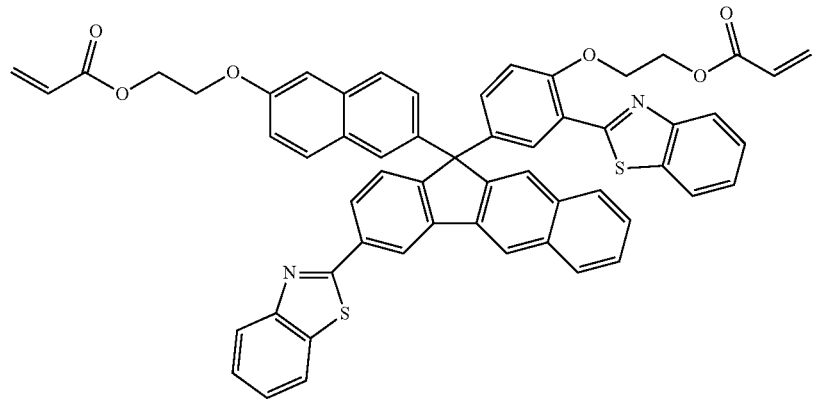

(1-51)

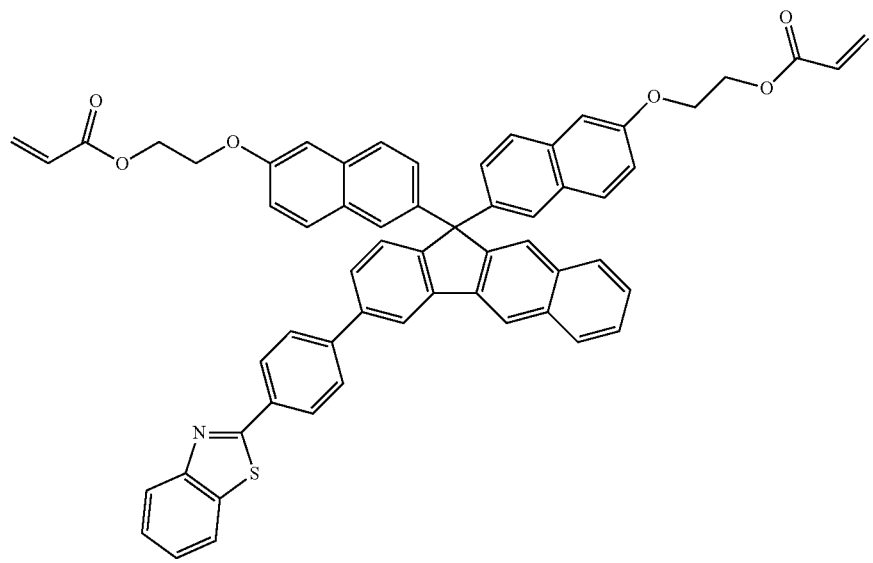

(1-52)

As the compound represented by Formula (1), the above compounds (1-9) to (1-51) are preferable, the compounds (1-9) to (1-11), (1-19) to (1-51) are more preferable, and the compounds (1-10), (1-19), (1-21) to (1-30), (1-46) to (1-48) are particularly preferable.

The content of the compound represented by Formula (1) in the curable composition of the present invention differs depending on the application. For example, the content of the compound is preferably 10% by mass to 99% by mass and more preferably 15% by mass to 99% by mass relative to the total solid content of the curable composition.

<<Thermal Radical Polymerization Initiator/Photo Radical Polymerization Initiator>>

The curable composition of the present invention contains at least one kind selected from thermal radical polymerization initiators and photo radical polymerization initiators. In the present invention, by including at least one kind selected from thermal radical polymerization initiators and photo radical polymerization initiators, the cured material having a high refractive index can be easily produced in a good moldability.

<<<Photo Radical Polymerization Initiator>>>

The photo radical polymerization initiator is not particularly limited, and it may be a known photo radical polymerization initiator. For example, the following compounds can be used: bis(2,6-dimethoxybenzoyl)-2,4,4-trimethyl pentyl phosphine oxide, bis(2,6-dimethylbenzoyl)-2,4,4-trimethyl pentyl phosphine oxide, bis(2,4,6-trimethylbenzoyl)-2,4,4-trimethyl pentyl phosphine oxide, bis(2,6-dichlorobenzoyl)-2,4,4-trimethyl pentyl phosphine oxide, 1-phenyl-2-hydroxy-2-methylpropan-1-one, 1-hydroxy cyclohexyl phenyl ketone, 1-(4-isopropylphenyl)-2-hydroxy-2-methylpropan-1-one, 1,2-diphenylethanedione, methyl phenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl] phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)-butanone-1,2,4,6-trimethyl benzoyl-diphenyl-phosphine oxide, bis(2,4,6-trimethylbenzoyl)-phenyl phosphine oxide. Among them, IRGACURE 184 (1-hydroxy cyclohexyl phenyl ketone) (manufactured by BASF Corp.), 1-[4-(2-hydroxyethoxy)-phenyl]-2-hydroxy-2-methyl-1-propan-1-one, 2-methyl-1-(4-methylthiophenyl)-2-morpholinopropan-1-one, or 2,2-dimethoxy-1,2-diphenylethan-1-one can be preferably used as a photo radical polymerization initiator of the present invention.

The content of the photo radical polymerization initiator is not particularly limited, but it is preferably 0.01% by mass to 5% by mass, more preferably 0.05% by mass to 1.0% by mass, and particularly preferably 0.05% by mass to 0.5% by mass with respect to the mass of the compound represented by Formula (1).

<<<Thermal Radical Polymerization Initiator>>>

The thermal radical polymerization initiator is not particularly limited, and it may be a known thermal radical polymerization initiator. For example, the following compounds can be used: 1,1-di(t-hexylperoxy) cyclohexane, 1,1-di(t-butylperoxy) cyclohexane, 2,2-di(4,4-di-(t-butylperoxy) cyclohexyl) propane, t-hexylperoxy isopropyl monocarbonate, t-butylperoxy-3,5,5-trimethyl hexanoate, t-butylperoxy laurate, dicumyl peroxide, di-t-butyl peroxide, t-butylperoxy-2-ethyl hexanoate, t-hexylperoxy-2-ethyl hexanoate, cumene hydroperoxide, t-butylhydroperoxide, 2,3-dimethyl-2,3-diphenyl butane.

As the thermal radical polymerization initiator of the present invention, a hydroperoxide-based thermal radical polymerization initiator having hydroperoxide groups in the molecule is preferable. Furthermore, it is more preferable to use at least one kind of hydroperoxide-based thermal radical polymerization initiators having hydroperoxide group in the molecule and non-hydroperoxide-based thermal radical polymerization initiators not having hydroperoxide groups in the molecule.

In addition, as the thermal radical polymerization initiator of the present invention, PERBUTYL O (t-butylperoxy-2-ethyl hexanoate) manufactured by NOF Corporation as a non-hydroperoxide-based thermal radical polymerization initiator and PERCUMYL H (cumene hydroperoxide) manufactured by NOF Corporation as a hydroperoxide-based thermal radical polymerization initiator can be preferably used.

It is preferable to use a hydroperoxide-based thermal radical polymerization initiator having hydroperoxide groups in the molecule as a thermal radical polymerization initiator, the reason is that the hydroperoxide-based thermal radical polymerization initiator has an effect of promoting chain transfer of non-conjugated vinylidene group-containing compound monomer during the polymerization and it may be possible to impart deformability of the semi-cured material due to more improved control performance of the three-dimensional structure. Further, in a hydroperoxide-based thermal radical polymerization initiator, since the temperature to initiate the thermal radical polymerization is generally high, it is more preferable to use a non-hydroperoxide-based thermal radical polymerization initiator having a low thermal polymerization initiation temperature together.

The content of the thermal radical polymerization initiator is not particularly limited, but it is preferably 0.01% by mass to 5.0% by mass, more preferably 0.1% by mass to 4.0% by mass, and particularly preferably 0.3% by mass to 3.0% by mass with respect to the mass of the compound represented by Formula (1).

<<<Monofunctional (Meth)Acrylate Monomer>>>

The curable composition of the present invention may include a monofunctional (meth)acrylate monomer other than the compound of Formula (1).

As a monofunctional (meth)acrylate monomer, for example, the following compounds can be used: adamantyl (meth)acrylates such as 1-adamantyl (meth)acrylate, norbornyl (meth)acrylates such as isobornyl (meth)acrylate, tricyclodecane(meth)acrylates such as tricycle [5,2,1,0$^{2,6}$] deca-8-yl acrylate, 2-ethyl-2-butylpropanediol(meth)acrylate, 2-ethylhexyl (meth)acrylate, 2-ethylhexyl carbitol (meth)acrylate, 2-hydroxybutyl (meth)acrylate, 2-hydroxyethyl (meth)acrylate, 2-hydroxypropyl (meth)acrylate, 2-methoxy ethyl (meth)acrylate, 3-methoxy-butyl (meth)acrylate, 4-hydroxybutyl (meth)acrylate, benzyl (meth)acrylate, 1- or 2-naphthyl (meth)acrylate, butanediol mono(meth)acrylate, butoxyethyl (meth)acrylate, butyl (meth)acrylate, cetyl (meth)acrylate, EO-modified cresol(meth)acrylate, dipropylene glycol (meth)acrylate, ethoxylated phenyl (meth)acrylate, ethyl (meth)acrylate, isoamyl (meth)acrylate, isobutyl (meth)acrylate, isooctyl (meth)acrylate, cyclohexyl (meth)acrylate, dicyclopentanyl(meth)acrylate, dicyclopentanyloxy ethyl (meth)acrylate, isomyristyryl (meth)acrylate, lauryl (meth)acrylate, methoxydipropylene glycol (meth)acrylate, methoxytripropylene glycol (meth)acrylate, methoxypolyethylene glycol (meth)acrylate, methoxytriethylene glycol (meth)acrylate, methyl (meth)acrylate, neopentyl glycol benzoate (meth)acrylate, nonylphenoxypolyethylene glycol (meth)acrylate, nonylphenoxypolypropylene glycol (meth)acrylate, octyl (meth)acrylate, paracumylphenoxyethylene glycol (meth)acrylate, ECH-modified phenoxy(meth)acrylate, phenoxyethyl (meth)acrylate, phenoxydiethylene glycol (meth)acrylate, phenoxyhexaethylene glycol (meth)acrylate, phenoxytetraethylene glycol (meth)acrylate, stearyl (meth)acrylate, EO-modified succinic acid (meth)acrylate, tert-butyl (meth)acrylate, tribromophenyl (meth)acrylate, EO-modified tribromophenyl (meth)acrylate, or tridodecyl (meth)acrylate.

The curable composition of the present invention preferably contains a monofunctional (meth)acrylate monomer having an aromatic ring, among monofunctional (meth)acrylate monomers.

As a monofunctional (meth)acrylate monomer having an aromatic ring, for example, the following compounds can be preferably used: benzyl (meth)acrylate, 1- or 2-naphthyl (meth)acrylate, EO-modified cresol (meth)acrylate, ethoxylated phenyl (meth)acrylate, nonylphenoxypolyethylene glycol (meth)acrylate, nonylphenoxypolypropylene glycol (meth)acrylate, paracumylphenoxyethylene glycol (meth)acrylate, ECH-modified phenoxy(meth)acrylate, phenoxyethyl (meth)acrylate, phenoxydiethylene glycol (meth)acrylate, phenoxyhexaethylene glycol (meth)acrylate, phenoxytetraethylene glycol (meth)acrylate, tribromophenyl (meth)acrylate, EO-modified tribromophenyl (meth)acrylate, O-phenylphenol (meth)acrylate, or O-phenylphenol EO-modified (meth)acrylate.

Among them, benzyl (meth)acrylate, phenoxyethyl (meth)acrylate, O-phenylphenol (meth)acrylate, O-phenylphenol EO-modified (meth)acrylate is more preferable, benzyl (meth)acrylate and phenoxyethyl (meth)acrylate are particularly preferable, and benzyl acrylate and phenoxyethyl acrylate are more particularly preferable.

The curable composition of the present invention may not contain a monofunctional (meth)acrylate monomer, but in a case where the composition is used to form an optical component, the composition preferably contains a monofunctional (meth)acrylate monomer.

In a case where a monofunctional (meth)acrylate monomer is included in the compositions of the present invention, the monomer is preferably 10% by mass to 200% by mass and more preferably 20% by mass to 160% by mass with respect to the mass of the compound represented by Formula (1).

<<<<Non-Conjugated Vinylidene Group-Containing Compound>>>>

The curable composition of the present invention may contain a non-conjugated vinylidene group-containing compound. In the present invention, the non-conjugated vinylidene group-containing compound can adjust curing rate at the time of curing of the curable composition and can obtain a more uniform thickness of the cured material. Thus, it is possible to improve the heat resistance and the yield rate of the cured material.

As a non-conjugated vinylidene group-containing compound, compounds described in paragraphs "0016" to "0034" of JP2012-107191A can be used, and the contents are incorporated in the present specification.

The curable composition of the present invention may contain a non-conjugated vinylidene group-containing compound, but in a case where the composition contains a non-conjugated vinylidene group-containing compound, the compound is preferably 0.5% by mass to 30% by mass, more preferably 1% by mass to 25% by mass, and particularly preferably 2% by mass to 20% by mass with respect to the total solid content of the curable composition.

<<<Polymer Having a Polymerizable Group in a Side Chain>>>

The curable composition of the present invention may further contain a polymer having a polymerizable group in a side chain. This enables the curable composition to adjust its viscosity. The polymer having a polymerizable group in a side chain may be a homopolymer by polymerizing one kind of monomers or copolymers obtained by copolymerizing two kinds or more of monomers. In the case of the copolymer, at least one monomer may have a polymerizable group in a side chain.

Specific examples of the polymer having a polymerizable group in a side chain are listed as follows. Further, Ra and Rb each independently represent a hydrogen or an alkyl group.

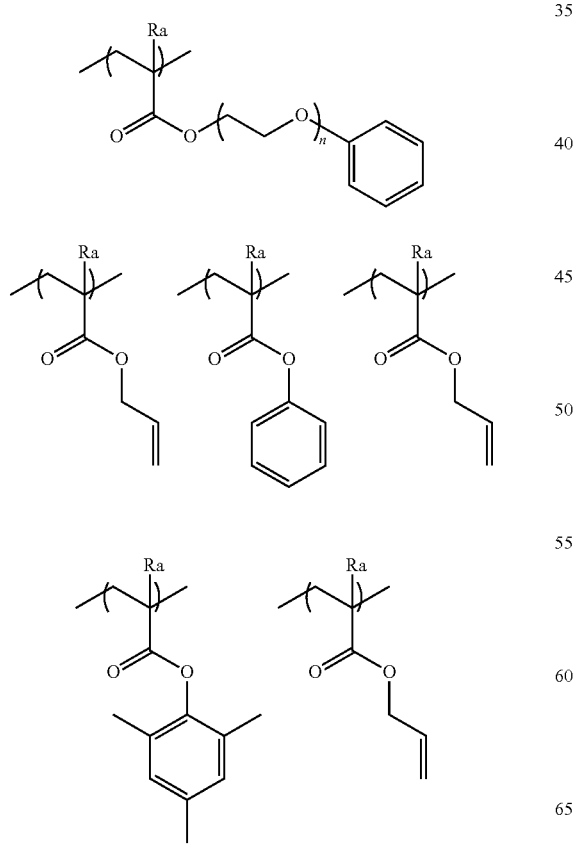

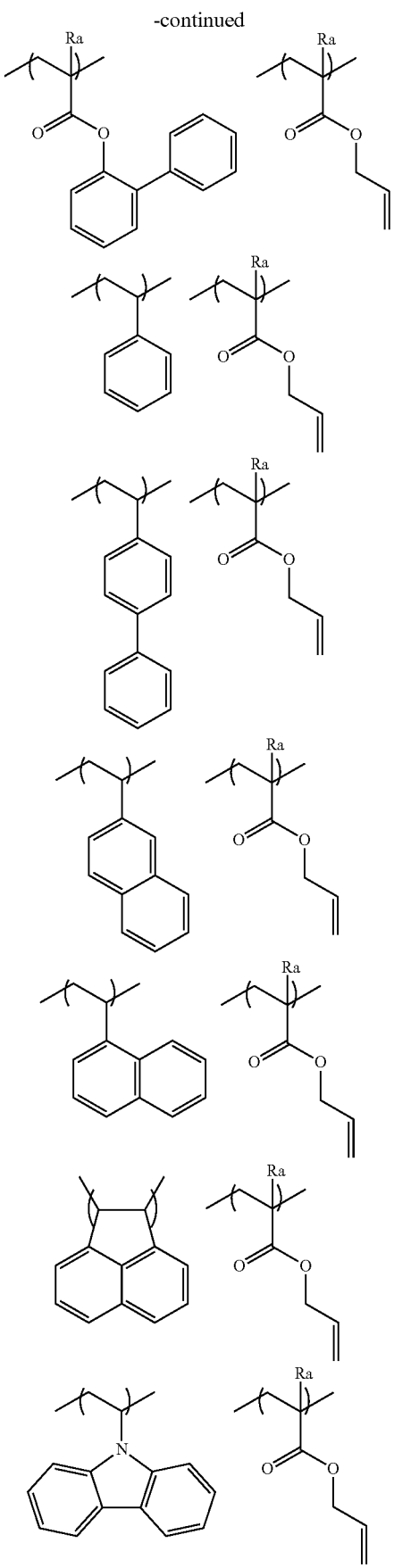

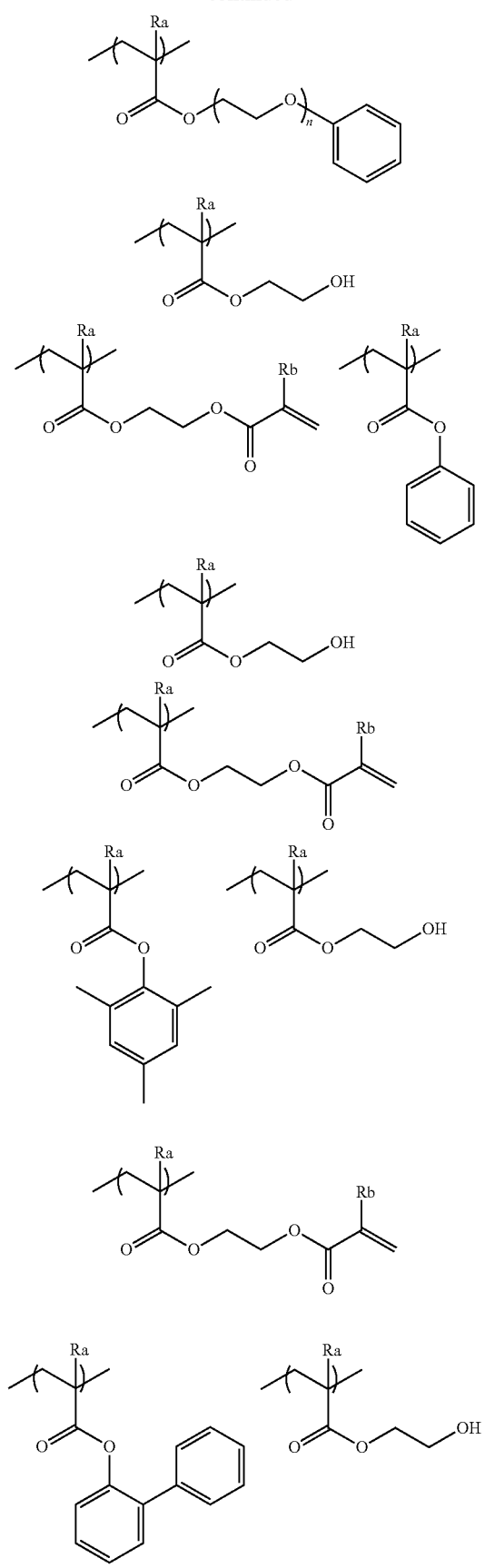
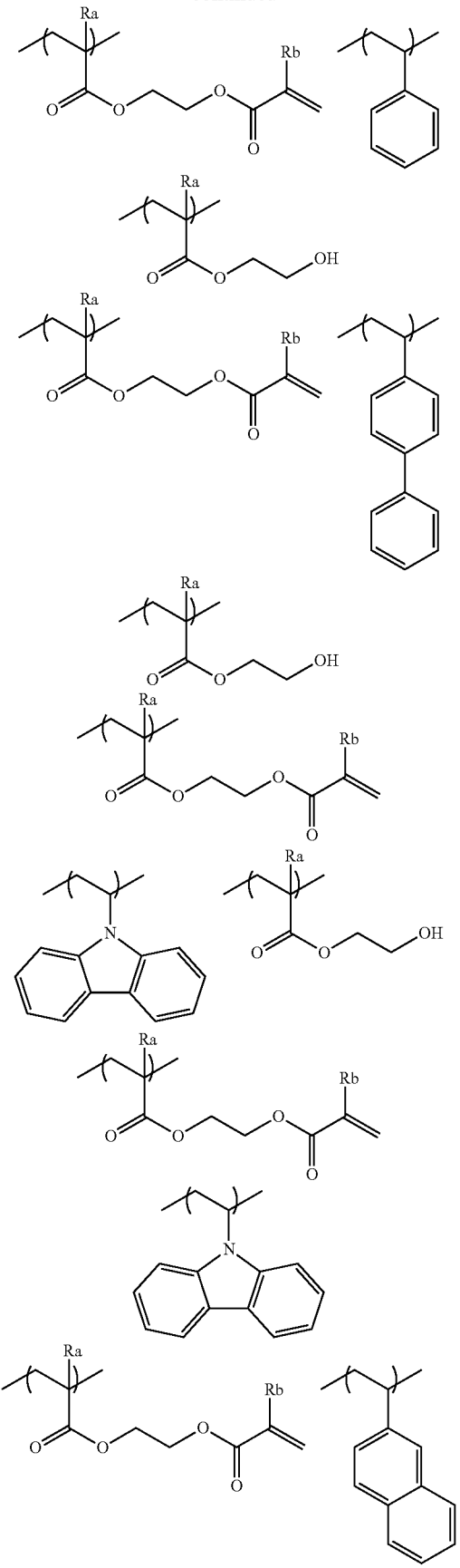

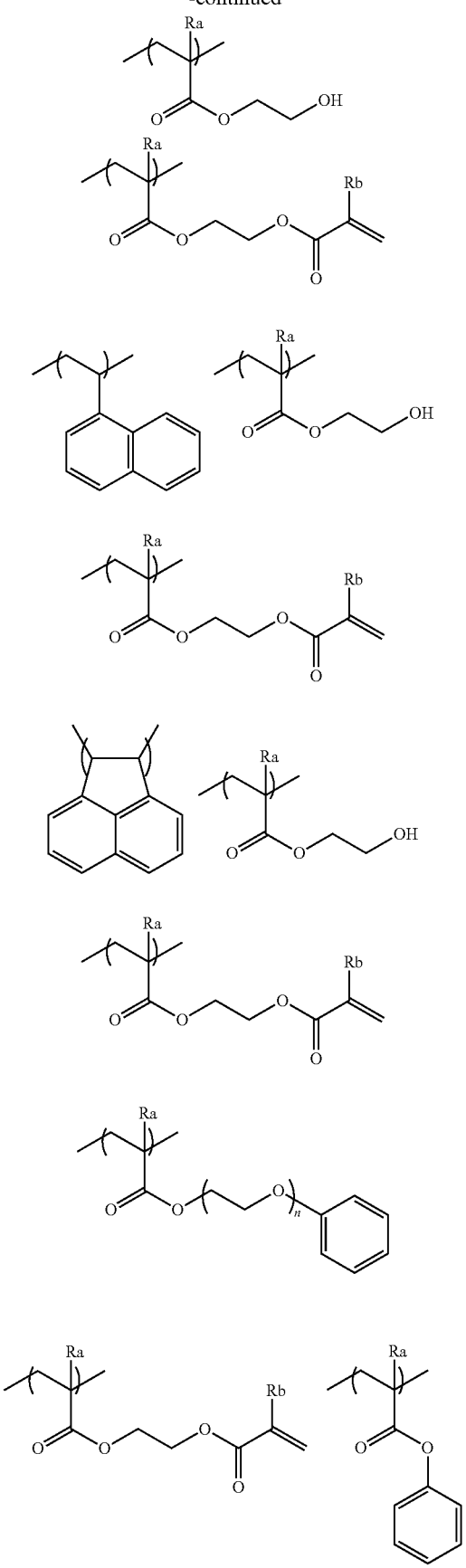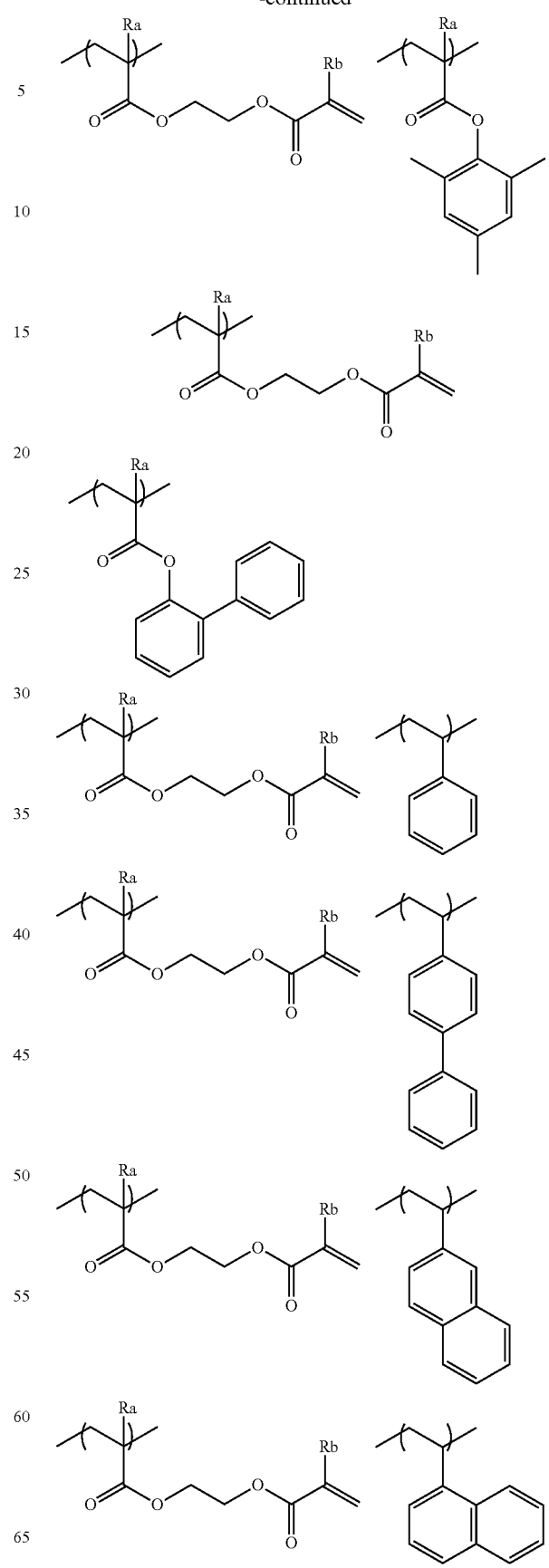

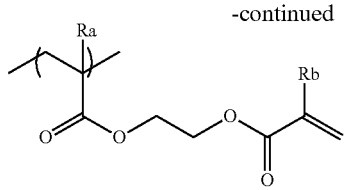

The molecular weight of the polymer having a polymerizable group in a side chain is preferably 1,000 to 10,000,000, more preferably 5,000 to 300,000 and particularly preferably 10,000 to 200,000.

The glass-transition temperature (hereinafter, also referred to as Tg) of the polymer having a polymerizable group in a side chain is preferably 50° C. to 400° C., more preferably 70° C. to 350° C., and particularly preferably 100° C. to 300° C.

The curable composition of the present invention may not have a polymer having a polymerizable group in a side chain, but in a case where the composition contains a polymer having a polymerizable group in a side chain, the polymer is preferably 1% by mass to 90% by mass, more preferably 2% by mass to 80% by mass, and particularly preferably 5% by mass to 60% by mass with respect to the total solid content of the curable composition.

<<<Solvent>>>

The curable composition of the present invention may have a solvent. The solvent is not particularly limited as long as it does not impair the compatibility with components of the curable composition such as the compound represented by the above described Formula (1). The solvent may be arbitrarily selected and used alone, or may also be used in combination of plural kinds.

Specific examples of the solvent include toluene, p-xylene, o-xylene, m-xylene, ethylbenzene, styrene, ethylene glycol dimethyl ether, propylene glycol monomethyl ether, ethylene glycol monomethyl ether, propylene glycol, propylene glycol monoethyl ether, ethylene glycol monoethyl ether, ethylene glycol monoisopropyl ether, ethylene glycol methyl ether acetate, propylene glycol monomethyl ether acetate, ethylene glycol ethyl ether acetate, diethylene glycol dimethyl ether, propylene glycol mono-butyl ether, ethylene glycol monobutyl ether, diethylene glycol diethyl ether, dipropylene glycol monomethyl ether, diethylene glycol monomethyl ether, dipropylene glycol monoethyl ether, diethylene glycol monoethyl ether, triethylene glycol dimethyl ether, and diethylene glycol monoethyl ether acetate, diethylene glycol, 1-octanol, ethylene glycol, hexylene glycol, trimethylene glycol, 1-methoxy-2-butanol, cyclohexanol, diacetone alcohol, furfuryl alcohol, tetrahydrofurfuryl alcohol, propylene glycol, benzyl alcohol, 1,3-butanediol, 1,4-butanediol, 2,3-butanediol, γ-butyrolactone, acetone, methyl ethyl ketone, methyl isopropyl ketone, diethyl ketone, methyl isobutyl ketone, methyl n-butyl ketone, cyclohexanone, ethyl acetate, isopropyl acetate, n-propyl acetate, isobutyl acetate, n-butyl acetate, ethyl lactate, methanol, ethanol, isopropanol, tert-butanol, allylalcohol, N-propanol, 2-methyl-2-butanol, isobutanol, N-butanol, 2-methyl-1-butanol, 1-pentanol, 2-methyl-1-pentanol, 2-ethylhexanol, 1-methoxy-2-propanol, tetrahydrofuran, 1,4-dioxane, N,N-dimethylformamide, N,N-dimethylacetamide, N-methylpyrrolidone, 1,3-dimethyl-2-imidazolidinone, dimethyl sulfoxide, N-cyclohexyl-2-pyrrolidinone and the like. These solvents may be used alone, or may be used in a combination of two kinds or more thereof.

The content of the solvent is not particularly limited. As long as the content does not affect the storage stability, it can be appropriately adjusted depending on the application. The concentration of the solid contents of the curable composition is preferably adjusted in a range of 0.01% by mass to 98% by mass, and more preferably 0.1% by mass to 95% by mass.

<<<Other Additives>>>

The curable composition of the present invention may contain surfactants, crosslinking agents, leveling agents, dispersing agents, plasticizers, thermal stabilizers, release agents or the like. Other additives may be appropriately selected depending on the application.

<<<<Surfactant>>>>

The curable composition of the present invention may contain a surfactant.

Examples of a surfactant include nonionic surfactants such as polyoxyethylene alkyl ethers such as polyoxyethylene lauryl ether, polyoxyethylene stearyl ether, polyoxyethylene cetyl ether, polyoxyethylene oleyl ether; polyoxyethylene alkylaryl ethers such as polyoxyethylene octylphenol ether, polyoxyethylene nonylphenol ether; polyoxyethylene•polyoxypropylene block copolymers; sorbitan fatty acid esters such as sorbitan monolaurate, sorbitan monopalmitate, sorbitan monostearate, sorbitan monooleate, sorbitan trioleate, sorbitan tristearate; polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, polyoxyethylene sorbitan tristearate, trade names of EFTOP EF301, EF303, EF352 (manufactured by Mitsubishi Materials Electronic Chemicals Co., Ltd. (formerly Jemco Co., Ltd.)), trade names of MEGAFACE F171, F173, R-08, R-30, F-553, F-554 (manufactured by DIC Corporation), FLUORAD FC430, FC431 (manufactured by Sumitomo 3M Limited), fluorine-containing surfactants such as trade names of ASAHI GUARD AG710, SURFLON S-382, SC101, SC102, SC103, SC104, SC105, SC106 (manufactured by Asahi Glass Co., Ltd.), organosiloxane polymers KP341 (manufactured by Shin-Etsu Chemical Co.), BYK-302, BYK-307, BYK-322, BYK-323, BYK-330, BYK-333, BYK-370, BYK-375, BYK-378 (manufactured by BYK Japan Co., Ltd.), and the like.

The surfactant may be used alone, or may be used in a combination of two kinds or more.

The curable composition of the present invention may not contain a surfactant, but in case where the composition contains a surfactant, the content of the surfactant is preferably 0.0001% by mass to 5% by mass, more preferably 0.001% by mass to 2% by mass, and even more preferably 0.01% by mass to 1% by mass with respect to the mass of the compound represented by Formula (1).

<<<<Crosslinking Agent>>>>

The curable composition of the present invention may contain a crosslinking agent.

The cross-linking agent is not particularly limited as long as it is a compound having a substituent capable of reacting with a compound represented by the general formula (1). Examples thereof include vinyl compounds, allyl compounds, (meth)acrylate compounds having two or more of (meth)acryloyl groups in one molecule, and the like. From the viewpoint of reactivity, (meth) acrylate compounds are preferable.

Examples of the (meth)acrylate compound having two or more (meth)acryloyl groups in one molecule include ethylene glycol diacrylate, ethylene glycol dimethacrylate, polyethylene glycol diacrylate, polyethylene glycol dimethacrylate, ethoxylated bisphenol A diacrylate, ethoxylated bisphenol A dimethacrylate, ethoxylated trimethylol propane triacrylate, ethoxylated trimethylol propane trimethacrylate, ethoxylated glycerintriacrylate, ethoxylated glycerin trimethacrylate, ethoxylated pentaerythritol tetraacrylate, ethoxylated pentaerythritol tetramethacrylate, ethoxylated dipentaerythritol hexaacrylate, polyglycerin monoethylene oxide polyacrylate, polyglycerin polyethylene glycol polyacrylate, dipentaerythritol hexaacrylate, dipentaerythritol hexamethacrylate, neopentyl glycol diacrylate, neopentyl glycol dimethacrylate, pentaerythritol triacrylate, pentaerythritol trimethacrylate, trimethylol propane triacrylate, trimethylol propane trimethacrylate, tricyclodecane dimethanol diacrylate, tricyclodecane dimethanol dimethacrylate, 1,6-hexane diol diacrylate, 1,6-hexanediol dimethacrylate, and the like. These compounds may be commercially available, and specific examples thereof include NKESTER A-200, NKESTER A-400, NKESTER A-600, NKESTER A-1000, NKESTER A-TMPT, NKESTER UA-53H, NKESTER 1G, NKESTER 2G, NKESTER 3G, NKESTER 4G, NKESTER 9G, NKESTER 14G, NKESTER 23G, NKESTER ABE-300, NKESTER A-BPE-4, NKESTER A-BPE-6, NKESTER A-BPE-10, NKESTER A-BPE-20, NKESTER A-BPE-30, NKESTER BPE-80N, NKESTER BPE-100N, NKESTER BPE-200, NKESTER BPE-500, NKESTER BPE-900, NKESTER BPE-1300N, NKESTER A-GLY-3E, NKESTER A-GLY-9E, NKESTER A-GLY-20E, NKESTER A-TMPT-3EO, NKESTER A-TMPT-9EO, NKESTER ATM-4E, NKESTER ATM-35E (the above, manufactured by Shin-Nakamura chemical industry Co., Ltd.), KAYARAD (registered trademark) DPEA-12, KAYARAD PEG400DA, KAYARAD THE-330, KAYARAD RP-1040 (the above, manufactured by Nippon Kayaku Co., Ltd.), M-210, M-350 (the above, manufactured by Toagosei Co., Ltd.), KAYARAD (registered trademark) DPHA, KAYARAD NPGDA, KAYARAD PET30 (the above, manufactured by Nippon Kayaku Co., Ltd.), NKESTER A-DPH, NKESTER A-TMPT, NKESTER A-DCP, NKESTER A-HD-N, NKESTER TMPT, NKESTER DCP, NKESTER NPG, NKESTER HD-N (the above, manufactured by Shin-Nakamura chemical industry Co., Ltd.) and the like.

The curable composition of the present invention may not contain a crosslinking agent, but in a case where the composition contains a crosslinking agent, the content of the crosslinking agent is preferably 0.0001% by mass to 20% by mass and more preferably 0.001% by mass to 15% by mass with respect to the mass of the compound represented by Formula (1).

<Method of Preparing the Curable Composition>

The curable composition of the present invention can be prepared by mixing the respective components described above.

<Use of the Curable Composition>

Since the curable composition of the present invention can form a cured material having a high refractive index, the composition can be preferably used as a curable composition for forming an optical component or a coating composition.

The optical component is not particularly limited. Since the curable composition of the present invention can form a cured material having a high refractive index and further a transparency, the composition can be suitably particularly used to form, particularly, an optical component (so-called a passive optical component) for transmitting light such as a lens and the like.

As a use of the coating composition, for example, the coating composition can be preferably used in forming the film which transmits light particularly. For example, the coating composition can be suitably used as a part of materials to produce an electronic device such as a transparent touch panel, a liquid crystal display, an organic electroluminescence (EL) display, an optical semiconductor (LED) element, a solid-state imaging device, an organic thin-film solar cell, a dye-sensitized solar cell, an organic thin-film transistor (TFT) and the like. Particularly, the coating composition can be suitably used as a film embedded in or a planarizing film on the photodiode which is a member of a solid-state imaging device requiring a high refractive index, a planarization film before and after the color filter, a microlens, a planarizing film of the microlens, a conformal film, and an insulating film or a protective film which is a member of a transparent touch panel.

<<Curable Composition for Forming an Optical Component>>

In a case where the curable composition of the present invention is used as a curable composition for forming an optical component, the content of the compound represented by Formula (1) is preferably 20% by mass to 98% by mass and more preferably 50% by mass to 90% by mass with respect to the total solid content of the curable composition.

In a case where the composition contains a photo radical polymerization initiator, the content of the photo radical polymerization initiator is preferably 0.01% by mass to 5% by mass, more preferably 0.05% by mass to 1.0% by mass and particularly preferably 0.05% by mass to 0.5% by mass with respect to the mass of the compound represented by Formula (1).

In a case where the composition contains a thermal radical polymerization initiator, the content of the thermal radical polymerization initiator is preferably 0.01% by mass to 5.0% by mass, more preferably 0.1% by mass to 4.0% by mass and particularly preferably 0.3% by mass to 3.0% by mass with respect to the mass of the compound represented by Formula (1).

The concentration of the solid contents is preferably 20% by mass to 99% by mass and more preferably 40% by mass to 99% by mass.

Furthermore, the composition may contain a monofunctional (meth)acrylate monomers, a non-conjugated vinylidene group-containing compound, a polymer having a polymerizable group in the side chain and the like.

In a case where the composition contains a monofunctional (meth)acrylate monomer, the content of the monofunctional (meth)acrylate monomer is preferably 10% by mass to 200% by mass, and more preferably 20% by mass to 160% by mass with respect to the mass of the compound represented by Formula (1).

In a case where the composition contains a non-conjugated vinylidene group-containing compound, the content of the non-conjugated vinylidene group-containing compound is preferably 0.5% by mass to 30% by mass, more preferably 1% by mass to 25% by mass and particularly preferably 2% by mass to 20% by mass with respect to the total solid content of the curable composition.

In a case where the composition contains a polymer having a polymerizable group in a side chain, the content of the polymer having a polymerizable group in a side chain is preferably 1% by mass to 90% by mass, more preferably 2% by mass to 80% by mass and particularly preferably 5% by mass to 60% by mass with respect to the total solid content of the curable composition.

Furthermore, as other additives, the composition may further include crosslinking agents, dispersing agents, plasticizers, thermal stabilizers, releasing agents and the like.

<<Coating Composition>>

In a case where the curable composition of the present invention is used as coating composition, the content of the compound represented by Formula (1) is preferably 70% by mass to 99% by mass and more preferably 80% by mass to 99% by mass with respect to the total solid content of the curable composition.

In a case where the composition contains a photo radical polymerization initiator, the content of the photo radical polymerization initiator is preferably 0.01% by mass to 10% by mass, more preferably 0.05% by mass to 5% by mass and particularly preferably 0.05% by mass to 2% by mass with respect to the mass of the compound represented by Formula (1).

In a case where the composition contains a thermal radical polymerization initiator, the content of the thermal radical polymerization initiator is preferably 0.01% by mass to 8% by mass, more preferably 0.1% by mass to 6% by mass and particularly preferably 0.3% by mass to 5% by mass with respect to the mass of the compound represented by Formula (1).

The concentration of solid contents is preferably 0.1% by mass to 98% by mass and more preferably 0.1% by mass to 95% by mass.

Further, the composition may further contain surfactants, crosslinking agents, leveling agents and the like.

The content of the monofunctional (meth)acrylate monomer is preferably 0% by mass to 20% by mass, more preferably 0% by mass to 10% by mass, and particularly preferably not contained with respect to the mass of the compound represented by Formula (1).

<Method of Manufacturing Cured Material>

The curable composition of the present invention may be cured by performing at least one of photoirradiation or heating.

Method of manufacturing cured material varies depending on the use. For example, it is possible to produce a cured material that is formed into a desired shape using a mold. Further, it is possible to produce a film-like cured material by applying the curable composition of the present invention onto a substrate, and then performing at least one of photoirradiation or heating.

<<Method of Manufacturing Cured Material by Using a Mold>>

In a case where a cured material is manufactured by using a mold, the cured material can be produced by injecting a curable composition into a mold and then by performing at least one of photoirradiation or heating. Preparation of the cured material can be obtained by injecting a curable composition into the mold and curing it at once, but it is preferable to produce a cured material by injecting the curable composition into the mold to produce a semi-cured material, taking out the semi-cured material from the mold, transferring the semi-cured material into another mold, and performing at least one of irradiation or heating.

Here, the term "semi-cured material" is obtained by polymering the curable composition and it means a material in the state of not completely being solid but having certain fluidity. For example, the optical and/or heating polymer of the curable composition in the state of complex viscosity of $10^5$ mPa·s to $10^8$ mPa·s at 25° C., and a frequency of 10 Hz is a semi-cured material. Particularly, it is preferably considered that the semi-cured material has the upper limit value of the complex viscosity of 1.0 mPa·s×$10^9$ mPa·s at 25° C., and a frequency of 10 Hz. On the other hand, the term "cured material" is obtained by polymering the curable composition and it means a material in the state of completely being solid.

Hereinafter, it will be specifically described with reference to preferred embodiments. Further, the preferred embodiment that is common to both semi-curing step and curing step is described in the semi-curing step.

<<<Semi-Curing Step>>>

The semi-curing step may preferably form a semi-cured material of the complex viscosity of $10^5$ mPa·s to $10^8$ mPa·s at 25° C. and the frequency of 10 Hz by performing at least one of photoirradiation or heating on the curable composition of the present invention. Among them, it is preferable to form the above described semi-cured material by performing photoirradiation on the curable composition of the present invention. In a case of forming the semi-cured material by photoirradiating on the curable composition, the curable composition of the present invention may preferably contain a photo-radical polymerization initiator.

In semi-curing step, a semi-cured material may be produced with the same mold as the mold used in the curing step to be described later. Further, the semi-cured material may be produced with a different mold as the mold used in curing step to be described later.

Here, the mold used for manufacturing the cured material is generally a combination of two mold and is adapted to heat the contents under pressure. Thus, if the composition having a low viscosity is injected to the mold, it becomes a cause of the leak to the mold clearance. Therefore, in one preferred embodiment of the method of manufacturing the cured material, a semi-curing step and a curing step described below may be carried out in a single mold by adding a polymer having a polymerizable group in a side chain in the curable composition to adjust the viscosity of the composition. This aspect is preferable from the viewpoint of productivity.

Further, in another preferred aspect of the method of producing cured material, a mold for producing a semi-cured material and a mold for producing a cured material were separately prepared to produce a semi-cured material. The prepared semi-cured material was taken out from the mold and transferred into a mold for producing a cured material. A cured material may be produced by performing a curing process to be described later. According to this aspect, since the trouble of adjusting viscosity can be avoided by adding a polymer having a polymerizable group in a side chain and the like in the curable composition, the cured material is preferable from the viewpoint of reducing the material cost.

In addition, in the case of using another mold which is different from the mold for producing cured material as a mold for producing a semi-cured material, it is preferable to use a mold in a so-called preform. The type of preform may be made of metal, of glass, or of resin. When considering that repeated use in mass production process, the type of preform is preferably made of metal or glass. Further, in the case of using a cured material as a lens, at least one surface of the mold in the preform shape preferably has the same shape/or similar shape as the mold, and both surfaces of the mold more preferably have the same shape/or similar shape as the mold shape.

<<<Conditions of Photoirradiation>>>

Preferred conditions of photoirradiation in the semi-curing step will be described below.

Photoirradiation may preferably be carried out so that the complex viscosity of semi-cured material becomes to be $10^5$ mPa·s to $10^8$ mPa·s at 25° C. and the frequency of 10 Hz after photoirradiation, more preferably carried out to be $10^5$ mPa·s to $10^{7.5}$ mPa·s and particularly preferably carried out to be $10^{5.5}$ mPa·s to $10^{7.5}$ mPa·s.

As the light used for photoirradiation, ultraviolet ray or visible light is preferable and ultraviolet ray is more preferable. For example, metal halide lamps, low pressure mercury lamps, high pressure mercury lamps, ultrahigh pressure mercury lamps, germicidal lamps, xenon lamps, LED light source lamps or the like are preferably used.

The atmosphere during light irradiation is preferably in the air or in an atmosphere substituted with an inert gas atmosphere, and more preferably an atmosphere substituted with nitrogen until an oxygen concentration becomes 1% or less.

<<<Semi-Cured Material>>>

The semi-cured material is manufactured through the semi-curing step as described above. Such a semi-cured material can be preferably used in the preparation of the cured material.

In the semi-cured material, the photo-radical polymerization initiator may not be included at all due to its whole consumption after the photoirradiation step, or the photo-radical polymerization initiator may remain.

The glass-transition temperature (hereinafter, also referred to as Tg) of the semi-cured material is preferably −150° C. to 0° C., more preferably −50° C. to 0° C., and particularly preferably −20° C. to 0° C.

<<<Curing Step>>>

A cured material can be obtained by curing the curable composition at once, but it is preferable to obtain a cured material by placing the semi-cured material in the mold, pressurizing it to deform, heating and thermally polymerizing it. After obtaining a cured material by thermal polymerization, the curable composition of the present invention preferably contains a thermal radical polymerization initiator.

Further, the mold used in the curing step is also referred to as thermoforming mold. The thermoforming mold preferably has the configuration that two molds may generally be combined and the contents thereof may be heated under pressure. Moreover, in the curing step, it is more preferable to use a metal mold as the mold at the time of thermal polymerization. As such a thermoforming mold, for example, it is possible to use those described in JP2009-126011A.

In the curing step, it is preferred to carry out of putting the semi-cured material in a mold for thermoforming.

The semi-cured product, as described in the semi-curing process, has been prepared by injecting curable composition into a mold for thermoforming and then performing at least one of photoirradiating or heating the composition, or by placing the curable composition in another mold other than the mold for thermoforming and then performing at least one of photoirradiating or heating the composition.

If the semi-cured material is prepared in the former method, the operation of putting the semi-cured material into a mold for thermoforming is not required in the curing step, and thus it is to place the semi-cured material in the forming mold only for its description.

On the other hand, if the semi-cured material is prepared in the latter method, the semi-cured material is moved into a mold for thermoforming. As a method of moving the semi-cured material into the mold for thermoforming, for example, air tweezers with a syringe, a vacuum pad or a vacuum generator, or the like can be used. As described above, since the complex viscosity of the semi-cured material is within a specific range, it is possible to easily move the material into the mold for thermoforming using air tweezers or the like.

In the curing step, it is preferable to obtain a cured material by placing the semi-cured material in a mold, deforming it under pressure, and thermally polymerizing it by heating.

Deforming under pressure and heating may be carried out at the same time, heating may be carried out after deforming under pressure, or deforming under pressure may be performed after heating, but among them, it is preferred to perform deforming under pressure and heating simultaneously. Further, heating and deforming under pressure are conducted simultaneously, it is also preferred that the pressure is stable and then further heating to a higher temperature is carried out.

The pressure in deforming under pressure is preferably 1 kg/cm² to 100 kg/cm², more preferably 3 kg/cm² to 50 kg/cm², and particularly preferably 3 kg/cm² to 30 kg/cm².

The heating temperature is, in a case of heating with deforming under pressure at the same time, preferably 80° C. to 300° C., more preferably 120° C. to 300° C. and particularly preferably 150° C. to 280° C.

The heating temperature is, in a case where the pressure is stable and then further heating is carried out, preferably 80° C. to 300° C., more preferably 120° C. to 300° C. and particularly preferably 150° C. to 280° C.

The time for thermal polymerization is preferably 30 seconds to 1000 seconds, more preferably 30 seconds to 500 seconds, and particularly preferably 60 seconds to 300 seconds.

The atmosphere during the thermal polymerization is preferably an atmosphere substituted with an air or inert gas, and more preferably an atmosphere purged with nitrogen until an oxygen concentration of 1% or less.

<<Method for Producing Film-Like Cured Material>>

The curable composition of the present invention is applied onto a substrate and at least one of photoirradiating and heating is performed to produce a film-like cured material. That is, it is possible to use a curable composition of the present invention as a coating composition.

Coating method of the curable composition is not particularly limited. For example, a spin coating method, a dip method, a flow coating method, an inkjet method, a spraying method, a bar coating method, a gravure coating method, a slit coating method, a roll coating method, a transfer printing method, a brush coating, a blade coating method, an air knife coating method or the like can be employed.

Moreover, the substrate is not particularly limited, but it varies depending on applications. Examples thereof include glass deposited with silicon, indium tin oxide (ITO), glass deposited with indium zinc oxide (IZO), a polyethylene terephthalate (PET), substrates made of plastic, glass, quartz, ceramics or the like. It is also possible to use a flexible substrate having flexibility.

<Cured Material>

The cured product is manufactured by the manufacturing method of the cured material as described above using the curable composition of the present invention. Hereinafter, the preferred properties of the cured material will be described.

<<Refractive Index>>

In the present invention, the cured material having a high refractive index is preferable from the viewpoint of using it in optical components such as lenses. In the present invention, the refractive index nD of the cured product is preferably 1.45 or more, more preferably 1.58 or more, particularly preferably 1.62 or more, more particularly preferably 1.63 or more, and most preferably 1.65 or more at a wavelength of 589 nm. Further, in the case of film-like cured material, the refractive index nD is preferably 1.45 or more, more preferably 1.68 or more, particularly preferably 1.71 or more, and most preferably 1.74 or more.

(Abbe Number)

In the cured material of the present invention, a low Abbe number is preferable from the viewpoint of reducing chromatic aberration when using such a lens among optical components uses. In the cured material of the present invention, the Abbe number is preferably 30 or less, more preferably 25 or less, particularly preferably 23.5 or less, more particularly preferably 23 or less, even more particularly preferably 22.5 or less, and most preferably 22 or less at a wavelength of 589 nm.

Herein, the Abbe number vD is calculated by measuring each of refractive indexes, nD, nF, and nC at wavelengths of 589 nm, 486 nm, and 656 nm, respectively by the following Formula (A).

$$vD = \frac{nD - 1}{nF - nC} \quad \text{Formula (A)}$$

(Size)

The size of the cured material varies depending on its uses. For example, when used as an optical component such as a lens, the maximum thickness of the cured material is preferably 0.1 mm to 10 mm, more preferably 0.1 mm to 5 mm, and particularly preferably 0.15 mm to 3 mm. The maximum diameter of the cured material is preferably 1 mm to 1000 mm, more preferably 2 mm to 50 mm, and particularly preferably 2.5 mm to 10 mm. The cured material with such a size is particularly useful as an optical component use with a high refractive index. Even though such a thick molded article (cured material) is manufactured by a solution casting method, it is not easy to be molded and cracks are likely to occur. However, according to the curable composition of the present invention, the occurrence of cracks can be suppressed, and such a thick molded article (cured material) can be formed with a high yield.

Further, in the case of film-like cured material, the size is preferably 0.01 µm to 500 µm, and more preferably 0.02 µm to 200 µm.

<Optical Component>

An optical component of the present invention is formed using the curable composition of the present invention. That is, the optical component of the present invention is one including a cured material of the curable composition of the present invention.

Types of optical components are not particularly limited. In particular, it can be suitably used as an optical component using excellent optical properties of the curable composition, and particularly an optical component which transmits light (so called passive optical component). Examples of the optical functional device having such an optical component include for example, various display devices (a liquid crystal display or a plasma display, or the like), various kinds of projectors (an OHP, a liquid crystal projector, or the like), an optical fiber communication device (an optical waveguide, an optical amplifier, or the like), a camera, an imaging device such as a video device or the like.

As the passive optical components used in optical function devices, for example, a lens, a prism, a prism sheet, panel (plate-shaped molded body), a film, an optical waveguide (film-like or fibrous shape, or others), optical disks, a sealing agent of LEDs or the like are exemplified. Such a passive optical component may be used, if necessary, as an optional coating layer, for example, a protective layer that prevents mechanical damage of the coating surface due to friction or abrasion, a light absorbing layer absorbing rays of undesired wavelength which causes degradation of inorganic particles, substrates or the like, a transmissive shielding layer to inhibit or prevent the transmission of low reactive molecules such as oxygen gas and moisture, an antiglare layer, an antireflection layer, a low refractive index layer, a multi-layer structure with an optional additional function layer, or the like. Specific examples of such an optional cover layer include a transparent conductive film and a gas barrier film consisting of an inorganic oxide coating layer, a gas barrier film and a hard coat consisting of an organic material coating layer or the like. It is possible to use a known coating method such as a vacuum deposition method, a CVD method, a sputtering method, a dip coating method, a spin coating method or the like as the coating method.

The optical component of the present invention is particularly suitable for a lens substrate. The lens substrate manufactured by using the curable composition of the present invention has a high refractivity, further excellent transparency, and excellent optical properties. Further, it is possible to arbitrarily adjust the refractive index of the lens substrate by suitably adjusting the types of monomers constituting the curable composition.

In addition, the term "lens substrate" in this specification means a single member which can exhibit a lens function. A film or a member can be provided on the surface or the periphery of the lens substrate in accordance with the use environment and application of the lens. For example, a protective film, an antireflection film, a hard coating film or the like can be formed on the surface of the lens substrate. Further, the periphery of the lens substrate can be fixed to fit into such a substrate holding frame. However, since these films or the frame are members to be added to the lens substrate, they are distinguished from the lens substrate itself referred to here in this specification.

A lens substrate itself may be used alone as a lens, when utilizing the lens substrate as a lens, or a lens with the added membranes or frames as described above may be used as. The types and shapes of the lens using the lens substrate are not particularly limited.

Since the lens substrate has low Abbe number, it can be preferably used in the chromatic aberration correction lens. The chromatic aberration correction lens can be preferably used, for example, in the imaging lens such as a mobile phone, a digital camera or the like, a Motion Picture lens such as TV camera, a video camera or the like, and further the one used in vehicle or an endoscope lens or the like.

<Compound>

Next, the compound of the present invention will be described.

The compound of the present invention is a compound represented by the above described Formula (11).

The compound represented by Formula (11) is preferably a compound represented by the above described Formula (12).

Further, the compound represented by Formula (11) is preferably a compound represented by the above described Formula (13A) or (13B).

Further, the compound represented by Formula (11) is preferably a compound represented by the above described Formula (14).

Further, the compound represented by Formula (11) is preferably a compound represented by the above described Formula (15).

The preferred ranges of Formula (11), Formula (12), Formula (13A), Formula (13B), Formula (14) and Formula (15) are similar to the ranges described in the above described Formula (11), Formula (12), Formula (13A), Formula (13B), Formula (14) and Formula (15).

As specific examples of the compounds of the present invention, the above described compounds (1-1) to (1-46) and the like will be exemplified.

The compound of the present invention can form a cured material having a high refractive index due to its excellent solubility in solvent. Therefore, the compound can be used in an optical component and the coating composition.

EXAMPLES

The features of the present invention will be specifically explained with reference to the following examples. Materials, used amounts, ratio, processing contents, processing procedures and the like shown in the following examples can be appropriately changed as long as they do not depart from the scope of the present invention. Accordingly, the scope of the present invention should not limitatively be interpreted by the following specific Examples.

Examples 1-1 to 1-20, Comparative Example 1-1

A curable composition was prepared by mixing each of components and homogenizing them with stirring until having the composition shown in the following Table.

Detailed description of abbreviations indicating each of compounds used in Examples and Comparative Examples are as follows.

<Compound Containing Aromatic Ring>

Compound 1: The Following Structure

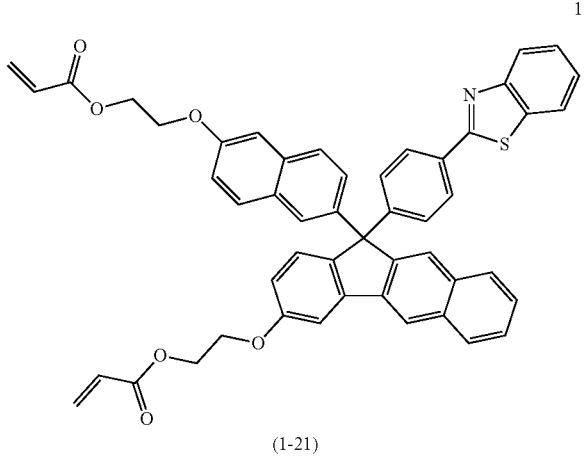 [SMILES: C=CC(=O)OCCOc1ccc2c(c1)-c1cc3ccccc3cc1C2(c1ccc(-c2nc3ccccc3s2)cc1)c1ccc2cc(OCCOC(=O)C=C)ccc2c1]

(1-21)

Compound 2: The Following Structure

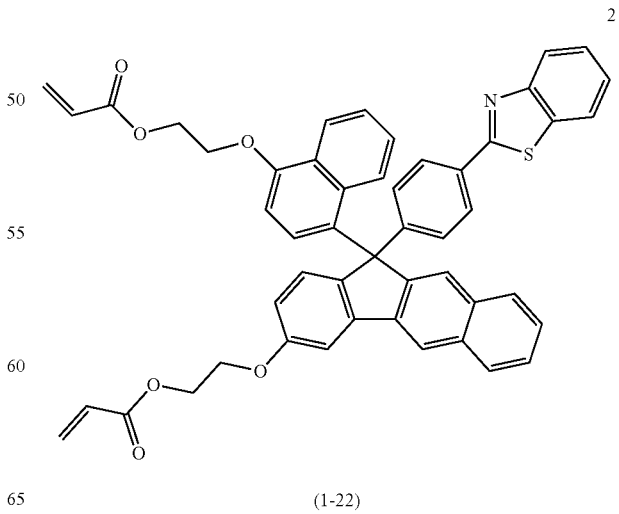

(1-22)

Compound 3: The Following Structure
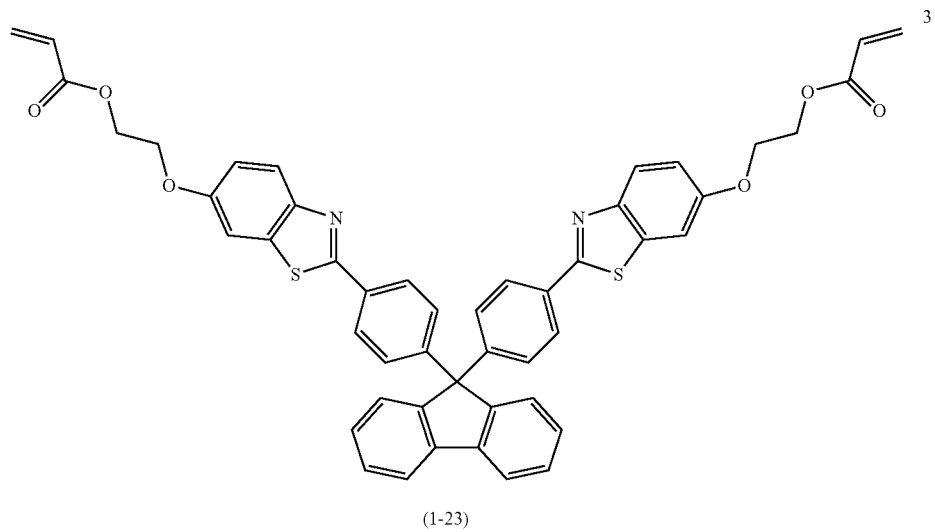 [SMILES: C=CC(=O)OCCOc1ccc2nc(-c3ccc(C4(c5ccc(-c6nc7ccc(OCCOC(=O)C=C)cc7s6)cc5)c5ccccc5-c5ccccc54)cc3)sc2c1]
(1-23)
Compound 4: The Following Structure
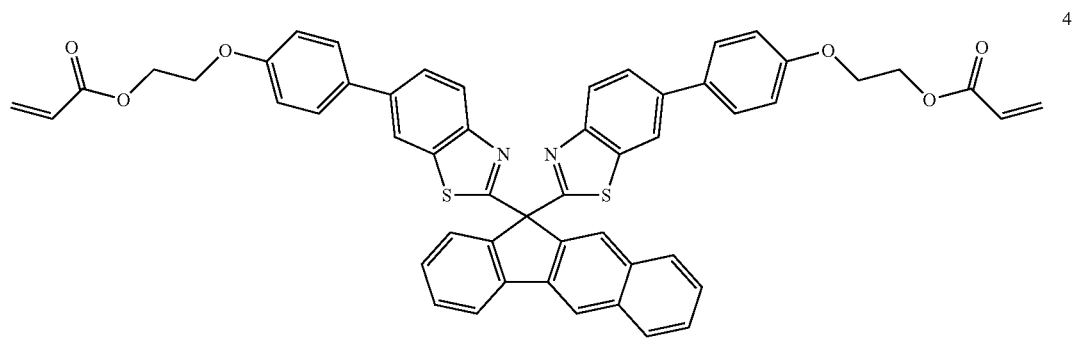
(1-24)
Compound 5: The Following Structure
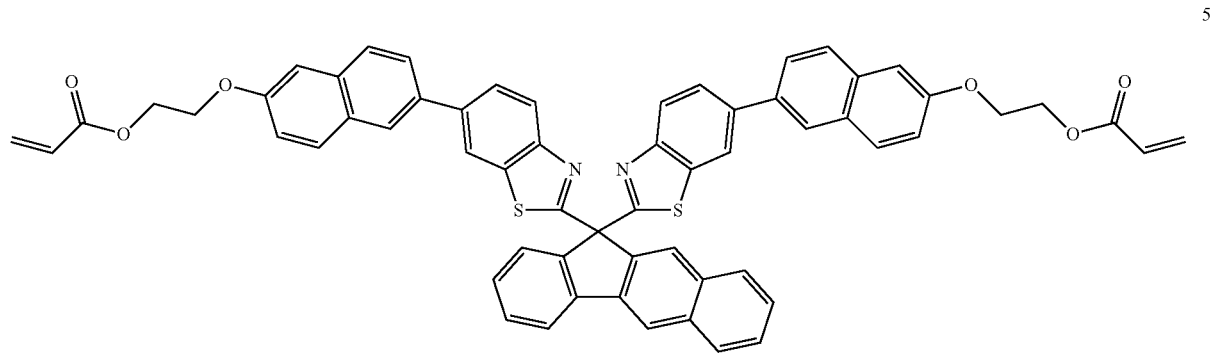
(1-25)

Compound 6: The Following Structure
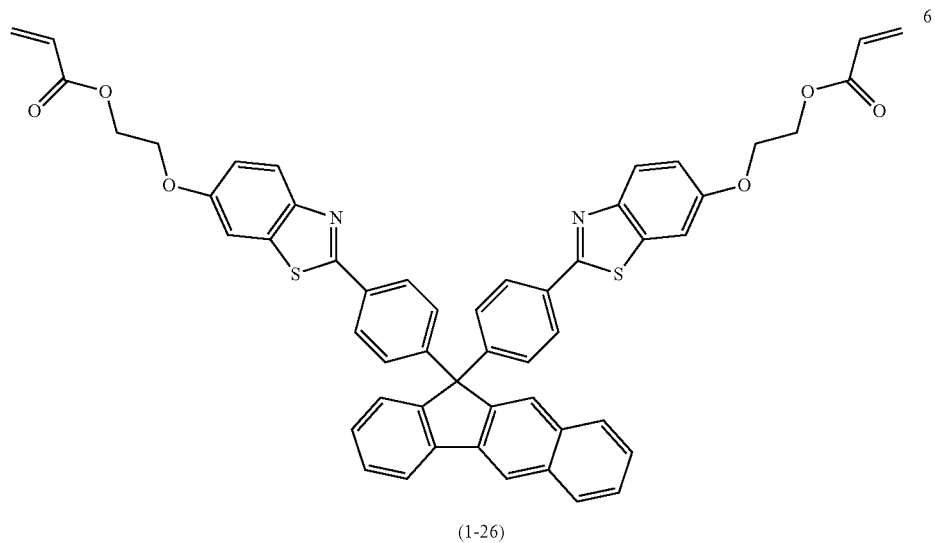 [SMILES: C=CC(=O)OCCOc1ccc2nc(-c3ccc(C4(c5ccc(-c6nc7ccc(OCCOC(=O)C=C)cc7s6)cc5)c5ccccc5-c5cc6ccccc6cc54)cc3)sc2c1]
(1-26)
Compound 7: The Following Structure
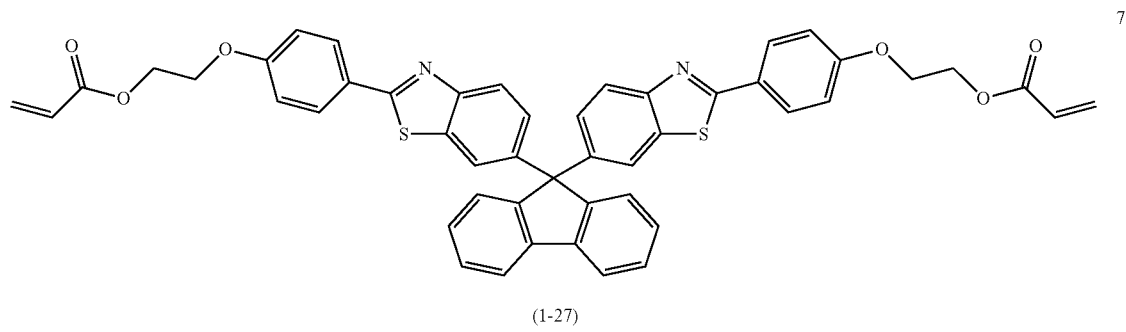 [SMILES: C=CC(=O)OCCOc1ccc(-c2nc3ccc(C4(c5ccc6nc(-c7ccc(OCCOC(=O)C=C)cc7)sc6c5)c5ccccc5-c5ccccc54)cc3s2)cc1]
(1-27)
Compound 8: The Following Structure
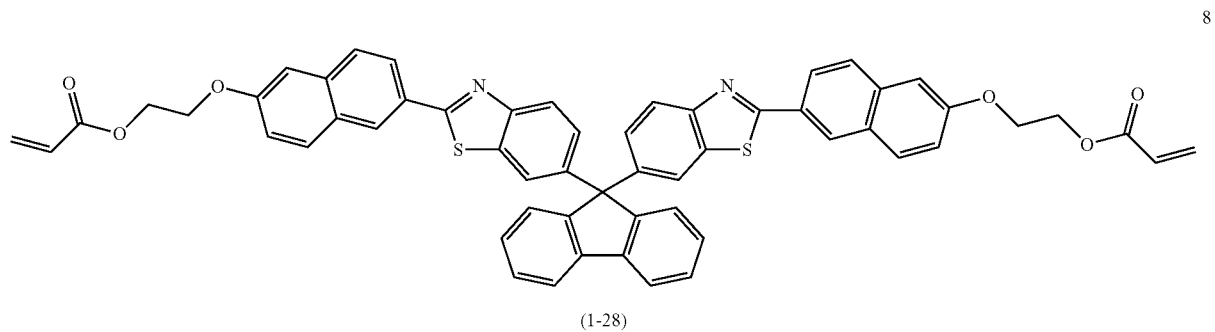 [SMILES: C=CC(=O)OCCOc1ccc2cc(-c3nc4ccc(C5(c6ccc7nc(-c8ccc9cc(OCCOC(=O)C=C)ccc9c8)sc7c6)c6ccccc6-c6ccccc65)cc4s3)ccc2c1]
(1-28)

Compound 9: The Following Structure
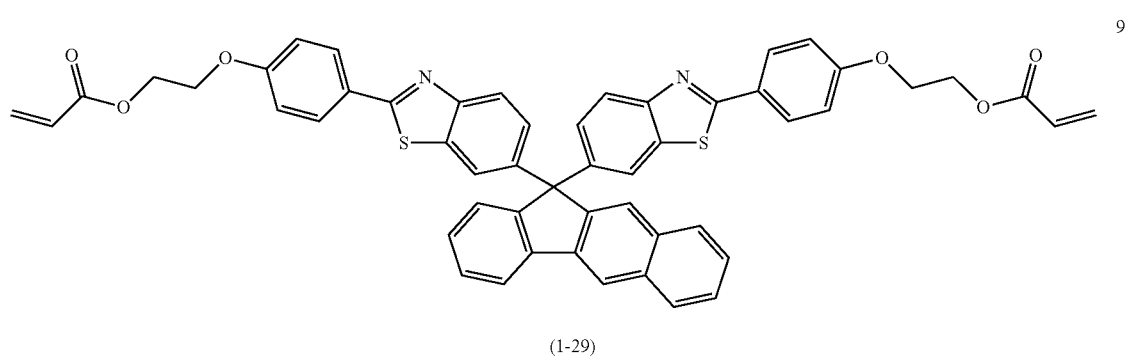 [SMILES: C=CC(=O)OCCOc1ccc(-c2nc3ccc(C4(c5ccc6nc(-c7ccc(OCCOC(=O)C=C)cc7)sc6c5)c5ccccc5-c5cc6ccccc6cc54)cc3s2)cc1]
(1-29)
Compound 10: The Following Structure
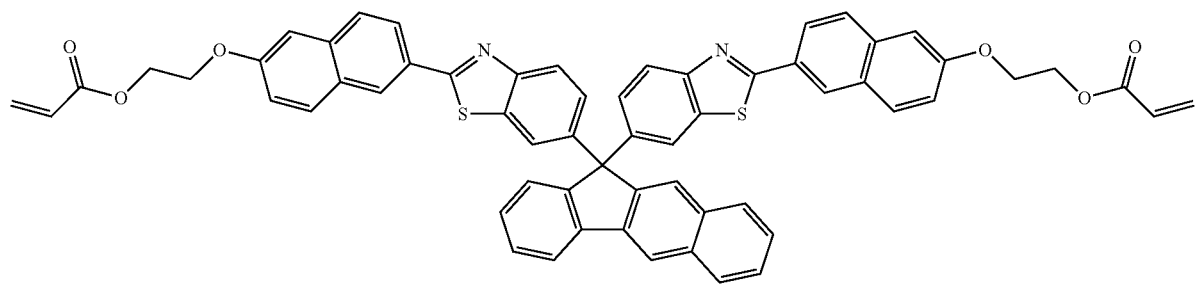
(1-30)
Compound A: The Following Structure
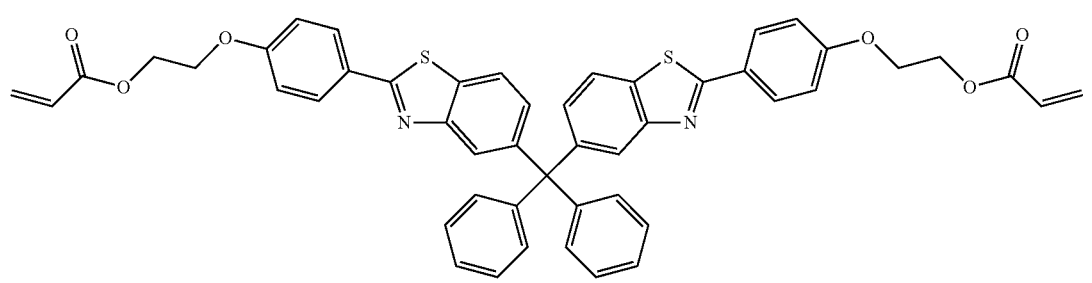
(1-2)

Compound B: The Following Structure
Compound E: The Following Structure
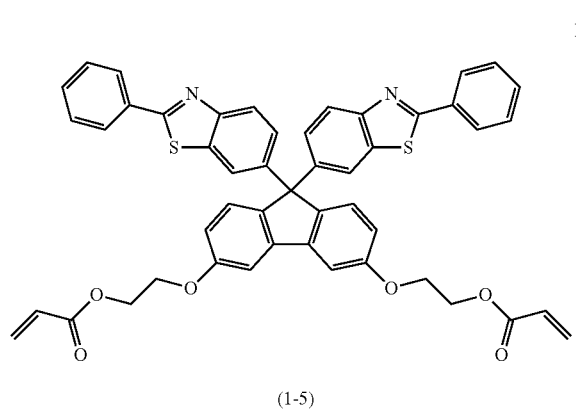
(1-5)
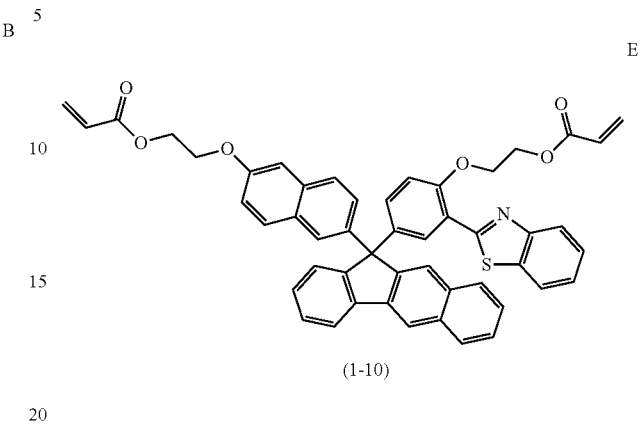
(1-10)
Compound C: The Following Structure
Compound F: The Following Structure
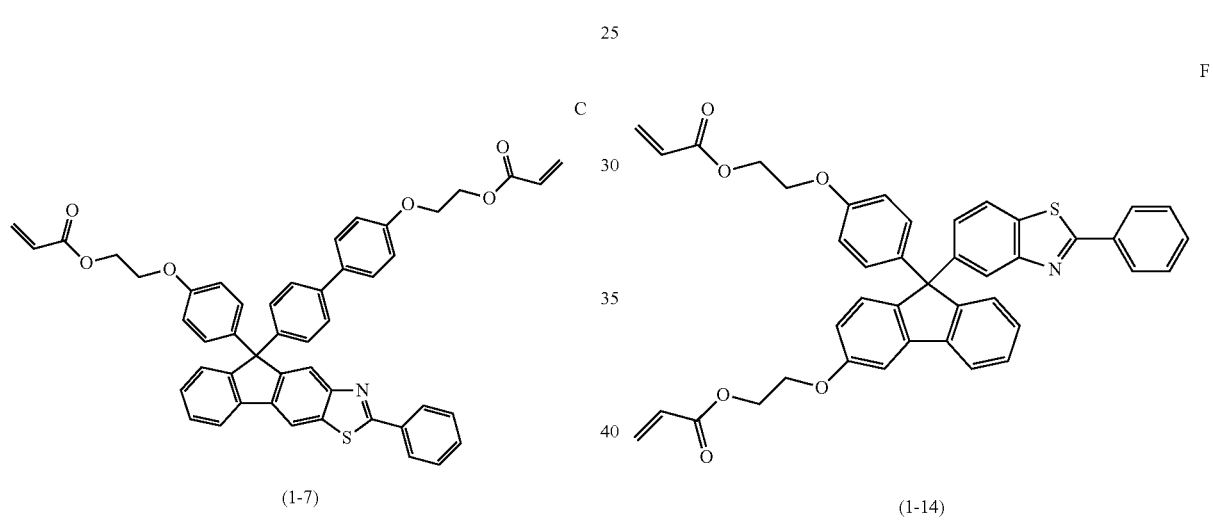
(1-7)
(1-14)
Compound D: The Following Structure
Compound G: The Following Structure
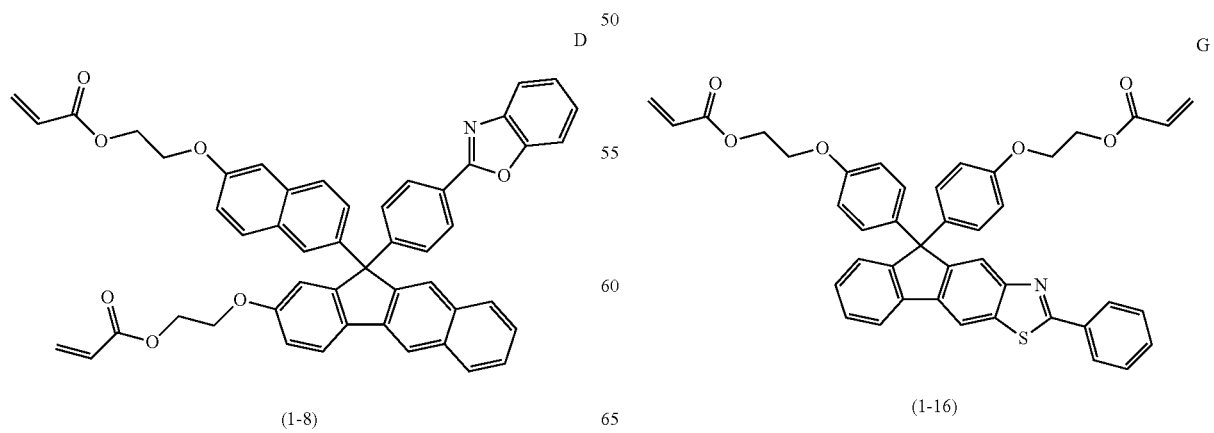
(1-8)
(1-16)

Compound H: The Following Structure
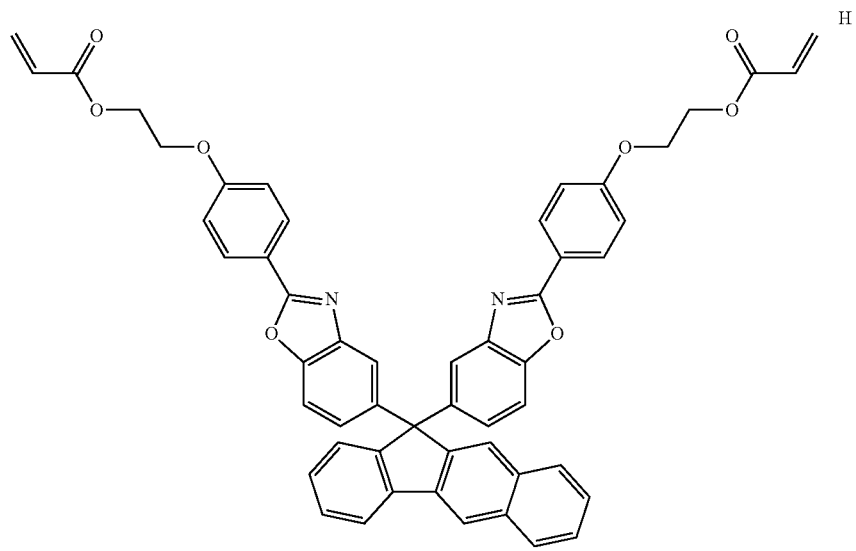
(1-18)
Compound I: The Following Structure
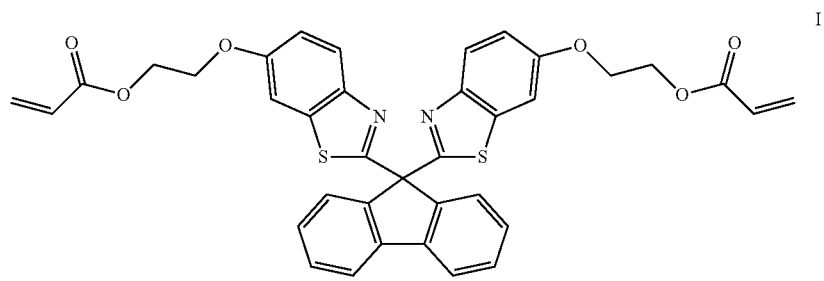
(1-19)

Compound J: The Following Structure

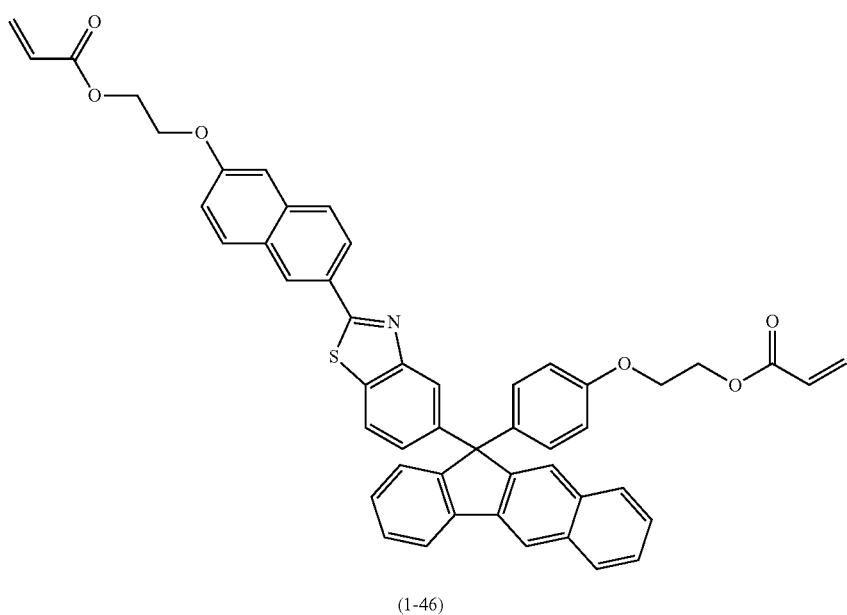

(1-46)

Comparative Compound 1: The Following Structure ([Chem. 22] (19) of Example 1 of JP2012-082386A)

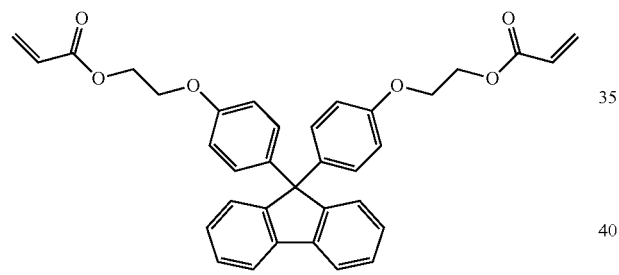

<Monofunctional (Meth)Acrylic Monomer>
PhOEA: the following structure (manufactured by Tokyo Chemical Industry Co., Ltd., trade name of acrylic acid 2-phenoxyethyl)

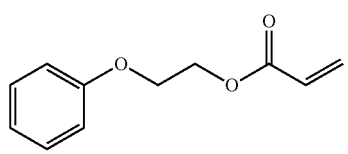

<Photo Radical Polymerization Initiator>
F-1: the following structure (manufactured by BASF Corp., trade name of IRGACURE 184)

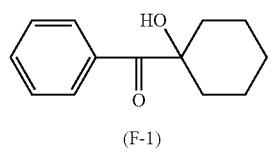

(F-1)

<Thermal Radical Polymerization Initiator>
F-2: the following structure (manufactured by NOF Corporation, trade name of PERBUTYL O)
F-3: the following structure (manufactured by NOF Corporation, trade name of PERCUMYL

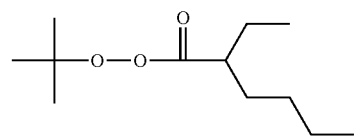

(F-2)

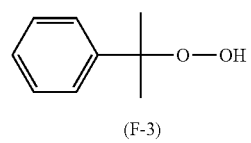

(F-3)

<Solvent Solubility Evaluation>

1 g of an aromatic ring-containing compound and 1 mL of propylene glycol monomethyl ether acetate (PGMEA) were stirred for 24 hours at 25° C. and then the aromatic ring-containing compound was mixed with PGMEA uniformly and evaluated by the following criteria.

A: 50% by mass or more of an aromatic ring-containing compound were dissolved in PGMEA.

B: 30% by mass or more and less than 50% by mass of an aromatic ring-containing compound were dissolved in PGMEA.

C: 5% by mass or more and less than 30% by mass of an aromatic ring-containing compound were dissolved in PGMEA.
D: The amount of an aromatic ring-containing compound dissolved in PGMEA was less than 5% by mass.

<Crack Initiation Evaluation>

A curable resin composition was applied on a transparent glass plate having a diameter of 10 mm and a thickness of 1 mm so as to cover the transparent glass plate surface with placing a spacer having a thickness of 1 mm, and then a transparent glass plate having a diameter of 10 mm and a thickness of 1 mm was bonded thereon. A thermosetting material was obtained by heating them for 5 minutes at 130° C., and then for 5 minutes at 200° C. using Hot plate.

The resulting thermosetting material was charged into a constant temperature tank held in the 85° C., 85% RH. What crack occurs in the thermosetting material obtained after 100 hours aging was set as a defective product, and what crack does not occur was set as a non-defective product. Ten thermosetting materials were evaluated and the percentage of non-defective thereof was evaluated as non-defective rate by the following criteria.
A: Non-effective ratio was 80% or more
B: Non-effective ratio was 50% or more and less than 80%
C: Non-effective ratio was 30% or more and less than 50%
D: Non-effective ratio was less than 30%

<Transmittance Evaluation>

The above described thermosetting material was evaluated by using an ultraviolet-visible absorption spectrum measurement apparatus UV-3100 (manufactured by Shimadzu Corporation) to measure the transmittance at a wavelength of 405 nm according to the following criteria.
A: Transmittance was 85% or more
B: Transmittance was less than 85%

<Refractive Index>

The refractive index of the above described thermosetting material at 589 nm was measured by using Abbe's meter (manufactured by ATAGO CO., LTD.).

TABLE 1

|  |  |  | Example 1-1 | Example 1-2 | Example 1-3 | Example 1-4 | Example 1-5 |
|---|---|---|---|---|---|---|---|
| Compound | Aromatic ring-containing compound | Kind | Compound A | Compound B | Compound C | Compound D | Compound E |
|  |  | Added amount (parts by mass) | 60 | 60 | 60 | 60 | 60 |
|  | Monofunctional (meth)acrylate monomer | Kind | PhOEA | PhOEA | PhOEA | PhOEA | PhOEA |
|  |  | Added amount (parts by mass) | 40 | 40 | 40 | 40 | 40 |
|  | Photo radical polymerization initiator (F-1) | Added amount (parts by mass) | 0.1 | 0.1 | 0.1 | 0.1 | 0.1 |
|  | Thermal radical polymerization initiator (F-2, F-3) | Added amount (parts by mass) | 1.7 | 1.7 | 1.7 | 1.7 | 1.7 |
| Evaluation | Solvent solubility evaluation |  | B | B | B | B | A |
|  | Crack initiation evaluation |  | B | B | A | A | A |
|  | Transmittance |  | B | A | A | A | A |
|  | Refractive index |  | 1.67 | 1.67 | 1.62 | 1.64 | 1.65 |

|  |  |  | Example 1-6 | Example 1-7 | Example 1-8 | Example 1-9 | Example 1-10 |
|---|---|---|---|---|---|---|---|
| Compound | Aromatic ring-containing compound | Kind | Compound F | Compound G | Compound H | Compound I | Compound J |
|  |  | Added amount (parts by mass) | 60 | 60 | 60 | 60 | 60 |
|  | Monofunctional (meth)acrylate monomer | Kind | PhOEA | PhOEA | PhOEA | PhOEA | PhOEA |
|  |  | Added amount (parts by mass) | 40 | 40 | 40 | 40 | 40 |
|  | Photo radical polymerization initiator (F-1) | Added amount (parts by mass) | 0.1 | 0.1 | 0.1 | 0.1 | 0.1 |
|  | Thermal radical polymerization initiator (F-2, F-3) | Added amount (parts by mass) | 1.7 | 1.7 | 1.7 | 1.7 | 1.7 |
| Evaluation | Solvent solubility evaluation |  | B | B | B | A | A |
|  | Crack initiation evaluation |  | B | A | A | A | A |
|  | Transmittance |  | A | A | A | A | A |
|  | Refractive index |  | 1.61 | 1.61 | 1.68 | 1.62 | 1.64 |

TABLE 2

|  |  |  | Example 1-11 | Example 1-12 | Example 1-13 | Example 1-14 | Example 1-15 | Example 1-16 |
|---|---|---|---|---|---|---|---|---|
| Compound | Aromatic ring-containing compound | Kind | Compound 1 | Compound 2 | Compound 3 | Compound 4 | Compound 5 | Compound 6 |
|  |  | Added amount (parts by mass) | 60 | 60 | 60 | 60 | 60 | 60 |

TABLE 2-continued

| | | | | | | | | |
|---|---|---|---|---|---|---|---|---|
| | Monofunctional (meth)acrylate monomer | Kind | PhOEA | PhOEA | PhOEA | PhOEA | PhOEA | PhOEA |
| | | Added amount (parts by mass) | 40 | 40 | 40 | 40 | 40 | 40 |
| | Photo radical polymerization initiator (F-1) | Added amount (parts by mass) | 0.1 | 0.1 | 0.1 | 0.1 | 0.1 | 0.1 |
| | Thermal radical polymerization initiator (F-2, F-3) | Added amount (parts by mass) | 1.7 | 1.7 | 1.7 | 1.7 | 1.7 | 1.7 |
| Evaluation | Solvent solubility evaluation | | A | A | A | A | A | A |
| | Crack initiation evaluation | | A | A | A | A | A | A |
| | Transmittance | | A | A | A | A | A | A |
| | Refractive index | | 1.65 | 1.65 | 1.68 | 1.67 | 1.68 | 1.66 |

| | | | Example 1-17 | Example 1-18 | Example 1-19 | Example 1-20 | Comparative Example 1-1 |
|---|---|---|---|---|---|---|---|
| Compound | Aromatic ring-containing compound | Kind | Compound 7 | Compound 8 | Compound 9 | Compound 10 | Comparative Compound 1 |
| | | Added amount (parts by mass) | 60 | 60 | 60 | 60 | 60 |
| | Monofunctional (meth)acrylate monomer | Kind | PhOEA | PhOEA | PhOEA | PhOEA | PhOEA |
| | | Added amount (parts by mass) | 40 | 40 | 40 | 40 | 40 |
| | Photo radical polymerization initiator (F-1) | Added amount (parts by mass) | 0.1 | 0.1 | 0.1 | 0.1 | 0.1 |
| | Thermal radical polymerization initiator (F-2, F-3) | Added amount (parts by mass) | 1.7 | 1.7 | 1.7 | 1.7 | 1.7 |
| Evaluation | Solvent solubility evaluation | | A | A | A | A | C |
| | Crack initiation evaluation | | A | A | A | A | C |
| | Transmittance | | A | A | A | A | A |
| | Refractive index | | 1.68 | 1.69 | 1.69 | 1.70 | 1.58 |

As shown in Table, the curable composition of the present invention had excellent solvent solubility while maintaining a high refractive index. Furthermore, the obtained cured material is excellent in crack initiation evaluation and also in transmittance.

On the other hand, the curable composition of Comparative Example 1-1 using an aromatic ring-containing compound different from the compound represented by Formula (1) of the present invention had poor solvent solubility. Further, the composition has lower refractive index than that in the example. Furthermore, cracks were liable to occur and the crack initiation evaluation was poor.

Examples 2-1 to 2-20, Comparative Examples 2-1

The components shown in the following Table were added to PGMEA heated to 60° C. at the ratio (part by mass) shown in the following Table and mixed using shaking machine to prepare PGMEA solution (curable composition) including components shown in Table at a ratio of 10% by mass.

The prepared curable composition was applied on various substrates (glass substrate (Matsunami Glass Industry Co., EAGLE XG, a diameter of 30 mm, a thickness of 500 µm)) and on one side of polyethylene terephthalate (PET) film (manufactured by Toyobo Co., A4300, 50 mm angle, a thickness of 100 µm), and was irradiated with ultraviolet light of the accumulated light intensity of 500 mJ/cm² by a high pressure mercury lamp, and further was heated (post-baking) for 30 minutes at 80° C. to give cured materials (a thickness of about 20 µm) which are stacked on a substrate. In Examples 2-1 to 2-20, the bleed-out was not confirmed after coating and after curing.

<Solvent Solubility Evaluation>

The solvent solubility of an aromatic ring-containing compound was measured in the same manner as described above.

<Crack Initiation Evaluation>

The cured material laminated on a glass substrate was charged into a constant temperature tank held in the 85° C., 85% RH. What crack occurs in the cured material obtained after 100 hours aging was set as a defective product and what crack does not occur was set as a non-defective product. Ten cured materials were evaluated and of which the percentage of non-defective was evaluated as non-defective rate by the following criteria.

A: Non-effective ratio was 80% or more

B: Non-effective ratio was 50% or more and less than 80%

C: Non-effective ratio was 30% or more and less than 50%

D: Non-effective ratio was less than 30%

<Transmittance Evaluation>

The cured material laminated on a glass substrate was evaluated by using an ultraviolet-visible absorption spectrum measurement apparatus UV-3100 (manufactured by Shimadzu Corporation) to measure the transmittance at a wavelength of 405 nm according to the following criteria.

A: Transmittance was 85% or more

B: Transmittance was less than 85%

<Refractive Index>

The refractive index of the cured material laminated on a polyethylene terephthalate substrate at 589 nm and hold the temperature of 25° C. was measured by using Abbe refractometer (manufactured by ATAGO CO., LTD., using DR-M2<circulating thermostatic water bath 60-C3>).

TABLE 3

|  |  |  | Example 2-1 | Example 2-2 | Example 2-3 | Example 2-4 | Example 2-5 |
|---|---|---|---|---|---|---|---|
| Compound | Aromatic ring-containing compound | Kind | Compound A | Compound B | Compound C | Compound D | Compound E |
|  |  | Added amount (parts by mass) | 100 | 100 | 100 | 100 | 100 |
|  | Photo radical polymerization initiator (F-1) | Added amount (parts by mass) | 3 | 3 | 3 | 3 | 3 |
| Evaluation | Solvent solubility evaluation |  | B | B | B | B | A |
|  | Crack initiation evaluation |  | B | B | A | A | A |
|  | Transmittance |  | B | A | A | A | A |
|  | Refractive index |  | 1.77 | 1.77 | 1.68 | 1.72 | 1.74 |
|  |  |  | Example 2-6 | Example 2-7 | Example 2-8 | Example 2-9 | Example 2-10 |
| Compound | Aromatic ring-containing compound | Kind | Compound F | Compound G | Compound H | Compound I | Compound J |
|  |  | Added amount (parts by mass) | 100 | 100 | 100 | 100 | 100 |
|  | Photo radical polymerization initiator (F-1) | Added amount (parts by mass) | 3 | 3 | 3 | 3 | 3 |
| Evaluation | Solvent solubility evaluation |  | B | B | B | A | A |
|  | Crack initiation evaluation |  | B | A | A | A | A |
|  | Transmittance |  | A | A | A | A | A |
|  | Refractive index |  | 1.67 | 1.67 | 1.78 | 1.69 | 1.72 |

TABLE 4

|  |  |  | Example 2-11 | Example 2-12 | Example 2-13 | Example 2-14 | Example 2-15 | Example 2-16 |
|---|---|---|---|---|---|---|---|---|
| Compound | Aromatic ring-containing compound | Kind | Compound 1 | Compound 2 | Compound 3 | Compound 4 | Compound 5 | Compound 6 |
|  |  | Added amount (parts by mass) | 100 | 100 | 100 | 100 | 100 | 100 |
|  | Photo radical polymerization initiator (F-1) | Added amount (parts by mass) | 3 | 3 | 3 | 3 | 3 | 3 |
| Evaluation | Solvent solubility evaluation |  | A | A | A | A | A | A |
|  | Crack initiation evaluation |  | A | A | A | A | A | A |
|  | Transmittance |  | A | A | A | A | A | A |
|  | Refractive index |  | 1.74 | 1.74 | 1.78 | 1.77 | 1.79 | 1.75 |
|  |  |  | Example 2-17 | Example 2-18 | Example 2-19 | Example 2-20 | Comparative Example 2-1 |  |
| Compound | Aromatic ring-containing compound | Kind | Compound 7 | Compound 8 | Compound 9 | Compound 10 | Comparative Compound 1 |  |
|  |  | Added amount (parts by mass) | 100 | 100 | 100 | 100 | 100 |  |
|  | Photo radical polymerization initiator (F-1) | Added amount (parts by mass) | 3 | 3 | 3 | 3 | 3 |  |
| Evaluation | Solvent solubility evaluation |  | A | A | A | A | C |  |
|  | Crack initiation evaluation |  | A | A | A | A | C |  |
|  | Transmittance |  | A | A | A | A | A |  |
|  | Refractive index |  | 1.78 | 1.80 | 1.80 | 1.82 | 1.62 |  |

As shown in Table 2, the curable composition of the present invention had excellent solvent solubility while maintaining a high refractive index. Furthermore, the obtained cured material is excellent in crack initiation evaluation and also in transmittance.

On the other hand, the curable composition of Comparative Example 2-1 using an aromatic ring-containing compound different from the compound represented by Formula (1) of the present invention had poor solvent solubility. Further, the composition has lower refractive index than that in the example. Furthermore, cracks were liable to occur and the crack initiation evaluation was poor.

What is claimed is:

1. A curable composition comprising:
   a compound represented by the following Formula (1); and
   at least one kind selected from thermal radical polymerization initiators or photo radical polymerization initiators,

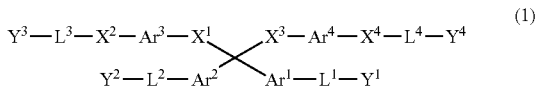

(1)

in Formula (1), $Ar^1$ to $Ar^4$ each independently represent an aromatic ring, $Ar^1$ and $Ar^2$, $Ar^3$ and $Ar^4$, $Ar^2$ and $Ar^3$, and $Ar^1$ and $Ar^4$ may link to each other to form a fused ring, respectively, at least one of $Ar^1$ to $Ar^4$ is a benzothiazole ring, a benzoxazole ring, an aromatic ring containing a benzothiazole ring or a benzoxazole ring, or an aromatic ring having a group including a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ represent an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^1$ to $X^4$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

2. The curable composition according to claim 1, wherein the compound represented by the above Formula (1) is a compound represented by the following Formula (11),

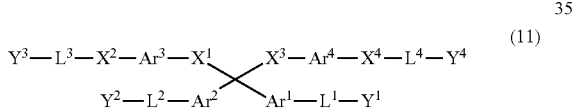

(11)

in Formula (11), $Ar^1$ to $Ar^4$ each independently represent a monocyclic aromatic ring to a tricyclic aromatic ring, $Ar^1$ and $Ar^2$ may have a phenyl group or a naphthyl group as a substituent, $Ar^1$ and $Ar^2$, or $Ar^a$ and $Ar^4$ may link to each other to form a fused ring containing a 5-membered ring or a 6-membered ring, at least one of $Ar^1$ to $Ar^4$ represents a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^1$ to $X^4$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

3. The curable composition according to claim 1, wherein the compound represented by the above Formula (1) is a compound represented by the following Formula (2),

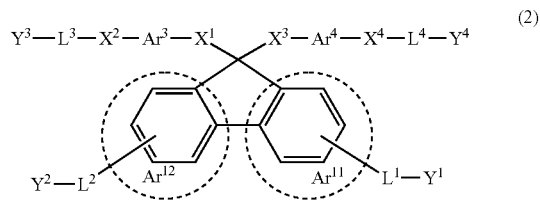

(2)

in Formula (2), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ are an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^1$ to $X^4$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

4. The curable composition according to claim 1, wherein the compound represented by the above Formula (1) is a compound represented by the following Formula (3A) or (3B),

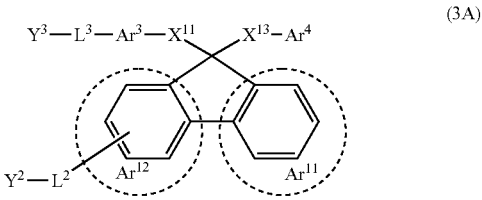

(3A)

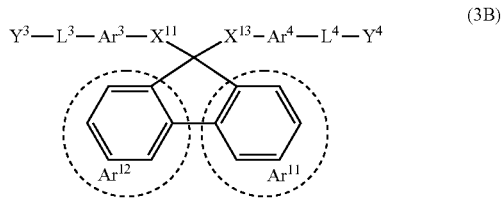

(3B)

in Formulae (3A) and (3B), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^2$ to $L^4$ each independently represent a single bond, an alkylene group, an alkenylene group, or an alkynylene group, in a case where $L^2$ to $L^4$ are an alkylene group, an alkenylene group, or an alkynylene group, $L^2$ to $L^4$ may include a divalent linking group selected from the group having one or more selected from —O—, —S—, —CO—, and —NR— in the linking chain, R represents a hydrogen atom or an alkyl group, $X^{11}$ and $X^{13}$ each independently represent a single bond, a phenylene group or a naphthylene group, at least one of $X^{11}$ or $X^{13}$ is a phenylene group or a naphthylene group, and $Y^2$ to $Y^4$ each independently represent a polymerizable group.

5. The curable composition according to claim 4, wherein at least one of $Ar^3$ or $Ar^4$ in the above Formula (3A) or Formula (3B) is a benzothiazole ring, a benzoxazole ring, an aromatic ring containing a benzothiazole ring or a benzoxazole ring, or an aromatic ring having a benzothiazolyl group or a benzoxazolyl group as a substituent.

6. The curable composition according to claim 4, wherein at least one of $Ar^3$ or $Ar^4$ in the above Formula (3A) or Formula (3B) is a benzothiazole ring, an aromatic ring having a benzothiazole ring, or an aromatic ring having a benzothiazolyl group as a substituent.

7. The curable composition according to claim 1, wherein the compound represented by the above Formula (1) is a compound represented by the following Formula (4),

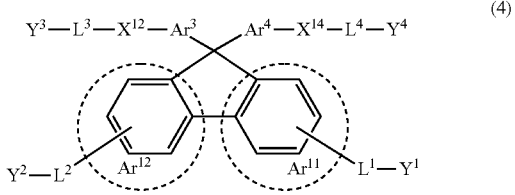

(4)

in Formula (4), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^1$ to $L^4$ each independently represent a single bond, an alkylene group, an alkenylene group, or an alkynylene group, in a case where $L^1$ to $L^4$ are an alkylene group, an alkenylene group, or an alkynylene group, $L^1$ to $L^4$ may include a divalent linking group selected from the group having one or more selected from —O—, —S—, —CO—, and —NR— in the linking chain, R represents a hydrogen atom or an alkyl group, $X^{12}$ and $X^{14}$ each independently represent a single bond, a phenylene group or a naphthylene group, $Y^1$ to $Y^4$ each independently represent a hydrogen atom or a polymerizable group, and two or more of $Y^1$ to $Y^4$ represent a polymerizable group.

8. The curable composition according to claim 1, wherein the compound represented by the above Formula (1) is a compound represented by the following Formula (5),

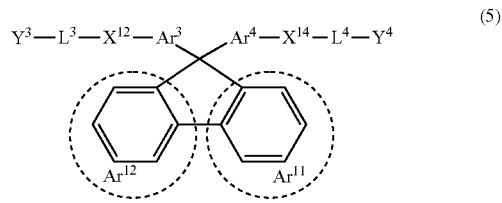

(5)

in Formula (5), $Ar^{11}$ and $Ar^{12}$ each independently represent an aromatic ring containing a benzene ring surrounded by a broken line, $Ar^3$ and $Ar^4$ each independently represent an aromatic ring, $Ar^3$ and $Ar^4$ may link to each other to form a fused ring, at least one of $Ar^{11}$, $Ar^{12}$, $Ar^3$ or $Ar^4$ is a benzothiazole ring, a benzoxazole ring, an aromatic ring containing a benzothiazole ring or a benzoxazole ring, or an aromatic ring having a benzothiazolyl group or a benzoxazolyl group as a substituent, $L^3$ and $L^4$ each independently represent a single bond, an alkylene group, an alkenylene group, or an alkynylene group, in a case where $L^3$ and $L^4$ are an alkylene group, an alkenylene group, or an alkynylene group, $L^3$ and $L^4$ may include a divalent linking group selected from the group having one or more selected from —O—, —S—, —CO—, and —NR— in the linking chain, R represents a hydrogen atom or an alkyl group, $X^{12}$ and $X^{14}$ each independently represent a single bond, a phenylene group or a naphthylene group, and $Y^3$ and $Y^4$ each independently represent a polymerizable group.

9. The curable composition according to claim 8, wherein at least one of $Ar^3$ or $Ar^4$ in the above Formula (5) is a benzothiazole ring, a benzoxazole ring, an aromatic ring containing a benzothiazole ring or a benzoxazole ring, or an aromatic ring having a benzothiazolyl group or a benzoxazolyl group as a substituent.

10. The curable composition according to claim 8, wherein at least one of $Ar^3$ or $Ar^4$ in the above Formula (5) is a benzothiazole ring, an aromatic ring having a benzothiazole ring, or an aromatic ring having a benzothiazolyl group as a substituent.

11. The curable composition according to claim 8, wherein $Ar^3$ in the above Formula (5) is a benzothiazole ring, an aromatic ring having a benzothiazole ring, or an aromatic ring having a benzothiazolyl group as a substituent, and $X^{12}$ is a phenylene group or a naphthylene group, and/or $Ar^4$ is a benzothiazole ring, an aromatic ring having a benzothiazole ring, or an aromatic ring having a benzothiazolyl group as a substituent, and $X^{14}$ is a phenylene group or a naphthylene group.

12. The curable composition according to claim 1, further comprising a thermal radical polymerization initiator and a photo radical polymerization initiator.

13. The curable composition according to claim 1, further comprising a monofunctional (meth)acrylate monomer in a proportion of 10% by mass to 200% by mass with respect to the compound represented by the above Formula (1).

14. An optical component using the curable composition according to claim 1.

15. A compound represented by the following Formula (11),

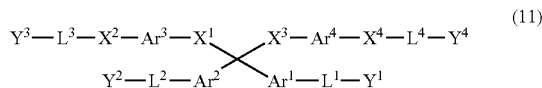

(11)

in Formula (11), $Ar^1$ to $Ar^4$ each independently represent a monocyclic aromatic ring to a tricyclic aromatic ring, $Ar^1$ and $Ar^2$ may have a phenyl group or a naphthyl group as a substituent, $Ar^1$ and $Ar^2$, or $Ar^a$ and $Ar^4$ may link to each other to form a fused ring containing a 5-membered ring or a 6-membered ring, at least one of $Ar^1$ to $Ar^4$ represents a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^1$ to $X^4$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

16. The compound according to claim 15, wherein the compound represented by the above Formula (11) is a compound represented by the following Formula (12),

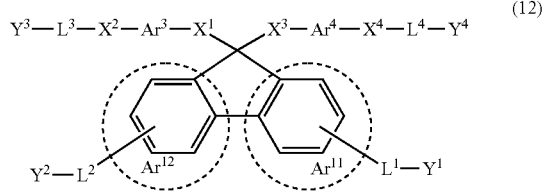

(12)

in Formula (12), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^1$ to $X^4$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

17. The compound according to claim 15, wherein the compound represented by the above Formula (11) is a compound represented by the following Formula (13A) or (13B),

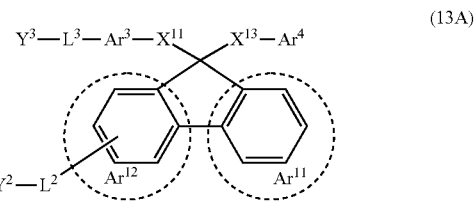

(13A)

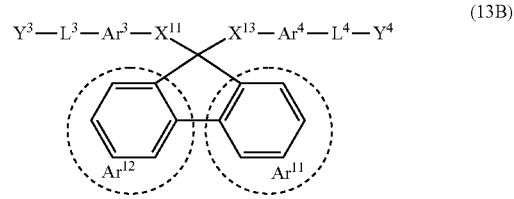

(13B)

in Formulae (13A) and (13B), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^2$ to $L^4$ each independently represent an alkylene group having 1 to 20 carbon atoms, in a case where $L^2$ to $L^4$ are an alkylene group having 2 to 20 carbon atoms, $L^2$ to $L^4$ may include a divalent linking group selected from the group having one or more selected from —O—, —S—, —CO—, and —NH— in the linking chain, $X^{11}$ and $X^{13}$ each independently represent a single bond, a phenylene group or a naphthylene group, at least one of $X^{11}$ or $X^{13}$ is a phenylene group or a naphthylene group, and $Y^2$ to $Y^4$ each independently represent a polymerizable group having an ethylenically unsaturated bond.

18. The compound according to claim 17, wherein at least one of $Ar^3$ or $Ar^4$ in the above Formula (13A) or Formula (13B) is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent.

19. The compound according to claim 17, wherein at least one of $Ar^3$ or $Ar^4$ in the above Formula (13A) or Formula (13B) is a benzothiazole ring, a tricyclic aromatic ring containing a benzothiazole ring, or a benzene ring or a naphthalene ring having a benzothiazolyl group as a substituent.

20. The compound according to claim 15, wherein the compound represented by the above Formula (11) is a compound represented by the following Formula (14),

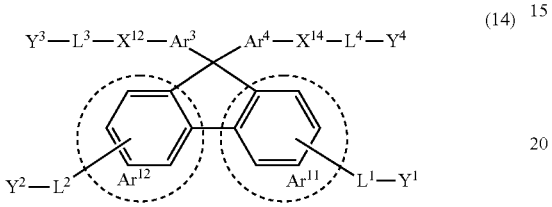
(14)

in Formula (14), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^1$ to $L^4$ each independently represent a single bond or an alkylene group having 1 to 20 carbon atoms, in a case where $L^1$ to $L^4$ are an alkylene group having 2 to 20 carbon atoms, $L^1$ to $L^4$ may include a divalent linking group selected from the group having one or more selected from —O—, —S—, —CO—, and —NH— in the linking chain, $X^{12}$ and $X^{14}$ each independently represent a single bond, a phenylene group or a naphthylene group, $Y^1$ to $Y^4$ each independently represent a hydrogen atom or a polymerizable group having an ethylenically unsaturated bond, and two or more of $Y^1$ to $Y^4$ represent a polymerizable group having an ethylenically unsaturated bond.

21. The compound according to claim 15, wherein the compound represented by the above Formula (11) is a compound represented by the following Formula (15),

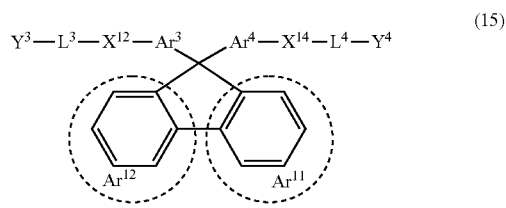
(15)

in Formula (15), $Ar^{11}$ and $Ar^{12}$ each independently represent a monocyclic aromatic ring to a tricyclic aromatic ring including a benzene ring surrounded by a broken line, $Ar^{11}$ and $Ar^{12}$ may have a phenyl group or a naphthyl group as a substituent, $Ar^3$ and $Ar^4$ each independently represent a monocyclic aromatic ring to a tricyclic aromatic ring, at least one of $Ar^{11}$, $Ar^{12}$, $Ar^3$ or $Ar^4$ is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent, $L^3$ and $L^4$ each independently represent an alkylene group having 1 to 20 carbon atoms, in a case where $L^3$ and $L^4$ are an alkylene group having 2 to 20 carbon atoms, $L^3$ and $L^4$ may include a divalent linking group selected from the group having one or more selected from —O—, —S—, —CO—, and —NH— in the linking chain, $X^{12}$ and $X^{14}$ each independently represent a single bond, a phenylene group or a naphthylene group, and $Y^3$ and $Y^4$ each independently represent a polymerizable group having an ethylenically unsaturated bond.

22. The compound according to claim 21, wherein at least one of $Ar^3$ or $Ar^4$ in the above Formula (15) is a benzothiazole ring, a benzoxazole ring, a tricyclic aromatic ring containing a benzothiazole ring or a benzoxazole ring, or a benzene ring or a naphthalene ring having a benzothiazolyl group or a benzoxazolyl group as a substituent.

23. The compound according to claim 21, wherein at least one of $Ar^3$ or $Ar^4$ in the above Formula (15) is a benzothiazole ring, a tricyclic aromatic ring containing a benzothiazole ring, or a benzene ring or a naphthalene ring having a benzothiazolyl group as a substituent.

24. The compound according to claim 21, wherein $Ar^3$ in the above Formula (15) is a benzothiazole ring, a tricyclic aromatic ring containing a benzothiazole ring, or a benzene ring or a naphthalene ring having a benzothiazolyl group as a substituent, and $X^{12}$ is a phenylene group or a naphthylene group, and/or $Ar^4$ is a benzothiazole ring, a tricyclic aromatic ring containing a benzothiazole ring, or a benzene ring or a naphthalene ring having a benzothiazolyl group as a substituent, and $X^{14}$ is a phenylene group or a naphthylene group.

* * * * *